(12) United States Patent
Fernandes et al.

(10) Patent No.: US 7,994,402 B2
(45) Date of Patent: Aug. 9, 2011

(54) METHOD OF INCREASING PLANT ORGAN AND SEED SIZE IN A PLANT

(75) Inventors: Mary Fernandes, St. Louis, MO (US); Zhidong Xie, Maryland Heights, MO (US); Stanton B. Dotson, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 761 days.

(21) Appl. No.: 12/001,901

(22) Filed: Dec. 13, 2007

(65) Prior Publication Data

US 2009/0133162 A1 May 21, 2009

Related U.S. Application Data

(62) Division of application No. 10/513,167, filed as application No. PCT/US03/14989 on May 14, 2003, now Pat. No. 7,335,812.

(60) Provisional application No. 60/381,100, filed on May 15, 2002.

(51) Int. Cl.
*C12N 15/82* (2006.01)
*A01H 5/00* (2006.01)
*A01H 5/10* (2006.01)

(52) U.S. Cl. ............... 800/320.1; 800/278; 800/290; 800/287; 800/298

(58) Field of Classification Search ............... None
See application file for complete search history.

(56) References Cited

U.S. PATENT DOCUMENTS

| | | |
|---|---|---|
| 2002/0160378 A1 | 10/2002 | Harper et al. |
| 2009/0183270 A1* | 7/2009 | Adams et al. ............... 800/260 |

FOREIGN PATENT DOCUMENTS

| | | |
|---|---|---|
| WO | WO 98/35044 | 8/1998 |
| WO | WO 00/52172 | 9/2000 |
| WO | WO 01/64928 | 9/2001 |
| WO | WO 02/10210 | 2/2002 |
| WO | WO 02/016655 | 2/2002 |

OTHER PUBLICATIONS

Bowie et al, Science 247:1306-1310, 1990.*
McConnell et al, Nature 411 (6838):709-713, 2001.*
Kano-Murakami et al (1993, FEBS 334:365-368).*
EMBL Database accession No. AY065111, Dec. 12, 2001, *Arabidopsis thaliana putative tropinone reductase* (At2g29350; F16P2.27) *mRNA, complete cds* (labeled XP-002363392).
EMBL Database accession No. Q9ZW18, May 1, 1999, *Putative tropinone reductase* (AT2G29350/F16P2.27) (labeled XP-002363393).
Bowie, James U., et al., Deciphering the message in protein sequences: tolerance to amino acid substitutions, *Science* 247:1306-1310 (1990).
Kano-Murakami, Yuriko, et al., A rice homeotic gene, *OSH1*, causes unusual phenotypes in transgenic tobacco, *Federation of European Biochemical Societies* 334(3):365-368 (1993).
Keiner, Ronald, et al., Accumulation and biosynthesis of calystegines in potato, *Journal of Applied Botany* 74:122-125 (2000).
Keiner, Ronald, et al., Molecular cloning, expression and characterization of tropinone reductase II, an enzyme of the SDR family in *Solanum tuberosum* (L.), *Plant Molecular Biology* 48:299-308 (2002) (labeled XP-002363389).
McConnell, Jane R., et al., Role of *Phabulosa* and *Phavoluta* in determining radial patterning in shoots, *Nature* 411:709-713 (2001).

* cited by examiner

*Primary Examiner* — Stuart F. Baum
(74) *Attorney, Agent, or Firm* — Winston & Strawn LLP

(57) ABSTRACT

The present invention provides methods and DNA molecules useful for producing transgenic plants with agronomically desired traits based on altered sizes of plant organs and tissues.

9 Claims, 12 Drawing Sheets

| Primers | Sequence ID No. | Structural Comments |
|---|---|---|
| Arabidopsis Primers | | |
| GTAAGATATCATATGGCAAAGG AAGGG | SEQ ID No: 57 | BgIII and NdeI site N-terminal histag |
| GCGCGAATTCTCGAGTCATAGTC TTGAAGGAAAAAC | SEQ ID No: 58 | Has EcorI and XhoI |
| GGCTACAAATCTCGAGTCAGC | SEQ ID No: 59 | |
| GCTGACTCGAGATTTGTAGCC | SEQ ID No: 60 | |
| Nostoc Primers | | |
| GTAAGATATCATATGAGTGATGC CTACGGTG | SEQ ID No: 61 | NdeI site N-terminal histag |
| GTAAGATCTGCCACCATGGGTGA TGCCTACGGTG | SEQ ID No: 62 | Modified 2nd codon for NcoI site Ser to Gly) |
| GAGAAGCTTCTCGAGTTAAAAA CCGAAAGCC | SEQ ID No: 63 | (HindIII/XhoI) |
| CCTCTACTGCAAATAGGG | SEQ ID No: 64 | |
| CCCTATTTGCAGTAGAGG | SEQ ID No: 65 | |

FIG. 10

SEQUENCE LISTING

<160> NUMBER OF SEQ ID NOS: 71

<210> SEQ ID NO 1
<211> LENGTH: 812
<212> TYPE: DNA
<213> ORGANISM: Arabidopsis thaliana

<400> SEQUENCE: 1

```
ccatggcaaa ggaaggggc ttgggagaga actcaagatg gagtcttgga ggcatgaccg      60
ctcttgtcac tggtggctct aaaggcatcg gggaagctgt ggtggaggaa ctagccatgt     120
tgggagcaaa agtccacacg tgtgccagag acgaaactca gcttcaagaa cgcttacgtg     180
aatggcaagc aaaaggtttt caggtcacca cttctgtctg cgacgtctct tctcgtgacc     240
aacgagtgaa actcatggaa actgtttcct ctctctacca aggaaaactc aacatcctcg     300
tcaacaatgt gggaacgtca atattcaagc cgaccacaga gtatacagca gaagatttct     360
cttttgtaat ggctacaaat ctcgagtcag cttttccatct ctcacagctt gcccacccat     420
tgttaaaagc ctctggctca gggagcatcg tgctcatatc ctctgctgct ggagtcgtgc     480
atgtcaatgt tggatccatc tatggagcaa ccaaaggagc catgaatcag ctggctagaa     540
acttagcttg cgaatgggcg agcgacaaca taaggacgaa ctctgtttgt ccttggtata     600
tcacaactcc tttaagtaac gattttttc gatgaagagt ttaagaaaga agcggtgcgt     660
acgacaccaa tggggcgtgt tggagaagca aatgaagtct caccgcttgt ggcatttctt     720
tgtcttcctt cagcttctta tattactggt cagaccattt gcgttgacgg cggtgccact     780
gttaacggtt tttccttcaa gactatgaat tc                                   812
```

<210> SEQ ID NO 2
<211> LENGTH: 210
<212> TYPE: PRT
<213> ORGANISM: Arabidopsis thaliana

<400> SEQUENCE: 2

```
Met Ala Lys Glu Gly Gly Leu Gly Glu Asn Ser Arg Trp Ser Leu Gly
1               5                   10                  15

Gly Met Thr Ala Leu Val Thr Gly Gly Ser Lys Gly Ile Gly Glu Ala
            20                  25                  30

Val Val Glu Glu Leu Ala Met Leu Gly Ala Lys Val His Thr Cys Ala
        35                  40                  45

Arg Asp Glu Thr Gln Leu Gln Glu Arg Leu Arg Glu Trp Gln Ala Lys
    50                  55                  60

Gly Phe Gln Val Thr Thr Ser Val Cys Asp Val Ser Ser Arg Asp Gln
```

```
                65                  70                  75                  80
Arg Val Lys Leu Met Glu Thr Val Ser Ser Leu Tyr Gln Gly Lys Leu
                        85                  90                  95
Asn Ile Leu Val Asn Asn Val Gly Thr Ser Ile Phe Lys Pro Thr Thr
                    100                 105                 110
Glu Tyr Thr Ala Glu Asp Phe Ser Phe Val Met Ala Thr Asn Leu Glu
                115                 120                 125
Ser Ala Phe His Leu Ser Gln Leu Ala His Pro Leu Leu Lys Ala Ser
            130                 135                 140
Gly Ser Gly Ser Ile Val Leu Ile Ser Ser Ala Ala Gly Val Val His
145                 150                 155                 160
Val Asn Val Gly Ser Ile Tyr Gly Ala Thr Lys Gly Ala Met Asn Gln
                165                 170                 175
Leu Ala Arg Asn Leu Ala Cys Glu Trp Ala Ser Asp Asn Ile Arg Thr
                180                 185                 190
Asn Ser Val Cys Pro Trp Tyr Ile Thr Thr Pro Leu Ser Asn Asp Phe
                195                 200                 205
Phe Arg
    210

<210> SEQ ID NO 3
<211> LENGTH: 810
<212> TYPE: DNA
<213> ORGANISM: Arabidopsis thaliana

<400> SEQUENCE: 3
ccatggcaaa ggaaggggc ttgggagaga actcaagatg gagtcttgga ggcatgaccg      60
ctcttgtcac tggtggctct aaaggcatcg gggaagctgt ggtggaggaa ctagccatgt     120
tgggagcaaa agtccacacg tgtgccagag acgaaactca gcttcaagaa cgcttacgtg     180
aatggcaagc aaaagggttt caggtcacca cttctgtctg cgacgtctct tctcgtgacc     240
aacgagtgaa actcatggaa actgtttcct ctctctacca aggaaaactc aacatcctcg     300
tcaacaatgt gggaacgtca atattcaagc cgaccacaga gtatacagca gaagatttct     360
cttttgtaat ggctacaaat ctcgagtcag cttttccatct ctcacagctt gcccacccat     420
tgttaaaagc tctggctca gggagcatcg tgctcatatc ctctgctgct ggagtcgtgc     480
atgtcaatgt tggatccatc tatggagcaa ccaaaggagc catgaatcag ctggctagaa     540
acttagcttg cgaatgggcg agcgacaaca taggacgaa ctctgttgt ccttggtata     600
tcacaactcc tttaagtaac gattttttcg atgaagagtt aagaaagaa gcggtgcgta     660
cgacaccaat ggggcgtgtg gagaagcaaa tgaagtctca ccgcttgtgg catttctttg     720
tcttccttca gcttcttata ttactggtca gaccatttgc gttgacggcg gtgccactgt     780
taacggtttt ccttcaaga ctatgaattc                                      810

<210> SEQ ID NO 4
<211> LENGTH: 268
<212> TYPE: PRT
<213> ORGANISM: Arabidopsis thaliana

<400> SEQUENCE: 4

Met Ala Lys Glu Gly Gly Leu Gly Glu Asn Ser Arg Trp Ser Leu Gly
1               5                   10                  15
Gly Met Thr Ala Leu Val Thr Gly Gly Ser Lys Gly Ile Gly Glu Ala
                20                  25                  30
Val Val Glu Glu Leu Ala Met Leu Gly Ala Lys Val His Thr Cys Ala
```

```
                35                  40                  45
Arg Asp Glu Thr Gln Leu Gln Glu Arg Leu Arg Glu Trp Gln Ala Lys
 50                  55                  60

Gly Phe Gln Val Thr Thr Ser Val Cys Asp Val Ser Ser Arg Asp Gln
 65                  70                  75                  80

Arg Val Lys Leu Met Glu Thr Val Ser Ser Leu Tyr Gln Gly Lys Leu
                 85                  90                  95

Asn Ile Leu Val Asn Asn Val Gly Thr Ser Ile Phe Lys Pro Thr Thr
            100                 105                 110

Glu Tyr Thr Ala Glu Asp Phe Ser Phe Val Met Ala Thr Asn Leu Glu
        115                 120                 125

Ser Ala Phe His Leu Ser Gln Leu Ala His Pro Leu Leu Lys Ala Ser
    130                 135                 140

Gly Ser Gly Ser Ile Val Leu Ile Ser Ser Ala Ala Gly Val Val His
145                 150                 155                 160

Val Asn Val Gly Ser Ile Tyr Gly Ala Thr Lys Gly Ala Met Asn Gln
                165                 170                 175

Leu Ala Arg Asn Leu Ala Cys Glu Trp Ala Ser Asp Asn Ile Arg Thr
            180                 185                 190

Asn Ser Val Cys Pro Trp Tyr Ile Thr Thr Pro Leu Ser Asn Asp Phe
        195                 200                 205

Phe Asp Glu Glu Phe Lys Lys Glu Ala Val Arg Thr Thr Pro Met Gly
    210                 215                 220

Arg Val Gly Glu Ala Asn Glu Val Ser Pro Leu Val Ala Phe Leu Cys
225                 230                 235                 240

Leu Pro Ser Ala Ser Tyr Ile Thr Gly Gln Thr Ile Cys Val Asp Gly
                245                 250                 255

Gly Ala Thr Val Asn Gly Phe Ser Phe Lys Thr Met
            260                 265

<210> SEQ ID NO 5
<211> LENGTH: 789
<212> TYPE: DNA
<213> ORGANISM: Arabidopsis thaliana

<400> SEQUENCE: 5
atggataaaa gatggagtct tcaaggtatg aatgctcttg tgaccggtgg cactaaaggc      60
atcggggaag ctgttgtgga ggaactgtca attttgggag caagagtcca cacatgtgct    120
agagacgaga ctcagcttca agaacgttta cgtgaatggc aagaaaaagg gtttcaggtc    180
accacttcta tctgcgacgt ttcttttgcgt gagcaacgag agaaactcat ggaaaccgtt    240
tcctctctct tccaaggaaa actcaacatc ctcgtgaaca atgtgggaac gttaatgctc    300
aagccgacca cagagtatac agcagaagaa ttctcgtttc ttatggctac aaatctcgac    360
tcagcttttc atatttcaca gcttgcgcac ccttttgtta aagcctctgg ctcagggagc    420
attgtgctca tgtcctctat tgccggagtc gtgcatgtcg gtgttggatc catctatgga    480
gcaacaaaag gagccatgaa tcagttggct agaaacttag cttgcgaatg ggcaagcgac    540
aacataagga ctaacgctat tgtccatgg ttaatcacaa ctcctttgat tagtgatctt    600
ctcagtgttg aggagatgaa aaagaagca gaggaaagga cacccatggg gcgtgtggga    660
gaggcaaatg aagtctcacc gcttgtggca tttctttgtc ttcctgcagc ttcttatatt    720
actggtcaag tcatttgtgt tgatggaggt ctcactgtta atggcttctc ctatcagcca    780
catgcttga                                                            789
```

```
<210> SEQ ID NO 6
<211> LENGTH: 262
<212> TYPE: PRT
<213> ORGANISM: Arabidopsis thaliana

<400> SEQUENCE: 6

Met Asp Lys Arg Trp Ser Leu Gln Gly Met Asn Ala Leu Val Thr Gly
1               5                   10                  15

Gly Thr Lys Gly Ile Gly Glu Ala Val Val Glu Leu Ser Ile Leu
            20                  25                  30

Gly Ala Arg Val His Thr Cys Ala Arg Asp Glu Thr Gln Leu Gln Glu
        35                  40                  45

Arg Leu Arg Glu Trp Gln Glu Lys Gly Phe Gln Val Thr Thr Ser Ile
    50                  55                  60

Cys Asp Val Ser Leu Arg Glu Gln Arg Glu Lys Leu Met Glu Thr Val
65                  70                  75                  80

Ser Ser Leu Phe Gln Gly Lys Leu Asn Ile Leu Val Asn Asn Val Gly
                85                  90                  95

Thr Leu Met Leu Lys Pro Thr Thr Glu Tyr Thr Ala Glu Glu Phe Ser
            100                 105                 110

Phe Leu Met Ala Thr Asn Leu Asp Ser Ala Phe His Ile Ser Gln Leu
        115                 120                 125

Ala His Pro Leu Leu Lys Ala Ser Gly Ser Gly Ser Ile Val Leu Met
    130                 135                 140

Ser Ser Ile Ala Gly Val Val His Val Gly Val Gly Ser Ile Tyr Gly
145                 150                 155                 160

Ala Thr Lys Gly Ala Met Asn Gln Leu Ala Arg Asn Leu Ala Cys Glu
                165                 170                 175

Trp Ala Ser Asp Asn Ile Arg Thr Asn Ala Ile Cys Pro Trp Leu Ile
            180                 185                 190

Thr Thr Pro Leu Ile Ser Asp Leu Leu Ser Val Glu Glu Met Lys Lys
        195                 200                 205

Glu Ala Glu Glu Arg Thr Pro Met Gly Arg Val Gly Glu Ala Asn Glu
    210                 215                 220

Val Ser Pro Leu Val Ala Phe Leu Cys Leu Pro Ala Ala Ser Tyr Ile
225                 230                 235                 240

Thr Gly Gln Val Ile Cys Val Asp Gly Gly Leu Thr Val Asn Gly Phe
                245                 250                 255

Ser Tyr Gln Pro His Ala
            260

<210> SEQ ID NO 7
<211> LENGTH: 807
<212> TYPE: DNA
<213> ORGANISM: Arabidopsis thaliana

<400> SEQUENCE: 7
atggctaaag cagaagaaaa cttgagagac aaatgtagat ggagccttgg aggcatgacc      60
gctctcgtta ccggtggctc caaaggcctc ggggaagctg tggtggagga actagccatg     120
ttaggagcaa gagtccacac atgtgctaga acgaaactc agcttcaaga atgcgtacgt      180
gaatggcaag ctaaagggtt tgaggtcacc acttctgtat gcgacgtttc ttctcgtgac    240
caacgagaga aactcatgga aaacgttgcc tctatcttcc aaggaaaact caacatcctt    300
gtaaacaatg cgggaacggg tataacaaag ccgaccacag tatacagc acaagattac      360 tcatttctga tggctacaaa tctcgactca gcttttcatc tctcacagct cgcgcatcct    420
```

```
ttgttgaaag catctggttc agggagcatc gtgctcatgt cctctactgc aggggttgta   480
catatcaatg ttggttccat ctatggagca actaaaggag ctatgaatca gctagcaaaa   540
aacttagcat gcgagtgggc aagggataac ataagggtta attctgtctg tccatggttc   600
atagcaactc ctttatatct caatgatgaa gagttaaaga aagaagtgga gcgtaagaca   660
ccaatgggac gtgttggaaa cgcaaatgaa gtatcatcgc ttgtcgcatt tctctgcttt   720
ccggctgctt cgtatataac aggtcagaca atctgcgtcg acggaggttt cacggtcaac   780
tgcttttctt tcaagccagt gctttaa                                      807
```

```
<210> SEQ ID NO 8
<211> LENGTH: 268
<212> TYPE: PRT
<213> ORGANISM: Arabidopsis thaliana

<400> SEQUENCE: 8

Met Ala Lys Ala Glu Glu Asn Leu Arg Asp Lys Cys Arg Trp Ser Leu
1               5                   10                  15

Gly Gly Met Thr Ala Leu Val Thr Gly Gly Ser Lys Gly Leu Gly Glu
                20                  25                  30

Ala Val Val Glu Glu Leu Ala Met Leu Gly Ala Arg Val His Thr Cys
            35                  40                  45

Ala Arg Asn Glu Thr Gln Leu Gln Glu Cys Val Arg Glu Trp Gln Ala
        50                  55                  60

Lys Gly Phe Glu Val Thr Thr Ser Val Cys Asp Val Ser Ser Arg Asp
65                  70                  75                  80

Gln Arg Glu Lys Leu Met Glu Asn Val Ala Ser Ile Phe Gln Gly Lys
                85                  90                  95

Leu Asn Ile Leu Val Asn Asn Ala Gly Thr Gly Ile Thr Lys Pro Thr
            100                 105                 110

Thr Glu Tyr Thr Ala Gln Asp Tyr Ser Phe Leu Met Ala Thr Asn Leu
        115                 120                 125

Asp Ser Ala Phe His Leu Ser Gln Leu Ala His Pro Leu Leu Lys Ala
    130                 135                 140

Ser Gly Ser Gly Ser Ile Val Leu Met Ser Ser Thr Ala Gly Val Val
145                 150                 155                 160

His Ile Asn Val Gly Ser Ile Tyr Gly Ala Thr Lys Gly Ala Met Asn
                165                 170                 175

Gln Leu Ala Lys Asn Leu Ala Cys Glu Trp Ala Arg Asp Asn Ile Arg
            180                 185                 190

Val Asn Ser Val Cys Pro Trp Phe Ile Ala Thr Pro Leu Tyr Leu Asn
        195                 200                 205

Asp Glu Glu Leu Lys Lys Glu Val Glu Arg Lys Thr Pro Met Gly Arg
    210                 215                 220

Val Gly Asn Ala Asn Glu Val Ser Ser Leu Val Ala Phe Leu Cys Phe
225                 230                 235                 240

Pro Ala Ala Ser Tyr Ile Thr Gly Gln Thr Ile Cys Val Asp Gly Gly
                245                 250                 255

Phe Thr Val Asn Cys Phe Ser Phe Lys Pro Val Leu
            260                 265

<210> SEQ ID NO 9
<211> LENGTH: 807
<212> TYPE: DNA
<213> ORGANISM: Arabidopsis thaliana
```

<400> SEQUENCE: 9

```
atggctaaag caggagaaaa ctcgagagac aaatctagat ggagccttga aggcatgacc      60
gctcttgtta caggtggctc caaaggcctc ggagaagctg tagtggagga actagccatg     120
ttgggagcaa gagttcacac atgtgccaga gacgaaactc agcttcaaga acgcttacgt     180
gaatggcaag ccaaaggatt tgaggtcacc acttctgtct gcgacgtctc ttctcgtgag     240
caacgagaga aactcatgga aaccgttccc tctgtcttcc aaggaaaact caacatcctc     300
gtaaataatg cgggaacggg tataataaag ccgagtacag agtatacagc agaagattac     360
tcgtttctga tggctacaaa tctcgagtcc gcttttcatc tctcacagat cgcgcaccct     420
tgttgaaaag cctctggttc cgggagcatc gtgttcatgt cctctgttgc tggacttgtg     480
cataccggtg catcaatcta tggagcatct aaaggagcta tgaatcagct aggaagaagc     540
ttagcatgcg agtgggcaag tgacaacata agggttaact ctgtgtgtcc atgggtcata     600
acaactcctt taactagctt tattttcagt gatgaaaagt taagaaaagc agtggaggat     660
aagacaccaa tgggacgtgt tggagaagca aatgaagtat catcgcttgt cgcatttctc     720
tgttttccgg cagcttctta tattacaggt cagactatct gcgtcgacgg aggtgcttcg     780
gtgaatggct ctctttcaa gccttag                                          807
```

<210> SEQ ID NO 10
<211> LENGTH: 268
<212> TYPE: PRT
<213> ORGANISM: Arabidopsis thaliana

<400> SEQUENCE: 10

```
Met Ala Lys Ala Gly Glu Asn Ser Arg Asp Lys Ser Arg Trp Ser Leu
  1               5                  10                  15

Glu Gly Met Thr Ala Leu Val Thr Gly Gly Ser Lys Gly Leu Gly Glu
             20                  25                  30

Ala Val Val Glu Glu Leu Ala Met Leu Gly Ala Arg Val His Thr Cys
         35                  40                  45

Ala Arg Asp Glu Thr Gln Leu Gln Glu Arg Leu Arg Glu Trp Gln Ala
     50                  55                  60

Lys Gly Phe Glu Val Thr Thr Ser Val Cys Asp Val Ser Ser Arg Glu
 65                  70                  75                  80

Gln Arg Glu Lys Leu Met Glu Thr Val Ser Val Phe Gln Gly Lys
                 85                  90                  95

Leu Asn Ile Leu Val Asn Asn Ala Gly Thr Gly Ile Ile Lys Pro Ser
            100                 105                 110

Thr Glu Tyr Thr Ala Glu Asp Tyr Ser Phe Leu Met Ala Thr Asn Leu
        115                 120                 125

Glu Ser Ala Phe His Leu Ser Gln Ile Ala His Pro Leu Leu Lys Ala
    130                 135                 140

Ser Gly Ser Gly Ser Ile Val Phe Met Ser Ser Val Ala Gly Leu Val
145                 150                 155                 160

His Thr Gly Ala Ser Ile Tyr Gly Ala Ser Lys Gly Ala Met Asn Gln
                165                 170                 175

Leu Gly Arg Ser Leu Ala Cys Glu Trp Ala Ser Asp Asn Ile Arg Val
            180                 185                 190

Asn Ser Val Cys Pro Trp Val Ile Thr Thr Pro Leu Thr Ser Phe Ile
        195                 200                 205

Phe Ser Asp Glu Lys Leu Arg Lys Ala Val Glu Asp Lys Thr Pro Met
    210                 215                 220
```

Gly Arg Val Gly Glu Ala Asn Glu Val Ser Ser Leu Val Ala Phe Leu
225                 230                 235                 240

Cys Phe Pro Ala Ala Ser Tyr Ile Thr Gly Gln Thr Ile Cys Val Asp
                245                 250                 255

Gly Gly Ala Ser Val Asn Gly Phe Ser Phe Lys Pro
            260                 265

<210> SEQ ID NO 11
<211> LENGTH: 807
<212> TYPE: DNA
<213> ORGANISM: Arabidopsis thaliana

<400> SEQUENCE: 11

| | | | | | | |
|---|---|---|---|---|---|---|
| atggcaaaga | gaggggaaag | cttgagagac | aaacctaaat | ggagtcttga | aggcatgact | 60 |
| gctcttgtta | ccggtggatc | taaaggcctc | ggaaaagctg | tggtggagga | actagccatg | 120 |
| ttgggagcaa | gagttcacac | atgtgccaga | gacgaaactc | agcttcaaga | aagcttacgt | 180 |
| gaatggcaag | caaaagggtt | acaagtcacc | acttctgttt | gcgatgtttc | ttctcgtgac | 240 |
| cagcgagaga | aactcatgga | aactgtttcc | tctctcttcc | aaggaaaact | cagcatcctc | 300 |
| gtacccaatg | tgggaatagg | tgtactaaag | ccgacgactg | agtgtacagc | agaagagttc | 360 |
| tcatttataa | tagctacaaa | tctggagtca | actttccatt | tctcgcaact | cgcgcatcct | 420 |
| ttattgaaag | cctctggttc | agggaacatt | gtgctcatgt | cttccgtggc | tggagttgta | 480 |
| aatttgggta | tacatcaat | ctatggagca | accaaggag | ccatgaatca | gctggcgaga | 540 |
| aatttagcat | gcgagtgggc | gagtgataat | ataagggcta | attctgtttg | tccatggttc | 600 |
| attacaactc | cgtcaactaa | agatttcctc | ggtgataaag | atgtaaaaga | aaaggtggag | 660 |
| agtgtgacac | cattgagacg | tgttggagag | gcaaatgaag | tatcatcgct | tgttgcattt | 720 |
| ctatgtcttc | ccgcagcttc | ttatataaca | ggtcaaacca | tttgcgttga | tggaggtttc | 780 |
| actattaacg | gcttctcttt | gccttaa | | | | 807 |

<210> SEQ ID NO 12
<211> LENGTH: 268
<212> TYPE: PRT
<213> ORGANISM: Arabidopsis thaliana

<400> SEQUENCE: 12

Met Ala Lys Arg Gly Glu Ser Leu Arg Asp Lys Pro Lys Trp Ser Leu
1               5                   10                  15

Glu Gly Met Thr Ala Leu Val Thr Gly Gly Ser Lys Gly Leu Gly Lys
                20                  25                  30

Ala Val Val Glu Glu Leu Ala Met Leu Gly Ala Arg Val His Thr Cys
            35                  40                  45

Ala Arg Asp Glu Thr Gln Leu Gln Glu Ser Leu Arg Glu Trp Gln Ala
        50                  55                  60

Lys Gly Leu Gln Val Thr Thr Ser Val Cys Asp Val Ser Ser Arg Asp
65                  70                  75                  80

Gln Arg Glu Lys Leu Met Glu Thr Val Ser Ser Leu Phe Gln Gly Lys
                85                  90                  95

Leu Ser Ile Leu Val Pro Asn Val Gly Ile Gly Val Leu Lys Pro Thr
            100                 105                 110

Thr Glu Cys Thr Ala Glu Glu Phe Ser Phe Ile Ile Ala Thr Asn Leu
        115                 120                 125

Glu Ser Thr Phe His Phe Ser Gln Leu Ala His Pro Leu Leu Lys Ala
        130                 135                 140

```
Ser Gly Ser Gly Asn Ile Val Leu Met Ser Ser Val Ala Gly Val Val
145                 150                 155                 160

Asn Leu Gly Asn Thr Ser Ile Tyr Gly Ala Thr Lys Gly Ala Met Asn
            165                 170                 175

Gln Leu Ala Arg Asn Leu Ala Cys Glu Trp Ala Ser Asp Asn Ile Arg
        180                 185                 190

Ala Asn Ser Val Cys Pro Trp Phe Ile Thr Thr Pro Ser Thr Lys Asp
        195                 200                 205

Phe Leu Gly Asp Lys Asp Val Lys Glu Lys Val Glu Ser Val Thr Pro
210                 215                 220

Leu Arg Arg Val Gly Glu Ala Asn Glu Val Ser Ser Leu Val Ala Phe
225                 230                 235                 240

Leu Cys Leu Pro Ala Ala Ser Tyr Ile Thr Gly Gln Thr Ile Cys Val
                245                 250                 255

Asp Gly Gly Phe Thr Ile Asn Gly Phe Ser Leu Pro
            260                 265
```

<210> SEQ ID NO 13
<211> LENGTH: 935
<212> TYPE: DNA
<213> ORGANISM: Arabidopsis thaliana

<400> SEQUENCE: 13

```
aaagagagaa atggctggag cagagcaaag ccagagatgg agccttaagg ccaagaccgt      60
acttgtaacc ggtggaacaa aaggcatcgg catgctata gtagaggaat ttgcaggatt     120
tggagcagta atacatactt gtgctagaaa cgaatatgag cttaacgagt gtttaagcaa    180
atggcaaaag aagggttttc aagtcactgg ttcggtctgt gacgcatctt tgagaccaga    240
gagagaaaag ctaatgcaga ctgtgtcttc aatgtttggt ggaaagctcg atatcctcat    300
aaacaatttg ggagcgattc ggtcaaaacc aacgctggat tacacagcag aagatttctc    360
gtttcatatt tcgacaaact tagaatctgc ttatcatctg agccagcttg cgcatcctct    420
gcttaaggct tcaggatgtg gaacataat tttcatgtcc tctattgctg gagttgtatc    480
tgctagtgtc ggctccatct actctgcaac gaaaggggca ttgaatcagc tagcaaggaa    540
cttggcatgt gagtgggcta gtgatggcat tagggctaat gctgtggctc ctgcagtcat    600
cgcaactcct ttggctgaag ctgtgtatga tgatgagttc aagaaagtgg tgatatcaag    660
aaagccgttg gggcgtttcg gggagcctga agaagtgtcc tcgcttgtgg ctttcctatg    720
tatgcctgca gcttcttata taactggtca aaccatttgt gtcgatggag gtctcactgt    780
caatggcttc tcctatcagc cacaaggtta aaatccaata tccaaaaaca aacacatttt    840
caacttcatt actttgaaca ttgtcatctt gggctaagcc cggtttggaa gtatggattc    900
tggccgtaac actttagaaa ataaaaggaa acttc                               935
```

<210> SEQ ID NO 14
<211> LENGTH: 266
<212> TYPE: PRT
<213> ORGANISM: Arabidopsis thaliana

<400> SEQUENCE: 14

```
Met Ala Gly Ala Glu Gln Ser Gln Arg Trp Ser Leu Lys Ala Lys Thr
1               5                   10                  15

Val Leu Val Thr Gly Gly Thr Lys Gly Ile Gly His Ala Ile Val Glu
                20                  25                  30

Glu Phe Ala Gly Phe Gly Ala Val Ile His Thr Cys Ala Arg Asn Glu
            35                  40                  45
```

```
Tyr Glu Leu Asn Glu Cys Leu Ser Lys Trp Gln Lys Lys Gly Phe Gln
        50                  55                  60
Val Thr Gly Ser Val Cys Asp Ala Ser Leu Arg Pro Glu Arg Glu Lys
 65                  70                  75                  80
Leu Met Gln Thr Val Ser Ser Met Phe Gly Gly Lys Leu Asp Ile Leu
                85                  90                  95
Ile Asn Asn Leu Gly Ala Ile Arg Ser Lys Pro Thr Leu Asp Tyr Thr
            100                 105                 110
Ala Glu Asp Phe Ser Phe His Ile Ser Thr Asn Leu Glu Ser Ala Tyr
        115                 120                 125
His Leu Ser Gln Leu Ala His Pro Leu Leu Lys Ala Ser Gly Cys Gly
130                 135                 140
Asn Ile Ile Phe Met Ser Ser Ile Ala Gly Val Val Ser Ala Ser Val
145                 150                 155                 160
Gly Ser Ile Tyr Ser Ala Thr Lys Gly Ala Leu Asn Gln Leu Ala Arg
                165                 170                 175
Asn Leu Ala Cys Glu Trp Ala Ser Asp Gly Ile Arg Ala Asn Ala Val
            180                 185                 190
Ala Pro Ala Val Ile Ala Thr Pro Leu Ala Glu Ala Val Tyr Asp Asp
        195                 200                 205
Glu Phe Lys Lys Val Val Ile Ser Arg Lys Pro Leu Gly Arg Phe Gly
210                 215                 220
Glu Pro Glu Glu Val Ser Ser Leu Val Ala Phe Leu Cys Met Pro Ala
225                 230                 235                 240
Ala Ser Tyr Ile Thr Gly Gln Thr Ile Cys Val Asp Gly Gly Leu Thr
                245                 250                 255
Val Asn Gly Phe Ser Tyr Gln Pro Gln Gly
            260                 265

<210> SEQ ID NO 15
<211> LENGTH: 795
<212> TYPE: DNA
<213> ORGANISM: Arabidopsis thaliana

<400> SEQUENCE: 15
atggaaactg acaaaagatg gtctctcgcc gggaaaacag ctctggtaac cggcgggact      60
cgtggaatcg ggagagcagt tgtagaggaa ctagcaaaat ttggtgcaaa agttcatact     120
tgttcaagga accaggaaga gctaaatgca tgcttgaatg attggaaagc gaatggttta     180
gtcgtgtctg gttcggtttg tgatgcttcg gttagggatc agagggagaa gttgattcag     240
gaagcttctt ctgccttcag tgcaagctc aacatcctta taacaatgt ggaactaat       300 gtcaggaaac caacagttga atactcaagc gaggaatatg ccaaaatcat gtcgaccaac     360
ttagaatccg ctttccattt atctcaaatt gctcatcctc ttctaaaagc atctggtgtc     420
ggaagcattg tgttcatctc ctctgtagct ggcctggtgc atcttagcag tggatctatc     480
tatggtgcaa ctaaaggagc acttaatcag cttacaagaa atctagcttg cgagtgggca     540
agcgacaaca tcagaaccaa ttgcgtggcg ccatggtaca tcaagacctc acttgtggaa     600
acgctacttg agaagaaaga atttgtggag gctgtagttt caaggacccc acttgggcgc     660
gttggagaac cagaggaagt ctcatcgttg gttgcctttc tctgccttcc cgcatcatct     720
tatattaccg gacaggtcat atccgtcgat ggaggattca ctgtcaacgg ttttagctat     780
gctatgaagc cttaa                                                     795
```

<210> SEQ ID NO 16
<211> LENGTH: 264
<212> TYPE: PRT
<213> ORGANISM: Arabidopsis thaliana

<400> SEQUENCE: 16

Met Glu Thr Asp Lys Arg Trp Ser Leu Ala Gly Lys Thr Ala Leu Val
1               5                   10                  15

Thr Gly Gly Thr Arg Gly Ile Gly Arg Ala Val Val Glu Glu Leu Ala
            20                  25                  30

Lys Phe Gly Ala Lys Val His Thr Cys Ser Arg Asn Gln Glu Glu Leu
        35                  40                  45

Asn Ala Cys Leu Asn Asp Trp Lys Ala Asn Gly Leu Val Val Ser Gly
    50                  55                  60

Ser Val Cys Asp Ala Ser Val Arg Asp Gln Arg Glu Lys Leu Ile Gln
65                  70                  75                  80

Glu Ala Ser Ser Ala Phe Ser Gly Lys Leu Asn Ile Leu Ile Asn Asn
                85                  90                  95

Val Gly Thr Asn Val Arg Lys Pro Thr Val Glu Tyr Ser Ser Glu Glu
            100                 105                 110

Tyr Ala Lys Ile Met Ser Thr Asn Leu Glu Ser Ala Phe His Leu Ser
        115                 120                 125

Gln Ile Ala His Pro Leu Leu Lys Ala Ser Gly Val Gly Ser Ile Val
    130                 135                 140

Phe Ile Ser Ser Val Ala Gly Leu Val His Leu Ser Ser Gly Ser Ile
145                 150                 155                 160

Tyr Gly Ala Thr Lys Gly Ala Leu Asn Gln Leu Thr Arg Asn Leu Ala
                165                 170                 175

Cys Glu Trp Ala Ser Asp Asn Ile Arg Thr Asn Cys Val Ala Pro Trp
            180                 185                 190

Tyr Ile Lys Thr Ser Leu Val Glu Thr Leu Glu Lys Lys Glu Phe
        195                 200                 205

Val Glu Ala Val Val Ser Arg Thr Pro Leu Gly Arg Val Gly Glu Pro
    210                 215                 220

Glu Glu Val Ser Ser Leu Val Ala Phe Leu Cys Leu Pro Ala Ser Ser
225                 230                 235                 240

Tyr Ile Thr Gly Gln Val Ile Ser Val Asp Gly Gly Phe Thr Val Asn
                245                 250                 255

Gly Phe Ser Tyr Ala Met Lys Pro
            260

<210> SEQ ID NO 17
<211> LENGTH: 789
<212> TYPE: DNA
<213> ORGANISM: Arabidopsis thaliana

<400> SEQUENCE: 17
atggataaaa gatggagtct tcagggtatg accgctcttg taactggtgg agccagcgga      60
atcgggcatg ctatagtaga ggagctagcc ggtcttggag ctagaatcta tgtatgcgat     120
atatctgaaa cactgctcaa tcaaagttta agtgaatggg aaaagaaagg gtttcaagta     180
agtggttcaa tatgtgatgt atcctctcat tccgagaggg aaacacttat gcaaacagtc     240
tcaaagatgt tcgatggcaa gctgaacatt cttgtgaaca atgttggcgt agttaatcca     300
aagccaacaa tagaatatgt ggcagccgat ttctcgttca gtatttcaac aaacttggaa     360
tctgcttatc accttagcca actttcacat cctctcctaa aagcttcaga atttggaagc     420

```
atcatcttca tttcttctgt tggaggggtt gtgtcaatgg agtgtggatc tatctatagt    480
ttaacgaaag gagctttgaa tcaactagca aaaactttgg catgtgaatg ggcaagagat    540
ggcataagag ccaactctgt tgctcctaat tttatctaca ctgctatggc tcaaccttt     600 ttcaaagacg ccgattacga aagagtttg gttagtagaa ctccacttgg tcgcgctgga    660
gagccaaatg aggtttcatc acttgtggct tttctgtgtc tacctgcagc ttcatatatt    720
actggtcaga ccatttgtgt tgatggaggt ctcactgtca atggttttctc ctataagcca    780 caggcttga                                                             789
```

<210> SEQ ID NO 18
<211> LENGTH: 262
<212> TYPE: PRT
<213> ORGANISM: Arabidopsis thaliana

<400> SEQUENCE: 18

Met Asp Lys Arg Trp Ser Leu Gln Gly Met Thr Ala Leu Val Thr Gly
1               5                   10                  15

Gly Ala Ser Gly Ile Gly His Ala Ile Val Glu Glu Leu Ala Gly Leu
            20                  25                  30

Gly Ala Arg Ile Tyr Val Cys Asp Ile Ser Glu Thr Leu Leu Asn Gln
        35                  40                  45

Ser Leu Ser Glu Trp Glu Lys Lys Gly Phe Gln Val Ser Gly Ser Ile
    50                  55                  60

Cys Asp Val Ser Ser His Ser Glu Arg Glu Thr Leu Met Gln Thr Val
65                  70                  75                  80

Ser Lys Met Phe Asp Gly Lys Leu Asn Ile Leu Val Asn Asn Val Gly
                85                  90                  95

Val Val Asn Pro Lys Pro Thr Ile Glu Tyr Val Ala Ala Asp Phe Ser
            100                 105                 110

Phe Ser Ile Ser Thr Asn Leu Glu Ser Ala Tyr His Leu Ser Gln Leu
        115                 120                 125

Ser His Pro Leu Leu Lys Ala Ser Glu Phe Gly Ser Ile Ile Phe Ile
    130                 135                 140

Ser Ser Val Gly Gly Val Val Ser Met Glu Cys Gly Ser Ile Tyr Ser
145                 150                 155                 160

Leu Thr Lys Gly Ala Leu Asn Gln Leu Ala Lys Thr Leu Ala Cys Glu
                165                 170                 175

Trp Ala Arg Asp Gly Ile Arg Ala Asn Ser Val Ala Pro Asn Phe Ile
            180                 185                 190

Tyr Thr Ala Met Ala Gln Pro Phe Phe Lys Asp Ala Asp Tyr Glu Lys
        195                 200                 205

Ser Leu Val Ser Arg Thr Pro Leu Gly Arg Ala Gly Glu Pro Asn Glu
    210                 215                 220

Val Ser Ser Leu Val Ala Phe Leu Cys Leu Pro Ala Ala Ser Tyr Ile
225                 230                 235                 240

Thr Gly Gln Thr Ile Cys Val Asp Gly Gly Leu Thr Val Asn Gly Phe
                245                 250                 255

Ser Tyr Lys Pro Gln Ala
            260

<210> SEQ ID NO 19
<211> LENGTH: 789
<212> TYPE: DNA
<213> ORGANISM: Arabidopsis thaliana

<400> SEQUENCE: 19

```
atggacaaaa gatggagtct caaaggtatg actgctcttg tgaccggtgg agccagtgga      60
atcggttatg ccatagtaga agagttggct ggttttggag ctagaatcca tgtatgtgac     120
atctctgaag ctaagctcaa tcaaagttta agcgaatggg aaaagaaagg ttttcaagta     180
agtggctcag tttgtgatgt agcctctcgt cccgagagag aagaactgat gcaaaccgtc     240
tcctcgcagt tcgatggcaa actcaacatt cttgtaagca atgtgggcgt aatccgctca     300
aagccaacaa cagaatatac cgaagacgat ttcgcttttc atatatcatc aaacgtggaa     360
gctgcttacc attttagcca gctttcacat cctctcctaa aggcttcagg ctatggaagc     420
atcatctttg tttcctctat tgcaggggtt atatcttttg acgctggatc catttatggt     480
ctaacaaaag gagctttgat tcagctagct aaaaatttgg catgtgaatg ggcaaaagac     540
ggcataagag ccaacgctgt tgcgcctaat gtcatcaata ctcctctgtc tcaatcttat     600
cttgaggacg tcagtttcaa gaaggcattg ttgagtagga ctccacttgg tcgtgttgga     660
gagccaaatg aagttgcatc actagtggcc ttcttgtgtc tacctgcagc ttcttatatt     720
actggtcaga ctatttgtgt tgatggaggt ctcaccgtta atggcttctc ctatcagcca     780
gaggtttga                                                              789
```

<210> SEQ ID NO 20
<211> LENGTH: 262
<212> TYPE: PRT
<213> ORGANISM: Arabidopsis thaliana

<400> SEQUENCE: 20

```
Met Asp Lys Arg Trp Ser Leu Lys Gly Met Thr Ala Leu Val Thr Gly
1               5                   10                  15
Gly Ala Ser Gly Ile Gly Tyr Ala Ile Val Glu Glu Leu Ala Gly Phe
            20                  25                  30
Gly Ala Arg Ile His Val Cys Asp Ile Ser Glu Ala Lys Leu Asn Gln
        35                  40                  45
Ser Leu Ser Glu Trp Glu Lys Lys Gly Phe Gln Val Ser Gly Ser Val
    50                  55                  60
Cys Asp Val Ala Ser Arg Pro Glu Arg Glu Glu Leu Met Gln Thr Val
65                  70                  75                  80
Ser Ser Gln Phe Asp Gly Lys Leu Asn Ile Leu Val Ser Asn Val Gly
                85                  90                  95
Val Ile Arg Ser Lys Pro Thr Thr Glu Tyr Thr Glu Asp Asp Phe Ala
            100                 105                 110
Phe His Ile Ser Ser Asn Val Glu Ala Ala Tyr His Phe Ser Gln Leu
        115                 120                 125
Ser His Pro Leu Leu Lys Ala Ser Gly Tyr Gly Ser Ile Ile Phe Val
    130                 135                 140
Ser Ser Ile Ala Gly Val Ile Ser Phe Asp Ala Gly Ser Ile Tyr Gly
145                 150                 155                 160
Leu Thr Lys Gly Ala Leu Ile Gln Leu Ala Lys Asn Leu Ala Cys Glu
                165                 170                 175
Trp Ala Lys Asp Gly Ile Arg Ala Asn Ala Val Ala Pro Asn Val Ile
            180                 185                 190
Asn Thr Pro Leu Ser Gln Ser Tyr Leu Glu Asp Val Ser Phe Lys Lys
        195                 200                 205
Ala Leu Leu Ser Arg Thr Pro Leu Gly Arg Val Gly Glu Pro Asn Glu
    210                 215                 220
Val Ala Ser Leu Val Ala Phe Leu Cys Leu Pro Ala Ala Ser Tyr Ile
```

```
                225                 230                 235                 240
Thr Gly Gln Thr Ile Cys Val Asp Gly Gly Leu Thr Val Asn Gly Phe
                    245                 250                 255
Ser Tyr Gln Pro Glu Val
            260

<210> SEQ ID NO 21
<211> LENGTH: 810
<212> TYPE: DNA
<213> ORGANISM: Arabidopsis thaliana

<400> SEQUENCE: 21
atggtcacta gaaaaatgga caaaagatta tggagtcttc aaggtatgac tgctcttgtg      60
accggtgcag ccagcggaat cggttatgcc atagtagaag agttagctgg ttttggagct     120
aaaatccaca tatgtgacat atccaaaact ttgctcaatc aaagtttaag cgaatgggaa     180
aataaagggt ttcaagtgag tggttcagta tgtgatgtaa cctctcatcc tgagagagaa     240
aaactgatgc aaaccgtctc ctcgattttc gatggcaaac tcaacattct tgtaaataac     300 gtggggggtac ttcgcggaaa gccaacaaca gaatatgtgg cagacgattt cacttttcat     360
atatcaacta acttggaagc tgcttaccat ttttgtcaac tttcacatcc tctcttaaag     420
gcttcaggct atggaagcat tgtattcctt tcctctgttg ctggggttgt atcactaatt     480
gactgtggat ccatttatgg tctaacaaaa ggagctctaa atcaattagc tagaaacttg     540
gcatgtgaat gggcaaaaga cggcataaga gccaatgctg ttgcacctaa tgttgtcaag     600
actgctcagt ctcaatcgtt tcttgaagac gtcagtaaaa aggagggatt gttgagtaga     660
actccacttg gccgtgttgg agagccgaat gaagtttcat cactagtggt cttcttgtgt     720
ctacctgcag cttcttatat cacaggtcaa accatttgtg ttgatggagg tctcacggtt     780
aacggtttct cctatcaacc acatgcttga                                      810

<210> SEQ ID NO 22
<211> LENGTH: 269
<212> TYPE: PRT
<213> ORGANISM: Arabidopsis thaliana

<400> SEQUENCE: 22

Met Val Thr Arg Lys Met Asp Lys Arg Leu Trp Ser Leu Gln Gly Met
1               5                   10                  15

Thr Ala Leu Val Thr Gly Ala Ala Ser Gly Ile Gly Tyr Ala Ile Val
            20                  25                  30

Glu Glu Leu Ala Gly Phe Gly Ala Lys Ile His Ile Cys Asp Ile Ser
        35                  40                  45

Lys Thr Leu Leu Asn Gln Ser Leu Ser Glu Trp Glu Asn Lys Gly Phe
    50                  55                  60

Gln Val Ser Gly Ser Val Cys Asp Val Thr Ser His Pro Glu Arg Glu
65                  70                  75                  80

Lys Leu Met Gln Thr Val Ser Ser Ile Phe Asp Gly Lys Leu Asn Ile
                85                  90                  95

Leu Val Asn Asn Val Gly Val Leu Arg Gly Lys Pro Thr Thr Glu Tyr
            100                 105                 110

Val Ala Asp Asp Phe Thr Phe His Ile Ser Thr Asn Leu Glu Ala Ala
        115                 120                 125

Tyr His Phe Cys Gln Leu Ser His Pro Leu Leu Lys Ala Ser Gly Tyr
    130                 135                 140

Gly Ser Ile Val Phe Leu Ser Ser Val Ala Gly Val Val Ser Leu Ile
```

```
                        145                 150                 155                 160

Asp Cys Gly Ser Ile Tyr Gly Leu Thr Lys Gly Ala Leu Asn Gln Leu
                    165                 170                 175

Ala Arg Asn Leu Ala Cys Glu Trp Ala Lys Asp Gly Ile Arg Ala Asn
                180                 185                 190

Ala Val Ala Pro Asn Val Val Lys Thr Ala Gln Ser Gln Ser Phe Leu
            195                 200                 205

Glu Asp Val Ser Lys Lys Glu Gly Leu Leu Ser Arg Thr Pro Leu Gly
        210                 215                 220

Arg Val Gly Glu Pro Asn Glu Val Ser Ser Leu Val Val Phe Leu Cys
225                 230                 235                 240

Leu Pro Ala Ala Ser Tyr Ile Thr Gly Gln Thr Ile Cys Val Asp Gly
                245                 250                 255

Gly Leu Thr Val Asn Gly Phe Ser Tyr Gln Pro His Ala
            260                 265

<210> SEQ ID NO 23
<211> LENGTH: 969
<212> TYPE: DNA
<213> ORGANISM: Arabidopsis thaliana

<400> SEQUENCE: 23
atggtgcttg acatggcttc tcacttgtac acaaatccac ctcaaaacct tcactttatt       60
tcttcttctt cttcccttaa acctcattta tgcctctctt tcaaacgcat aaaccctaaa      120
cacaaatcct cttcctcttc cgtcttcgtc ccttacgcat acagagttc cattgccatt       180 acctccaagg aaagatggtc tctcaatgga atgtctgctc ttgtcaccgg cggcactcgt      240
ggaattgggc gtgcgattgt ggaggaattg gctggtcttg agcagaagt tcacacttgc       300 gctcggaatg agtacgagct ggagaattgt ttgagtgatt ggaaccgttc tggttttcga      360
gttgctggat ccgtttgcga tgtctctgat cgatctcaga gagaggcttt gatggagacc      420
gtgtcatctg tgtttgaagg gaagcttcat atccttgtaa acaatgttgg gacgaacatt      480
aggaaaccaa tggtagagtt tactgctgga gaatttttcga ctctgatgtc tacgaatttc     540
gaatcggttt tccatttatg tcaacttgct tatccattgc ttagagaatc taaagctgga     600
agtgttgtgt tcatctcttc tgtttctggt tttgtttccc tcaagaatat gtcggtccaa     660
tcttcaacca aaggagcaat taatcaactt acgagaagtc tggcttgcga gtgggccaaa     720
gacaatataa ggatcaatgc tgttgccccg tggtatatca aaacatctat ggtggagcaa     780
gtccttagca acaaagagta cctagaagaa gtctactcag taactcctct tggtcgactt     840
ggcgaaccga gagaggtgtc ttctgcagtg gctttttat gcctacctgc atcatcatat     900
attacagggc agattctttg tgttgatggt ggaatgtcaa taaacggttt cttcccacga     960
catgattag                                                            969

<210> SEQ ID NO 24
<211> LENGTH: 322
<212> TYPE: PRT
<213> ORGANISM: Arabidopsis thaliana

<400> SEQUENCE: 24

Met Val Leu Asp Met Ala Ser His Leu Tyr Thr Asn Pro Pro Gln Asn
1               5                   10                  15

Leu His Phe Ile Ser Ser Ser Ser Leu Lys Pro His Leu Cys Leu
                20                  25                  30

Ser Phe Lys Arg Ile Asn Pro Lys His Lys Ser Ser Ser Ser Ser Val
```

```
                35                  40                  45
Phe Val Pro Tyr Ala Ser Gln Ser Ser Ile Ala Ile Thr Ser Lys Glu
 50                  55                  60

Arg Trp Ser Leu Asn Gly Met Ser Ala Leu Val Thr Gly Gly Thr Arg
 65                  70                  75                  80

Gly Ile Gly Arg Ala Ile Val Glu Glu Leu Ala Gly Leu Gly Ala Glu
                 85                  90                  95

Val His Thr Cys Ala Arg Asn Glu Tyr Glu Leu Glu Asn Cys Leu Ser
                100                 105                 110

Asp Trp Asn Arg Ser Gly Phe Arg Val Ala Gly Ser Val Cys Asp Val
            115                 120                 125

Ser Asp Arg Ser Gln Arg Glu Ala Leu Met Glu Thr Val Ser Ser Val
130                 135                 140

Phe Glu Gly Lys Leu His Ile Leu Val Asn Asn Val Gly Thr Asn Ile
145                 150                 155                 160

Arg Lys Pro Met Val Glu Phe Thr Ala Gly Glu Phe Ser Thr Leu Met
                165                 170                 175

Ser Thr Asn Phe Glu Ser Val Phe His Leu Cys Gln Leu Ala Tyr Pro
            180                 185                 190

Leu Leu Arg Glu Ser Lys Ala Gly Ser Val Val Phe Ile Ser Ser Val
        195                 200                 205

Ser Gly Phe Val Ser Leu Lys Asn Met Ser Val Gln Ser Ser Thr Lys
210                 215                 220

Gly Ala Ile Asn Gln Leu Thr Arg Ser Leu Ala Cys Glu Trp Ala Lys
225                 230                 235                 240

Asp Asn Ile Arg Ile Asn Ala Val Ala Pro Trp Tyr Ile Lys Thr Ser
                245                 250                 255

Met Val Glu Gln Val Leu Ser Asn Lys Glu Tyr Leu Glu Glu Val Tyr
            260                 265                 270

Ser Val Thr Pro Leu Gly Arg Leu Gly Glu Pro Arg Glu Val Ser Ser
        275                 280                 285

Ala Val Ala Phe Leu Cys Leu Pro Ala Ser Ser Tyr Ile Thr Gly Gln
290                 295                 300

Ile Leu Cys Val Asp Gly Gly Met Ser Ile Asn Gly Phe Phe Pro Arg
305                 310                 315                 320

His Asp

<210> SEQ ID NO 25
<211> LENGTH: 1003
<212> TYPE: DNA
<213> ORGANISM: Arabidopsis thaliana

<400> SEQUENCE: 25
gtccggattc ccgggtcgac ccccgcgccc cattcattgt atataatctt atggcatttc      60
tggtcattta gtctcaagca aaatggacaa gagatggagt ctacaaggta tgactgctct     120
tgtaaccggt gcagccagtg gaatcgggta tgccatagta gaggagttag caagttttgg     180
agctataatc catatatgtg acatctctga aactcttctc agtcaaagtt taagtgaatg     240
ggaaaagaaa gggtttcaag tgagtggttc agtctgtgat gtagcctctc ggcccgagag     300
agaaaaactg atgcaaaccg tctcctcgct gttcgatggc aaactcaaca ttcttgtaaa     360
caatgttggt gtaatacgtg aaagccaac aacagaatat gtggcagagg atttctctta     420
ccacatctca acaaacttgg aaccagcttt ccatttagc cagcttttac atcctctttct     480 aaaggcttca ggctttggaa gcatcgtctt tatgtcctct gctacagggg ttgtatcagt     540
```

-continued

```
tcaatgtgga tccatttata gtctaactaa aggagctttg aaccagttaa ctagaaattt      600
agcatgtgaa tgggcaaaag acggcataag agccaatgct gttgcgccta atgttgtcaa      660
gactcctttg tctcaatctt atctcgagga cgtcggtttc aaggaggcat tgttcagtag      720
aactccactt ggtcgcgctg agagccgaa tgaagttgca tcactagtgg ccttcttgtg       780
tctacctgca gcttcttata ttactggtca gactatttgt gttgatggag gtctcaccgt      840
taatggcttc tcctatcagc cagaggtttg agtatggtca tgtctcgttc tttttgtttg      900
tctagaattt tcagtgttct ctcaaataaa atatttcaaa ctatgagtat atgaataaaa      960
aaataaatat atcataatta cattatggat atacttacaa tgt                       1003
```

<210> SEQ ID NO 26
<211> LENGTH: 262
<212> TYPE: PRT
<213> ORGANISM: Arabidopsis thaliana

<400> SEQUENCE: 26

```
Met Asp Lys Arg Trp Ser Leu Gln Gly Met Thr Ala Leu Val Thr Gly
1               5                   10                  15

Ala Ala Ser Gly Ile Gly Tyr Ala Ile Val Glu Glu Leu Ala Ser Phe
            20                  25                  30

Gly Ala Ile Ile His Ile Cys Asp Ile Ser Glu Thr Leu Leu Ser Gln
        35                  40                  45

Ser Leu Ser Glu Trp Glu Lys Lys Gly Phe Gln Val Ser Gly Ser Val
    50                  55                  60

Cys Asp Val Ala Ser Arg Pro Glu Arg Glu Lys Leu Met Gln Thr Val
65                  70                  75                  80

Ser Ser Leu Phe Asp Gly Lys Leu Asn Ile Leu Val Asn Asn Val Gly
                85                  90                  95

Val Ile Arg Gly Lys Pro Thr Thr Glu Tyr Val Ala Glu Asp Phe Ser
            100                 105                 110

Tyr His Ile Ser Thr Asn Leu Glu Pro Ala Phe His Phe Ser Gln Leu
        115                 120                 125

Ser His Pro Leu Leu Lys Ala Ser Gly Phe Gly Ser Ile Val Phe Met
    130                 135                 140

Ser Ser Ala Thr Gly Val Val Ser Val Gln Cys Gly Ser Ile Tyr Ser
145                 150                 155                 160

Leu Thr Lys Gly Ala Leu Asn Gln Leu Thr Arg Asn Leu Ala Cys Glu
                165                 170                 175

Trp Ala Lys Asp Gly Ile Arg Ala Asn Ala Val Ala Pro Asn Val Val
            180                 185                 190

Lys Thr Pro Leu Ser Gln Ser Tyr Leu Glu Asp Val Gly Phe Lys Glu
        195                 200                 205

Ala Leu Phe Ser Arg Thr Pro Leu Gly Arg Ala Gly Glu Pro Asn Glu
    210                 215                 220

Val Ala Ser Leu Val Ala Phe Leu Cys Leu Pro Ala Ala Ser Tyr Ile
225                 230                 235                 240

Thr Gly Gln Thr Ile Cys Val Asp Gly Gly Leu Thr Val Asn Gly Phe
                245                 250                 255

Ser Tyr Gln Pro Glu Val
            260
```

<210> SEQ ID NO 27
<211> LENGTH: 1040
<212> TYPE: DNA

<213> ORGANISM: Arabidopsis thaliana

<400> SEQUENCE: 27

```
cggacgcgtg gcggacgcg tgggcggacg cgtgggcgga cgcgtggccc gccgccgggg      60
acgcgtgcct tggttctgt ggttcataat cagaattggc taatacaggg gaaagcttga     120
gagacaaacc tatatggagt cttgtaggca tgaccgctct tgtcaccggt ggctcaaaag    180
gcatcggaca agctgtggtt gacgaactag ctacgttagg ggcaagaatc cacacatgtg    240
ccagagacga aactcagctt caagaaagct tacatacgtg gcaagcagaa gggtttcagg    300
ttaccacttc tgtctgcgac gtctcttctc gtgataaacg agagaagctc atggaaaccg    360
tttccactat cttcgaccga aacctcaaca tacttgtcac caatgtggca acgtgtagag    420
tcagtcccgc cctacaacat acagccgaag atttctcatt tacaatggca acgaatctcg    480
agtcagcttt tcatctctcg cagctcgcgc atcctttgtt gaaagcttct ggttcaggga    540
gcatcgtgct catctcctcc gtatctggag ttgtacatgt caatggtgca tccatatatg    600
gagtatctaa aggagctatg aatcagctag gaagaaactt agcgtgcgag tgggcaagtg    660
acaacataag gactaactct gtgtgtccat ggttcataga aactccttta gttaccgaaa    720
gtcttagtaa tgaggagttt agaaaagaag tggagagtag ccccccaatg ggacgtgttg    780
gagaagtaaa tgaagtatca tcgcttgtgg catttctttg tcttcctgca gcttcttata    840
ttacaggtca aaccatttgt gttgatggag gtttccctgt taatggtttt tctttcaagc    900
ctctgcctta agacgtcgat tgttttcatt ttacgttact ccccccccatt tacaatttgt    960
ttagatatgt aaacataaac ccaattaccc aaacaaacaa aaaaaattgg cgtttggaat   1020
gtaatccaac tctccccaat                                              1040
```

<210> SEQ ID NO 28
<211> LENGTH: 253
<212> TYPE: PRT
<213> ORGANISM: Arabidopsis thaliana

<400> SEQUENCE: 28

```
Met Thr Ala Leu Val Thr Gly Gly Ser Lys Gly Ile Gly Gln Ala Val
1               5                   10                  15

Val Asp Glu Leu Ala Thr Leu Gly Ala Arg Ile His Thr Cys Ala Arg
            20                  25                  30

Asp Glu Thr Gln Leu Gln Glu Ser Leu His Thr Trp Gln Ala Glu Gly
        35                  40                  45

Phe Gln Val Thr Thr Ser Val Cys Asp Val Ser Arg Asp Lys Arg
    50                  55                  60

Glu Lys Leu Met Glu Thr Val Ser Thr Ile Phe Asp Arg Asn Leu Asn
65                  70                  75                  80

Ile Leu Val Thr Asn Val Ala Thr Cys Arg Val Ser Pro Ala Leu Gln
                85                  90                  95

His Thr Ala Glu Asp Phe Ser Phe Thr Met Ala Thr Asn Leu Glu Ser
            100                 105                 110

Ala Phe His Leu Ser Gln Leu Ala His Pro Leu Leu Lys Ala Ser Gly
        115                 120                 125

Ser Gly Ser Ile Val Leu Ile Ser Ser Val Ser Gly Val Val His Val
    130                 135                 140

Asn Gly Ala Ser Ile Tyr Gly Val Ser Lys Gly Ala Met Asn Gln Leu
145                 150                 155                 160

Gly Arg Asn Leu Ala Cys Glu Trp Ala Ser Asp Asn Ile Arg Thr Asn
                165                 170                 175
```

Ser Val Cys Pro Trp Phe Ile Glu Thr Pro Leu Val Thr Glu Ser Leu
            180                 185                 190

Ser Asn Glu Glu Phe Arg Lys Glu Val Glu Ser Ser Pro Pro Met Gly
            195                 200                 205

Arg Val Gly Glu Val Asn Glu Val Ser Ser Leu Val Ala Phe Leu Cys
            210                 215                 220

Leu Pro Ala Ala Ser Tyr Ile Thr Gly Gln Thr Ile Cys Val Asp Gly
225                 230                 235                 240

Gly Phe Pro Val Asn Gly Phe Ser Phe Lys Pro Leu Pro
                245                 250

<210> SEQ ID NO 29
<211> LENGTH: 970
<212> TYPE: DNA
<213> ORGANISM: Arabidopsis thaliana

<400> SEQUENCE: 29
agcccacgcg tccgtacggt gcgagaagac gacagaaggg gcactagaaa aatggacaaa      60
agattatgga gtcttcaagg tatgactgct cttgtgaccg gtgcagccag cggaatcggt     120
tatgccatag tagaagagtt agctggtttt ggagctagaa tccacatatg tgacatatcc     180
aaaactttgc tcaatcaaag tttaagcgaa tgggaaaata agggtttca agtgagtggt      240
tcagtatgtg atgtaaccct ctcatcctgag agagaaaaac tgatgcaaac cgtctcctcg     300
attttcgatg gcaaactcaa cattcttgta ataacgtggg gggtacttcg cggaaagcca     360
acaacagaat atgtggcaga cgatttcact tttcatatat caactaactt ggaagctgct     420
taccactttt gtcaactttc acatcctctc ttaaagactt caggctatgg aagcatcgtg     480
ttcctttcct ctgtttctgg ggttgtgtca ataacttgcc tgggatcact ttatggtcta     540
ccaaaaggag ctctaaatca gctagctaga aatttggcat gtgaatggcc aaaagacggc     600
ataagagcca atgcggttgc acctaatgtt gtcaagactg ctcagtctca attctttctt     660
caagacgtca gtaaaaagga gggattgttt agtagaactc cacttggtcg gtctggagag     720
ccgaatgaag tagcatcact agtggtcttt ttgtgtcttc ctgcagcttc ttatatcaca     780
ggtcaaaacca tttgtattga tggaggcctc acggtttacg gtttctcctc tcaaccacag     840
gcttgaaaat ggtcttgtcg tttcttgtct gtttaaatat tctctcccta ataaaatctc     900
tcatcacgct atgagtttat gtcccttgta caaaaacaca caatgtcaaa ttgttgctct     960
ttagtcttgt                                                             970

<210> SEQ ID NO 30
<211> LENGTH: 264
<212> TYPE: PRT
<213> ORGANISM: Arabidopsis thaliana

<400> SEQUENCE: 30

Met Asp Lys Arg Leu Trp Ser Leu Gln Gly Met Thr Ala Leu Val Thr
1               5                   10                  15

Gly Ala Ala Ser Gly Ile Gly Tyr Ala Ile Val Glu Glu Leu Ala Gly
            20                  25                  30

Phe Gly Ala Arg Ile His Ile Cys Asp Ile Ser Lys Thr Leu Leu Asn
            35                  40                  45

Gln Ser Leu Ser Glu Trp Glu Asn Lys Gly Phe Gln Val Ser Gly Ser
        50                  55                  60

Val Cys Asp Val Thr Ser His Pro Glu Arg Glu Lys Leu Met Gln Thr
65                  70                  75                  80

```
Val Ser Ser Ile Phe Asp Gly Lys Leu Asn Ile Leu Val Asn Val
                85                  90                  95
Gly Val Leu Arg Gly Lys Pro Thr Thr Glu Tyr Val Ala Asp Asp Phe
            100                 105                 110
Thr Phe His Ile Ser Thr Asn Leu Glu Ala Ala Tyr His Phe Cys Gln
            115                 120                 125
Leu Ser His Pro Leu Leu Lys Thr Ser Gly Tyr Gly Ser Ile Val Phe
        130                 135                 140
Leu Ser Ser Val Ser Gly Val Val Ser Ile Thr Cys Leu Gly Ser Leu
145                 150                 155                 160
Tyr Gly Leu Pro Lys Gly Ala Leu Asn Gln Leu Ala Arg Asn Leu Ala
                165                 170                 175
Cys Glu Trp Pro Lys Asp Gly Ile Arg Ala Asn Ala Val Ala Pro Asn
            180                 185                 190
Val Val Lys Thr Ala Gln Ser Gln Phe Phe Leu Gln Asp Val Ser Lys
            195                 200                 205
Lys Glu Gly Leu Phe Ser Arg Thr Pro Leu Gly Arg Ser Gly Glu Pro
        210                 215                 220
Asn Glu Val Ala Ser Leu Val Val Phe Leu Cys Leu Pro Ala Ala Ser
225                 230                 235                 240
Tyr Ile Thr Gly Gln Thr Ile Cys Ile Asp Gly Gly Leu Thr Val Tyr
                245                 250                 255
Gly Phe Ser Ser Gln Pro Gln Ala
            260

<210> SEQ ID NO 31
<211> LENGTH: 943
<212> TYPE: DNA
<213> ORGANISM: Arabidopsis thaliana

<400> SEQUENCE: 31
ccggaattcc ttggtcgacc cacgcgtccg catacaagga ctatggataa aggtggagt      60
ctccaaggtt tgactgctct tgtgaccggt ggagccagcg gaatcggtca tgctatagta    120
gaagaactcg ccggttttgg ggccaaaatc catgtgtgtg acatatcgaa aactctgctc    180
aatcaaagtt tatccgaatg ggagaagaaa gggtttcaag tgagtggttc agtctgcgat    240
gcatccaatc gtctcgaaag agaaacactt atgcaaactg tcaccacaat atttgatggc    300
aagcttaaca ttcttgtgaa caatgttggc acaattcgca caaagccaac aatagaatat    360
gaggcagaag atttttcgtt ccttatttca acaaacttgg aatctgctta tcatctaagc    420
caactttcac atccactcct aaaggcttca ggcaacggaa ttattacttt tatttcctct    480
gctgcaggga tcgtatcatt tgatgctgca tccatttatg gcctaacgaa aggagctttg    540
aatcagctag cacgaaattt ggcgtgtgaa tgggcaaaag acggcattcg agccaacgcg    600
gttgcgccta attttatcac cactgctctg gctaaacctt ttctcgaaga cgctggtttt    660
aacgagattt tgtcgagtag aactccactt ggtcgcgctg agaaccaag agaggttgcc    720
tcacttgtgg cttttctgtg tctacctgct gcttcatata ttactggtca gaccatttgt    780
gttgatggag gtctcactgt taatggcttc tcatatcagc cataggcttg agccatgtct    840
tgtcttgtct tgtgtgttgt ggagtatggt catatggtca gtatctccat aatctaaatc    900
catagatatg tgagttgtgg agtagacaca atttttcaat aat                      943

<210> SEQ ID NO 32
<211> LENGTH: 260
```

```
<212> TYPE: PRT
<213> ORGANISM: Arabidopsis thaliana

<400> SEQUENCE: 32

Met Asp Lys Arg Trp Ser Leu Gln Gly Leu Thr Ala Leu Val Thr Gly
1               5                   10                  15
Gly Ala Ser Gly Ile Gly His Ala Ile Val Glu Leu Ala Gly Phe
            20                  25                  30
Gly Ala Lys Ile His Val Cys Asp Ile Ser Lys Thr Leu Leu Asn Gln
        35                  40                  45
Ser Leu Ser Glu Trp Glu Lys Lys Gly Phe Gln Val Ser Gly Ser Val
    50                  55                  60
Cys Asp Ala Ser Asn Arg Leu Glu Arg Glu Thr Leu Met Gln Thr Val
65                  70                  75                  80
Thr Thr Ile Phe Asp Gly Lys Leu Asn Ile Leu Val Asn Asn Val Gly
                85                  90                  95
Thr Ile Arg Thr Lys Pro Thr Ile Glu Tyr Glu Ala Glu Asp Phe Ser
            100                 105                 110
Phe Leu Ile Ser Thr Asn Leu Glu Ser Ala Tyr His Leu Ser Gln Leu
        115                 120                 125
Ser His Pro Leu Leu Lys Ala Ser Gly Asn Gly Ile Ile Thr Phe Ile
    130                 135                 140
Ser Ser Ala Ala Gly Ile Val Ser Phe Asp Ala Ala Ser Ile Tyr Gly
145                 150                 155                 160
Leu Thr Lys Gly Ala Leu Asn Gln Leu Ala Arg Asn Leu Ala Cys Glu
                165                 170                 175
Trp Ala Lys Asp Gly Ile Arg Ala Asn Ala Val Ala Pro Asn Phe Ile
            180                 185                 190
Thr Thr Ala Leu Ala Lys Pro Phe Leu Glu Asp Ala Gly Phe Asn Glu
        195                 200                 205
Ile Leu Ser Ser Arg Thr Pro Leu Gly Arg Ala Gly Glu Pro Arg Glu
    210                 215                 220
Val Ala Ser Leu Val Ala Phe Leu Cys Leu Pro Ala Ala Ser Tyr Ile
225                 230                 235                 240
Thr Gly Gln Thr Ile Cys Val Asp Gly Gly Leu Thr Val Asn Gly Phe
                245                 250                 255
Ser Tyr Gln Pro
            260

<210> SEQ ID NO 33
<211> LENGTH: 1002
<212> TYPE: DNA
<213> ORGANISM: Glycine max

<400> SEQUENCE: 33
aagcaaacaa caatggcgaa ccctgaaggc agtagcagag gctctagatg gtcccttaag      60
ggaaccactg ctctcgttac tggaggaacg cgtggaattg gcacgctgt ggtggaggaa      120 ctagcggagt ttggtgccac agtgtacact tgttcgagga tgaagaaga gctgaatgca      180 tgcttgaagg agtggaaaga aagggattt tcggtttctg ggttggtttg tgatgcgtct      240
tctccacccc atagagagaa cctcattcaa caagtggcct ctgctttcaa cggcaagctc      300
aacatacttg taaacaatgt tggaacaaat gtgaggaagc cgacaattga gtatacagcc      360
gaagaatatt caaaattgat ggcaactaac ttggactcca cataccattt gtgccaactt      420
gcatatcctc ttcttaaagc atctggaaat ggaagtattg tgtccatttc ctctgttgca      480
```

```
agtcagacaa gcgtaggttc tggagccatt tacgcagcaa ctaaagctgc tattgatcag    540
cttaccaaat attttgcttg tgaatgggca aaagacaata taaggagcaa cggtgttgca    600
ccctggtata ccataacttc acttgtggaa cctttgcttg cgaacaaaca gcttgttagt    660
gagataatat ctcgaacgcc gataaagcgg atggcagaaa cacatgaagt ttcatccttg    720
gtgactttcc tttgcctgcc agcagcatcc tacatcactg gacagattgt ttcagttgat    780
ggaggattca ctgctaatgg atttcaaccc agcatgagaa tttcttaaag caaaatggcc    840
atttttattg ttggattgtg tgaacaaagt ggtggccact tgagttttgg accatctatg    900
atcaacttgt tttgattggt caataaatta ttttagtatt ttagaaattt gcattgtcat    960
tttcaacggc tatcattgtg agatgatggg tgctcttgga ac                     1002
```

<210> SEQ ID NO 34
<211> LENGTH: 271
<212> TYPE: PRT
<213> ORGANISM: Glycine max

<400> SEQUENCE: 34

```
Met Ala Asn Pro Glu Gly Ser Ser Arg Gly Ser Arg Trp Ser Leu Lys
1               5                   10                  15

Gly Thr Thr Ala Leu Val Thr Gly Gly Thr Arg Gly Ile Gly His Ala
            20                  25                  30

Val Val Glu Glu Leu Ala Glu Phe Gly Ala Thr Val Tyr Thr Cys Ser
        35                  40                  45

Arg Asn Glu Glu Glu Leu Asn Ala Cys Leu Lys Glu Trp Lys Glu Lys
    50                  55                  60

Gly Phe Ser Val Ser Gly Leu Val Cys Asp Ala Ser Ser Pro Pro His
65                  70                  75                  80

Arg Glu Asn Leu Ile Gln Gln Val Ala Ser Ala Phe Asn Gly Lys Leu
                85                  90                  95

Asn Ile Leu Val Asn Asn Val Gly Thr Asn Val Arg Lys Pro Thr Ile
            100                 105                 110

Glu Tyr Thr Ala Glu Glu Tyr Ser Lys Leu Met Ala Thr Asn Leu Asp
        115                 120                 125

Ser Thr Tyr His Leu Cys Gln Leu Ala Tyr Pro Leu Leu Lys Ala Ser
    130                 135                 140

Gly Asn Gly Ser Ile Val Ser Ile Ser Ser Val Ala Ser Gln Thr Ser
145                 150                 155                 160

Val Gly Ser Gly Ala Ile Tyr Ala Ala Thr Lys Ala Ala Ile Asp Gln
                165                 170                 175

Leu Thr Lys Tyr Phe Ala Cys Glu Trp Ala Lys Asp Asn Ile Arg Ser
            180                 185                 190

Asn Gly Val Ala Pro Trp Tyr Thr Ile Thr Ser Leu Val Glu Pro Leu
        195                 200                 205

Leu Ala Asn Lys Gln Leu Val Ser Glu Ile Ile Ser Arg Thr Pro Ile
    210                 215                 220

Lys Arg Met Ala Glu Thr His Glu Val Ser Ser Leu Val Thr Phe Leu
225                 230                 235                 240

Cys Leu Pro Ala Ala Ser Tyr Ile Thr Gly Gln Ile Val Ser Val Asp
                245                 250                 255

Gly Gly Phe Thr Ala Asn Gly Phe Gln Pro Ser Met Arg Ile Ser
            260                 265                 270
```

<210> SEQ ID NO 35
<211> LENGTH: 1084

```
<212> TYPE: DNA
<213> ORGANISM: Glycine max

<400> SEQUENCE: 35
atggaaaggc gttttaaaaa aagagtggaa gatggcaatg gcaggaagca gcattaacag      60
aggagaaaga tggtctctca atggaatgac tgctcttgtc accggcggca ctcgtgggat     120
cgggcactcc atagtgagtg acttggctgc gtttggcgct gcagtgcaca cctgttccag     180
gacccaaaca gagctcaaca atgcttaca agagtggcag agtcaggggt ttcaggtaac     240
tgggtcgctc tgtgacgtgt cctcaccacc ccagagagag aagctcattc aggaagttgc     300
atccaccttc aatggcaagc ttaacatcta cgtgaacaat gttggaataa acattagaaa     360
gccaaccatt gagtacactg ctgaagaata ttcacagatt atgacagtta atttagactc     420
ctcattccat ctgtgccagc ttgcatatcc tcttctgaaa gcatctgaaa agggaagcat     480
tgtgttcatt tcatctgttg ctggtgtagt gagtttaggt actggagctg tctttgcagc     540
aagtaaagct gcaattaatc agcttacaaa aaacctggct tgtgactggg ccaaagacaa     600
catacggagc aactgtgttg taccatgggc aaccagaacc ccggttgtag aacatttgtt     660
caaagaccaa aagtttgtgg atgatattat gtctcggact ccaattaaac gtatagcaga     720
accagaagaa gtgtcatcgt tggtgaattt tctttgcttg cctgctgctt cattcatcac     780
tggacaggtt atttgtgttg atggaggatt aactgtgaat ggattccaac ccagcatgag     840
aattacctga aattacttca ctgctttctc tttgtggaac aagcgattct catttgattt     900
caacatgttt gtgacaagtg atgcgcaatt tcgttttatc tgccttctag ttgcatatga     960
aaatgaatgg cctcatttaa ttccatatga aaaacttata taataaatgg aacatcctat    1020
ttaatagcgt tgatgtttct ttttttcctt tataataata ataataataa tacatggcta    1080
ttgt                                                                 1084

<210> SEQ ID NO 36
<211> LENGTH: 272
<212> TYPE: PRT
<213> ORGANISM: Glycine max

<400> SEQUENCE: 36

Met Ala Met Ala Gly Ser Ser Ile Asn Arg Gly Glu Arg Trp Ser Leu
1               5                   10                  15

Asn Gly Met Thr Ala Leu Val Thr Gly Gly Thr Arg Gly Ile Gly His
            20                  25                  30

Ser Ile Val Ser Asp Leu Ala Ala Phe Gly Ala Ala Val His Thr Cys
        35                  40                  45

Ser Arg Thr Gln Thr Glu Leu Asn Lys Cys Leu Gln Glu Trp Gln Ser
    50                  55                  60

Gln Gly Phe Gln Val Thr Gly Ser Leu Cys Asp Val Ser Ser Pro Pro
65                  70                  75                  80

Gln Arg Glu Lys Leu Ile Gln Glu Val Ala Ser Thr Phe Asn Gly Lys
                85                  90                  95

Leu Asn Ile Tyr Val Asn Asn Val Gly Ile Asn Ile Arg Lys Pro Thr
            100                 105                 110

Ile Glu Tyr Thr Ala Glu Glu Tyr Ser Gln Ile Met Thr Val Asn Leu
        115                 120                 125

Asp Ser Ser Phe His Leu Cys Gln Leu Ala Tyr Pro Leu Leu Lys Ala
    130                 135                 140

Ser Glu Lys Gly Ser Ile Val Phe Ile Ser Ser Val Ala Gly Val Val
145                 150                 155                 160
```

Ser Leu Gly Thr Gly Ala Val Phe Ala Ala Ser Lys Ala Ala Ile Asn
            165                 170                 175

Gln Leu Thr Lys Asn Leu Ala Cys Asp Trp Ala Lys Asp Asn Ile Arg
        180                 185                 190

Ser Asn Cys Val Val Pro Trp Ala Thr Arg Thr Pro Val Val Glu His
    195                 200                 205

Leu Phe Lys Asp Gln Lys Phe Val Asp Asp Ile Met Ser Arg Thr Pro
210                 215                 220

Ile Lys Arg Ile Ala Glu Pro Glu Val Ser Ser Leu Val Asn Phe
225                 230                 235                 240

Leu Cys Leu Pro Ala Ala Ser Phe Ile Thr Gly Gln Val Ile Cys Val
                245                 250                 255

Asp Gly Gly Leu Thr Val Asn Gly Phe Gln Pro Ser Met Arg Ile Thr
            260                 265                 270

<210> SEQ ID NO 37
<211> LENGTH: 1133
<212> TYPE: DNA
<213> ORGANISM: Glycine max

<400> SEQUENCE: 37
cccacgattc ggctcgagcg gatatctgac aggttcatca tcataacctt caatgaaaag    60
aaatggctga ggcaagcatt ggcagcaaaa gcagcagatg gtctttacag ggaatgacag   120
ctctcgtcac cggtggatcc aaaggaatcg gatatgctat cgtggaggag ttggcacagc   180
ttggagccac tgtgcacact tgcgctcgga acgaagctga actcaatgaa tccttaaatg   240
aatggaacac aaaaggatac agagtaactg gttccgtctg tgacgtggcg tctcgtgcag   300
aaagacaaga cctcatagct agagtctcca atgagtttaa tggcaaactc aatatccttg   360
taaacaacgt gggaacaaac gtaccgaaac atacccttga tgttacggag gaagacttct   420
catttctgat aaatacaaat cttgaatctg cttaccacct aagccagctt gcacatcctc   480
tcctgaaagc ttcagaggct gcaaacatca ttttttatatc ctccattgct ggtgtgctat   540
caataggtat aggatccact tatggtgcaa caaaaggagc aatgaaccaa ctgactaaaa   600
atttggcatg tgaatgggcc aaagacaata taaggactaa ttgcgttgca ccagggccaa   660
ttagaacccc tcttggtgac aagcacttta agaggaaaa acttaataat agtctgattg   720
cgcgaacccc tcttggacgg attggagagg cagaggaggt ttcttcgttg gtggcattcc   780
tctgcttacc tgcagcatct tacataacag gacaaaccat tgtgttgat ggcggcttca   840
ccgtgaacgg tctctacata agctaggctt attgtgacag tttcaatgtt ttgtttagtc   900
tgttacactc tacttgtatt agtttctctt taagttgtgg agagtggaga ccctatatct   960
gtttttaagg acgtgataat aacagtactc agtgataagt ttgttttttct tgttttgatt  1020
tagtcacatg tccatgatt ctaggagcag tataatcgtg ggcagtttat cctatttccc  1080
gttggttgta aggctttcaa taataataat aataatagcc atgtttgctt ttc         1133

<210> SEQ ID NO 38
<211> LENGTH: 267
<212> TYPE: PRT
<213> ORGANISM: Glycine max

<400> SEQUENCE: 38

Met Ala Glu Ala Ser Ile Gly Ser Lys Ser Ser Arg Trp Ser Leu Gln
1               5                   10                  15

Gly Met Thr Ala Leu Val Thr Gly Gly Ser Lys Gly Ile Gly Tyr Ala

```
            20                  25                  30
Ile Val Glu Glu Leu Ala Gln Leu Gly Ala Thr Val His Thr Cys Ala
        35                  40                  45
Arg Asn Glu Ala Glu Leu Asn Glu Ser Leu Asn Glu Trp Asn Thr Lys
 50                  55                  60
Gly Tyr Arg Val Thr Gly Ser Val Cys Asp Val Ala Ser Arg Ala Glu
 65                  70                  75                  80
Arg Gln Asp Leu Ile Ala Arg Val Ser Asn Glu Phe Asn Gly Lys Leu
                85                  90                  95
Asn Ile Leu Val Asn Asn Val Gly Thr Asn Val Pro Lys His Thr Leu
            100                 105                 110
Asp Val Thr Glu Glu Asp Phe Ser Phe Leu Ile Asn Thr Asn Leu Glu
        115                 120                 125
Ser Ala Tyr His Leu Ser Gln Leu Ala His Pro Leu Leu Lys Ala Ser
    130                 135                 140
Glu Ala Ala Asn Ile Ile Phe Ile Ser Ser Ile Ala Gly Val Leu Ser
145                 150                 155                 160
Ile Gly Ile Gly Ser Thr Tyr Gly Ala Thr Lys Gly Ala Met Asn Gln
                165                 170                 175
Leu Thr Lys Asn Leu Ala Cys Glu Trp Ala Lys Asp Asn Ile Arg Thr
            180                 185                 190
Asn Cys Val Ala Pro Gly Pro Ile Arg Thr Pro Leu Gly Asp Lys His
        195                 200                 205
Phe Lys Glu Glu Lys Leu Asn Asn Ser Leu Ile Ala Arg Thr Pro Leu
    210                 215                 220
Gly Arg Ile Gly Glu Ala Glu Glu Val Ser Ser Leu Val Ala Phe Leu
225                 230                 235                 240
Cys Leu Pro Ala Ala Ser Tyr Ile Thr Gly Gln Thr Ile Cys Val Asp
                245                 250                 255
Gly Gly Phe Thr Val Asn Gly Leu Tyr Ile Ser
            260                 265

<210> SEQ ID NO 39
<211> LENGTH: 1113
<212> TYPE: DNA
<213> ORGANISM: Glycine max

<400> SEQUENCE: 39
cggatatctc aaaggtttat ccttcagtga agagaaatgg cagctgaggc aaattttgat      60
agcaaaagca gcaggtggtc tttgcagggg atgacagctc tcgttaccgg tggttccaaa     120
ggaatcggat atgctatcgt ggaggagttg cacaacttg gagccactgt acacacttgc     180
gctcgcaacg aagctgaact caataaatcc ttaaatgaat ggaacacaaa aggatacaga     240
gtaactggtt cggtccgtga cgtggcgtct cgtgcagaaa gacaagacct catagctaga     300
gtctcaaatg agtttaatgg caaactcaat atccttgtaa acaatgtggg aacaaacata     360
cagaaagaga ccctggattt cacagaggaa gatttcacat ttctggtgaa tacgaatctt     420
gaatcttgtt ccacctaagc cagcttgca catcctctcc taaaagcttc agaagctgca     480
aacatcattc tcatatcctc cattgctggt gtggtagctt caaatatagt atccgttgtg     540
tatggtgcaa caaaggagc aatgaaccaa atgcaaaaac atttggcatg tgaatgggcc     600
aaagacaata taaggactaa ttgcgttgca ccagggccaa ttagaacccc tcttggtgac     660
aagcacttta agaggaaaaa acttaataat agtctgattg cgcgaacccc tcttggacgg     720
attggagagg cagaggaggt tcttcgttg gtggcattcc tctgcttacc tgcagcatct     780
```

```
tacataacag  acaaaccat  ttgtgttgat  ggcggcttca  ccgtgaacgg  tctctacata   840
agctaggctt  attgtgacag  tttcaatgtt  ttgtttagtc  tgttacactc  tacttgtatt   900
agtttctctt  taagttgtgg  agagtggaga  ccctatatct  gttttaagg   acgtgataat   960 aacagtactc  agtgataagt  tgttttttct  tgttttgatt  tagtcacatg  tcccatgatt  1020
ctaggagcag  tataatcgtg  ggcagtttat  cctatttccc  gttggttgta  aggctttcaa  1080
taataataat  aataatagcc  atgtttgctt  ttc                                 1113
```

<210> SEQ ID NO 40
<211> LENGTH: 269
<212> TYPE: PRT
<213> ORGANISM: Glycine max

<400> SEQUENCE: 40

```
Met Ala Ala Glu Ala Asn Phe Asp Ser Lys Ser Arg Trp Ser Leu
1               5                   10                  15

Gln Gly Met Thr Ala Leu Val Thr Gly Gly Ser Lys Gly Ile Gly Tyr
            20                  25                  30

Ala Ile Val Glu Glu Leu Ala Gln Leu Gly Ala Thr Val His Thr Cys
        35                  40                  45

Ala Arg Asn Glu Ala Glu Leu Asn Lys Ser Leu Asn Glu Trp Asn Thr
    50                  55                  60

Lys Gly Tyr Arg Val Thr Gly Ser Val Arg Asp Val Ala Ser Arg Ala
65                  70                  75                  80

Glu Arg Gln Asp Leu Ile Ala Arg Val Ser Asn Glu Phe Asn Gly Lys
                85                  90                  95

Leu Asn Ile Leu Val Asn Asn Val Gly Thr Asn Ile Gln Lys Glu Thr
            100                 105                 110

Leu Asp Phe Thr Glu Glu Asp Phe Thr Phe Leu Val Asn Thr Asn Leu
        115                 120                 125

Glu Ser Cys Phe His Leu Ser Gln Leu Ala His Pro Leu Leu Lys Ala
    130                 135                 140

Ser Glu Ala Ala Asn Ile Ile Leu Ile Ser Ser Ile Ala Gly Val Val
145                 150                 155                 160

Ala Ser Asn Ile Val Ser Val Val Tyr Gly Ala Thr Lys Gly Ala Met
                165                 170                 175

Asn Gln Met Thr Lys His Leu Ala Cys Glu Trp Ala Lys Asp Asn Ile
            180                 185                 190

Arg Thr Asn Cys Val Ala Pro Gly Pro Ile Arg Thr Pro Leu Gly Asp
        195                 200                 205

Lys His Phe Lys Glu Glu Lys Leu Asn Asn Ser Leu Ile Ala Arg Thr
    210                 215                 220

Pro Leu Gly Arg Ile Gly Glu Ala Glu Glu Val Ser Ser Leu Val Ala
225                 230                 235                 240

Phe Leu Cys Leu Pro Ala Ala Ser Tyr Ile Thr Gly Gln Thr Ile Cys
                245                 250                 255

Val Asp Gly Gly Phe Thr Val Asn Gly Leu Tyr Ile Ser
            260                 265
```

<210> SEQ ID NO 41
<211> LENGTH: 1157
<212> TYPE: DNA
<213> ORGANISM: Glycine max

<400> SEQUENCE: 41

-continued

```
caaatccata tcacagaaaa ccatttggc ttctcaaaac cccactcatc atccatatca    60
caaaaaacta ttttggcttc tgcctttcct tttccaggga gctcattgac aatggctgaa   120
acaaagtggg tcatgaagga caaaagatgg tctctccatg gaatgacagc tctagtcaca   180
ggaggcaccc gaggcatagg gcatgccatt gttgaagagt tagctgagtt tggagcaact   240
gttcatatat gtgcacgtaa tcaagatgat attgataaat gtttagaaga gtggaaaaac   300
aagggactta atgtgactgg ttcagtatgt gatttactat gttctgacca acgtaaaaga   360
ttaatggaaa ttgttggctc catctttcat ggaaagctca atattctagt gaacaatgct   420
gctacaaata taacaaagaa gataacagat tacacagcag aggatatatc agccataatg   480
ggcaccaatt ttgagtccgt ttaccatttg tgtcaagttg cacacccact tctaaaagat   540
tctgggaatg ggagcatagt atttatttct tccgtagcag gtttaaaagc tcttcctgtg   600
ttctctgttt atgcagcctc taaggagcc atgaatcaat tcaccaaaaa cttggcattg   660
gaatgggcaa aggataatat tcgtgcaaat gctgttgccc ctggacctgt taagactaaa   720
cttttggagt gtatcgtgaa ttcttcggaa gggaatgagt ctataaatgg aatagtgtct   780
caaacatttg ttggtcgcat gggagaaact aaagagatat cagcattagt tgcttttctt   840
tgccttccgg ctgcatcata catcactgga caggttatat gtgtagatgg gggtttcaca   900
acttagattg ttgttaatga ttttgttgct gaattaaatc ttgtgtttcg tgttcctcca   960
aacgactcat gcttatgtcg ttggttaggt ttatctcctg ttcttaaaca taaccatgtg  1020
ttcttgttta gtttcgtgtg tctttctctc agaattcaac aaggcagaac aattgttaat  1080
tgcctgctcc ccatgactcc atgttatctt atttgttctt tagatgaaac ataacttcaa  1140
ttcctcgtaa aaaaaca                                                 1157
```

<210> SEQ ID NO 42
<211> LENGTH: 264
<212> TYPE: PRT
<213> ORGANISM: Glycine max

<400> SEQUENCE: 42

```
Met Ala Glu Thr Lys Trp Val Met Lys Asp Lys Arg Trp Ser Leu His
1               5                   10                  15

Gly Met Thr Ala Leu Val Thr Gly Gly Thr Arg Gly Ile Gly His Ala
            20                  25                  30

Ile Val Glu Glu Leu Ala Glu Phe Gly Ala Thr Val His Ile Cys Ala
        35                  40                  45

Arg Asn Gln Asp Asp Ile Asp Lys Cys Leu Glu Glu Trp Lys Asn Lys
    50                  55                  60

Gly Leu Asn Val Thr Gly Ser Val Cys Asp Leu Leu Cys Ser Asp Gln
65                  70                  75                  80

Arg Lys Arg Leu Met Glu Ile Val Gly Ser Ile Phe His Gly Lys Leu
                85                  90                  95

Asn Ile Leu Val Asn Asn Ala Ala Thr Asn Ile Thr Lys Lys Ile Thr
            100                 105                 110

Asp Tyr Thr Ala Glu Asp Ile Ser Ala Ile Met Gly Thr Asn Phe Glu
        115                 120                 125

Ser Val Tyr His Leu Cys Gln Val Ala His Pro Leu Leu Lys Asp Ser
    130                 135                 140

Gly Asn Gly Ser Ile Val Phe Ile Ser Ser Val Ala Gly Leu Lys Ala
145                 150                 155                 160

Leu Pro Val Phe Ser Val Tyr Ala Ala Ser Lys Gly Ala Met Asn Gln
                165                 170                 175
```

Phe Thr Lys Asn Leu Ala Leu Glu Trp Ala Lys Asp Asn Ile Arg Ala
            180                 185                 190

Asn Ala Val Ala Pro Gly Pro Val Lys Thr Lys Leu Leu Glu Cys Ile
        195                 200                 205

Val Asn Ser Ser Glu Gly Asn Glu Ser Ile Asn Gly Ile Val Ser Gln
    210                 215                 220

Thr Phe Val Gly Arg Met Gly Glu Thr Lys Glu Ile Ser Ala Leu Val
225                 230                 235                 240

Ala Phe Leu Cys Leu Pro Ala Ala Ser Tyr Ile Thr Gly Gln Val Ile
            245                 250                 255

Cys Val Asp Gly Gly Phe Thr Thr
            260

<210> SEQ ID NO 43
<211> LENGTH: 1366
<212> TYPE: DNA
<213> ORGANISM: Zea mays

<400> SEQUENCE: 43
atccacttgc ctcggccgct atcgtgaccg ggaacaacaa ctgcgagatg gccacggtgg      60
agacctcggg cacggcgata gggtcctccg ggagatgggc actacacggc aagacagccc     120
tcgtcaccgg cggcacccgc ggcatcgggc gtgcggtagt ggaggagctg gcggcgctgg     180
gggcggccgt gcacacatgc tcccggaagg cggaggagct cggcgagcgc atcaaggagt     240
gggaggccag gggattcagc gttacccggt ccgtctgcga cctctccgag agggaccagc     300
gggagcggtt gctccgcgag gttgccgacc gcttcggcgg caagctcaac atcctcgtaa     360
acaatgtagg aacaaacata aggaaaccaa ctactgagtt tactgcagag gaatactcgt     420
ttctgatggc tactaatctt gaatctgcat atcacttgtg ccaaattgca catcctcttt     480
tgaaattatc tgggtcaggc agcattatat tcatatcatc tgttgctgga gcgataggaa     540
tctttagtgg aactatatat gctatgacta aaggtgccat taaccagcta accaagaatt     600
tagcttgtga atgggctaag gacaacataa gagccaactc tgtcgctccg tggtacatca     660
ccacttcact tacggaagga attttggcaa ataagaactt tgaggaacaa gttgtgagtc     720
gaactccgct tggacgtgtc ggagaacctg gagaagtatc ggcacttgtt gcttttcttt     780
gcatgccggg ttccacttat attagcggcc agacgattgc ggtcgacgga ggtatgactg     840
tgaacgggtt ttaccctccc aagccctagg cggcagctgc catgtttctt tgtgctgagg     900
aaacgacaat agctgttgtt cttggttgtt gagaaaaaaa atctaataaa atgtatgtaa     960
aggtaaggtt gtcatgttga tactgttcat tacattacat aattctatca gggcaatgtg    1020
aagaacgttg tgtttagatc aataaaaaat ataggtggtt ggcatatttt ttggacaaag    1080
acggaaactt aggaaacaaa ttttctgatg attgtgaacg gtttctgtaa agcattcagt    1140
gcccttttac tactgtattg ttgtggttgt gttttttgt aatggttgga ttttgtggc     1200 tgattgttct ttttttttt ttcgatctcc actatctttt ccttggttgt ttcccgtgtt    1260
ttttgctttt ggttgttttt ttggtttttt tttccttgtt ttgtattgta tgtcttgttt    1320
ttgctttttt ttttggtttt ttgtgttgtt gattttttt cctttc                   1366

<210> SEQ ID NO 44
<211> LENGTH: 273
<212> TYPE: PRT
<213> ORGANISM: Zea mays

<400> SEQUENCE: 44

Met Ala Thr Val Glu Thr Ser Gly Thr Ala Ile Gly Ser Ser Gly Arg
1               5                   10                  15

Trp Ala Leu His Gly Lys Thr Ala Leu Val Thr Gly Gly Thr Arg Gly
            20                  25                  30

Ile Gly Arg Ala Val Val Glu Leu Ala Ala Leu Gly Ala Ala Val
        35                  40                  45

His Thr Cys Ser Arg Lys Ala Glu Glu Leu Gly Glu Arg Ile Lys Glu
    50                  55                  60

Trp Glu Ala Arg Gly Phe Ser Val Thr Gly Ser Val Cys Asp Leu Ser
65                  70                  75                  80

Glu Arg Asp Gln Arg Glu Arg Leu Leu Arg Glu Val Ala Asp Arg Phe
                85                  90                  95

Gly Gly Lys Leu Asn Ile Leu Val Asn Asn Val Gly Thr Asn Ile Arg
            100                 105                 110

Lys Pro Thr Thr Glu Phe Thr Ala Glu Glu Tyr Ser Phe Leu Met Ala
        115                 120                 125

Thr Asn Leu Glu Ser Ala Tyr His Leu Cys Gln Ile Ala His Pro Leu
    130                 135                 140

Leu Lys Leu Ser Gly Ser Gly Ser Ile Ile Phe Ile Ser Ser Val Ala
145                 150                 155                 160

Gly Ala Ile Gly Ile Phe Ser Gly Thr Ile Tyr Ala Met Thr Lys Gly
                165                 170                 175

Ala Ile Asn Gln Leu Thr Lys Asn Leu Ala Cys Glu Trp Ala Lys Asp
            180                 185                 190

Asn Ile Arg Ala Asn Ser Val Ala Pro Trp Tyr Ile Thr Thr Ser Leu
        195                 200                 205

Thr Glu Gly Ile Leu Ala Asn Lys Asn Phe Glu Glu Gln Val Val Ser
    210                 215                 220

Arg Thr Pro Leu Gly Arg Val Gly Glu Pro Gly Glu Val Ser Ala Leu
225                 230                 235                 240

Val Ala Phe Leu Cys Met Pro Gly Ser Thr Tyr Ile Ser Gly Gln Thr
                245                 250                 255

Ile Ala Val Asp Gly Gly Met Thr Val Asn Gly Phe Tyr Pro Pro Lys
            260                 265                 270

Pro

<210> SEQ ID NO 45
<211> LENGTH: 1295
<212> TYPE: DNA
<213> ORGANISM: Zea mays

<400> SEQUENCE: 45
caaatatggg caggcactag ctagctaggc tgcaaagagc caaagactgc cggcaccgct   60
gctagcttgc tagcatactt ccggtcggca agcagtcgat cgtcgcatgg cgccaggagg  120
cagcggcgag cggtggagcc tggccggcgc gacagcgctg gtcaccggtg gcagcaaggg  180
gatcgggcaa gccgtcgtgg aggagctggc aggctcggc gcgcgcgtgc acacgtgcgc   240
ccgcagcgcg gcggacctgg aggagtgccg ccggcggtgg gccgagaagg ggctccgcgt  300
caccgtctcc gtgtgcgacg tcgccgtgcg cgccgaccgg gagaggctcg tcctggacac  360
ggtcagcggg gccttcgacg caagctcga tatcctggtc aacaacgctg cgctgctgct  420
gctcaagccg gcggcggagt gggcggcgga ggactacgcg cggatcatgg cgaccaacct  480
ggagtcgtgc ttgcacatct cccagctcgc gcaccgctg ctcctcaacg cctccgtcgc   540

-continued

```
cggaggggcg agcatcgtca atgtctcctc catcgccagc gtccttggct tcccgcagga      600
agtcatgtac agcgtcacca aaggaggact gaatcagatg acgaggagcc tagctgtgga      660
gtgggcctgc gataggatcc gtgtgaactg cgtcgcgccg ggcgtgatca tgacggacat      720
gggtaaagag ctaccggcgg cgttggtgga gcaggagcgg tcacgcatcc cgctgcggcg      780
gaccggcgag ccggaggagg tggcgtccct ggtgtcgttc ctctgcatgc cggcggcgtc      840
ctacgtcacc gggcaggtca tcttcgtcga cggcggccgg accattagtg gcgcctgatc      900
gacgacgacg gccagctata tatatagcga agaataaatg tggatctatt ctctattcta      960
ctgtatttga atttgttttc gttcttgtct tcttgatcgg ccatgtatca ccgtcagacg     1020
tcagcggcaa taatccggcc gccgtcggct tgccgggagg gagatatccca actagcgaca    1080 tgcaagctgc ccgatcagtc gtctcgtctc gcctcgccgg ccggcaaggt gcagccactg     1140
tcgttgcctg cagttctgtt cctttttcta ctatggtttc ttgtattcac tgcccactgg     1200
tgatgtttct gtgataacga cttcgacaga ggggatacat tttaaaatcc ttgtgctaat     1260 catttttgt gcacatcaga gttttttgag aacag                                  1295
```

<210> SEQ ID NO 46
<211> LENGTH: 263
<212> TYPE: PRT
<213> ORGANISM: Zea mays

<400> SEQUENCE: 46

```
Met Ala Pro Gly Gly Ser Gly Glu Arg Trp Ser Leu Ala Gly Ala Thr
1               5                   10                  15

Ala Leu Val Thr Gly Gly Ser Lys Gly Ile Gly Gln Ala Val Val Glu
            20                  25                  30

Glu Leu Ala Arg Leu Gly Ala Arg Val His Thr Cys Ala Arg Ser Ala
        35                  40                  45

Ala Asp Leu Glu Glu Cys Arg Arg Arg Trp Ala Glu Lys Gly Leu Arg
    50                  55                  60

Val Thr Val Ser Val Cys Asp Val Ala Val Arg Ala Asp Arg Glu Arg
65                  70                  75                  80

Leu Val Leu Asp Thr Val Ser Gly Ala Phe Asp Gly Lys Leu Asp Ile
                85                  90                  95

Leu Val Asn Asn Ala Ala Leu Leu Leu Lys Pro Ala Glu Trp
            100                 105                 110

Ala Ala Glu Asp Tyr Ala Arg Ile Met Ala Thr Asn Leu Glu Ser Cys
        115                 120                 125

Leu His Ile Ser Gln Leu Ala His Pro Leu Leu Asn Ala Ser Val
    130                 135                 140

Ala Gly Gly Ala Ser Ile Val Asn Val Ser Ser Ile Ala Ser Val Leu
145                 150                 155                 160

Gly Phe Pro Gln Glu Val Met Tyr Ser Val Thr Lys Gly Gly Leu Asn
                165                 170                 175

Gln Met Thr Arg Ser Leu Ala Val Glu Trp Ala Cys Asp Arg Ile Arg
            180                 185                 190

Val Asn Cys Val Ala Pro Gly Val Ile Met Thr Asp Met Gly Lys Glu
        195                 200                 205

Leu Pro Ala Ala Leu Val Glu Gln Glu Arg Ser Arg Ile Pro Leu Arg
    210                 215                 220

Arg Thr Gly Glu Pro Glu Glu Val Ala Ser Leu Val Ser Phe Leu Cys
225                 230                 235                 240

Met Pro Ala Ala Ser Tyr Val Thr Gly Gln Val Ile Phe Val Asp Gly
```

Gly Arg Thr Ile Ser Gly Ala
        260

<210> SEQ ID NO 47
<211> LENGTH: 1259
<212> TYPE: DNA
<213> ORGANISM: Oryza sativa

<400> SEQUENCE: 47

```
ataacgccgt atactgggga cgagccagga acccgaattg ggagtttttc ccgaagaact      60
gataatacgg attttctcgc aaaattattc ccagccgcac cctcgaggcc gatggccgag     120
gcggtcgcaa gcggcgcagc ggggagatgg accctccgcg gcaagacggc cctcgtcacc     180
ggcggcaccc gcggcatcgg gcatgcggtg gtggacgagc tggcggcgct gggggcggcc     240
gtgcacacct gctccaggaa ggaggccgag ctgggcgagc gcctcaggga gtgggagggc     300
aagggcttcc gcgtcaccgg ctcagtctgc gacgtctccg tgcgggagca gcgggaacgc     360
atgctccgcg aggtcgccgg cctctacggt ggcaagctcg acatcctcgt gaacaacgtg     420
ggaacaaact tttcaaaaca aaccactgaa tactctgcag atgattactc gttcataatg     480
gccaccaatc ttgaatctgc gtatcatctg tgccaacttg ctcatcctct tctcaaatca     540
tctgggtcag gaagcgttgt cttcatatcg tcagtctctg gagtggtggc tgtaagttct     600
ggctctgtct atgcgatgac aaaaggtgcc atgaaccagc tggccaagaa cctggcatgt     660
gagtgggcga agacaatat aagaaccaat tctgttgcac catggtacat gaagacttca     720
cttgtggaag atgaattggc aaggaaggac ttcgctgaca gcgtcgtgcg tcgaacagcg     780
ctgaagcgcg tggagaaacc agaagaggtg tcatcgctgg tcgcgttcct gtgcatgccc     840
ggcgcttcct acatcaccgg ccagacgatc tcggtcgacg gcggcatgac cataaacgga     900
ctgtatccac ctcaggacta gaccgaatag gcaaaccgta tggccgtatg gggatcgaag     960
aactgtgttt ggagaggtca gaggtgaggc tcgaacgtca gtaaaactca actatcccaa    1020
acaaacagga gatcgcaaat agaccccgtct gaacttgatt ggtttgcact tgggtatgca    1080
ccgcatgcta ctgtactaaa ttaaaaaaaa acgtttgttg cgagcaacaa aacgaaatcc    1140
tgcgtggata gcgggcgtac tgcatagtgt tgtgtcgttc gtatgcgcca tagacaaacg    1200
gaatgccctt gaaaaaaagt ttaattggat gcatcgtgca gcctattaca atttcttcc    1259
```

<210> SEQ ID NO 48
<211> LENGTH: 269
<212> TYPE: PRT
<213> ORGANISM: Oryza sativa

<400> SEQUENCE: 48

Met Ala Glu Ala Val Ala Ser Gly Ala Ala Gly Arg Trp Thr Leu Arg
1               5                   10                  15

Gly Lys Thr Ala Leu Val Thr Gly Gly Thr Arg Gly Ile Gly His Ala
            20                  25                  30

Val Val Asp Glu Leu Ala Ala Leu Gly Ala Ala Val His Thr Cys Ser
        35                  40                  45

Arg Lys Glu Ala Glu Leu Gly Glu Arg Leu Arg Glu Trp Glu Gly Lys
    50                  55                  60

Gly Phe Arg Val Thr Gly Ser Val Cys Asp Val Ser Val Arg Glu Gln
65                  70                  75                  80

Arg Glu Arg Met Leu Arg Glu Val Ala Gly Leu Tyr Gly Gly Lys Leu
                85                  90                  95

Asp Ile Leu Val Asn Asn Val Gly Thr Asn Phe Ser Lys Gln Thr Thr
            100                 105                 110

Glu Tyr Ser Ala Asp Asp Tyr Ser Phe Ile Met Ala Thr Asn Leu Glu
        115                 120                 125

Ser Ala Tyr His Leu Cys Gln Leu Ala His Pro Leu Leu Lys Ser Ser
130                 135                 140

Gly Ser Gly Ser Val Val Phe Ile Ser Ser Val Ser Gly Val Val Ala
145                 150                 155                 160

Val Ser Ser Gly Ser Val Tyr Ala Met Thr Lys Gly Ala Met Asn Gln
                165                 170                 175

Leu Ala Lys Asn Leu Ala Cys Glu Trp Ala Lys Asp Asn Ile Arg Thr
            180                 185                 190

Asn Ser Val Ala Pro Trp Tyr Met Lys Thr Ser Leu Val Glu Asp Glu
        195                 200                 205

Leu Ala Arg Lys Asp Phe Ala Asp Ser Val Val Arg Arg Thr Ala Leu
210                 215                 220

Lys Arg Val Gly Glu Pro Glu Val Ser Ser Leu Val Ala Phe Leu
225                 230                 235                 240

Cys Met Pro Gly Ala Ser Tyr Ile Thr Gly Gln Thr Ile Ser Val Asp
                245                 250                 255

Gly Gly Met Thr Ile Asn Gly Leu Tyr Pro Pro Gln Asp
            260                 265

<210> SEQ ID NO 49
<211> LENGTH: 804
<212> TYPE: DNA
<213> ORGANISM: Nostoc sp. PCC 7120

<400> SEQUENCE: 49
gtggaaaatt tgttacccc tccagctttt ggggaaaaaa tccgggaacg ctggacatta      60
gccggacgaa aagctttgat taccggagct acaaaaggaa ttggtttagc gatcgctcaa    120
gagttcttgg ctttaggtgc agaagtcgtc attgtggctc gcaatgctga agcgattgag    180
cagcagatga aggcttggca ttctgcgggg aaagttcacg gagttgcagc cgacgtttcc    240
acttctgagg gtcgtcaaat gatgcttgat tacgttagca agacctttgg agaacttgac    300
attttggtga caacgttgg cacaaatatt cgtaagaaag cgactgatta cacagaagaa    360
gaatttgctg cgatatttca aattaatcta acttctatat ttgagctttc ccgactgttt    420
tatcccttac tcaaaacaag taaaaacagc agtatcgtta acatcggttc tgttgctgga    480
ttaatttccg ttcggactgg cgcacccat ggcatgacca agctgcact cgtgcagtta    540 acgcgatcgc tggcggtaga atgggcagat gatggtattc gcgttaatgc gatcgcacct    600
tggtttatcc aaaactcctct gaccgagcct ctactcaaca atcccgaaac tttaagcgca    660 gtccttttcac gcacaccaat gaaacgcgtg ggtcaacccg aagaagtagc cagcctgacg    720
gcttttctct gtatgcctac cgcatcctac atcacaggac aatgtattgc tgttgatgga    780
ggatttctgg catttggttt ttaa                                            804

<210> SEQ ID NO 50
<211> LENGTH: 267
<212> TYPE: PRT
<213> ORGANISM: Nostoc sp. PCC 7120

<400> SEQUENCE: 50

Met Glu Asn Phe Val Thr Pro Pro Ala Phe Gly Glu Lys Ile Arg Glu
1               5                   10                  15

| | | | | | | | | | | | |
|---|---|---|---|---|---|---|---|---|---|---|---|
|Arg|Trp|Thr|Leu|Ala|Gly|Arg|Lys|Ala|Leu|Ile|Thr|Gly|Ala|Thr|Lys|
| | |20| | | |25| | | |30| |

Arg Trp Thr Leu Ala Gly Arg Lys Ala Leu Ile Thr Gly Ala Thr Lys
            20                  25                  30

Gly Ile Gly Leu Ala Ile Ala Gln Glu Phe Leu Ala Leu Gly Ala Glu
        35                  40                  45

Val Val Ile Val Ala Arg Asn Ala Glu Ala Ile Gln Gln Met Lys
 50                  55                  60

Ala Trp His Ser Ala Gly Lys Val His Gly Val Ala Ala Asp Val Ser
 65                  70                  75                  80

Thr Ser Glu Gly Arg Gln Met Met Leu Asp Tyr Val Ser Lys Thr Phe
                85                  90                  95

Gly Glu Leu Asp Ile Leu Val Asn Asn Val Gly Thr Asn Ile Arg Lys
            100                 105                 110

Lys Ala Thr Asp Tyr Thr Glu Glu Phe Ala Ala Ile Phe Gln Ile
            115                 120                 125

Asn Leu Thr Ser Ile Phe Glu Leu Ser Arg Leu Phe Tyr Pro Leu Leu
130                 135                 140

Lys Thr Ser Lys Asn Ser Ser Ile Val Asn Ile Gly Ser Val Ala Gly
145                 150                 155                 160

Leu Ile Ser Val Arg Thr Gly Ala Pro Tyr Gly Met Thr Lys Ala Ala
                165                 170                 175

Leu Val Gln Leu Thr Arg Ser Leu Ala Val Glu Trp Ala Asp Asp Gly
            180                 185                 190

Ile Arg Val Asn Ala Ile Ala Pro Trp Phe Ile Gln Thr Pro Leu Thr
        195                 200                 205

Glu Pro Leu Leu Asn Asn Pro Glu Thr Leu Ser Ala Val Leu Ser Arg
    210                 215                 220

Thr Pro Met Lys Arg Val Gly Gln Pro Glu Glu Val Ala Ser Leu Thr
225                 230                 235                 240

Ala Phe Leu Cys Met Pro Thr Ala Ser Tyr Ile Thr Gly Gln Cys Ile
                245                 250                 255

Ala Val Asp Gly Gly Phe Leu Ala Phe Gly Phe
            260                 265

<210> SEQ ID NO 51
<211> LENGTH: 777
<212> TYPE: DNA
<213> ORGANISM: Xanthomonas campestris

<400> SEQUENCE: 51

```

```
tacatcaccg gtgaatgcat cgcggtggat ggcggcttcc tgcgtcatgg gttctag      777
```

<210> SEQ ID NO 52
<211> LENGTH: 258
<212> TYPE: PRT
<213> ORGANISM: Xanthomonas campestris

<400> SEQUENCE: 52

```
Met Thr Ala His Arg Trp Arg Leu Asp Gly Gln Thr Ala Leu Ile Thr
1               5                   10                  15
Gly Ala Ser Ala Gly Ile Gly Leu Ala Ile Ala Arg Glu Leu Leu Gly
                20                  25                  30
Phe Gly Ala Asp Leu Leu Met Val Ala Arg Asp Ala Asp Ala Leu Ala
            35                  40                  45
Gln Ala Arg Asp Glu Leu Ala Glu Glu Phe Pro Glu Arg Glu Leu His
        50                  55                  60
Gly Leu Ala Ala Asp Val Ser Asp Asp Glu Arg Arg Ala Ile Leu
65                  70                  75                  80
Asp Trp Val Glu Asp His Ala Asp Gly Leu His Leu Leu Ile Asn Asn
                85                  90                  95
Ala Gly Gly Asn Ile Thr Arg Ala Ala Ile Asp Tyr Thr Glu Asp Glu
                100                 105                 110
Trp Arg Gly Ile Phe Glu Thr Asn Val Phe Ser Ala Phe Glu Leu Ser
            115                 120                 125
Arg Tyr Ala His Pro Leu Leu Thr Arg His Ala Ala Ser Ala Ile Val
        130                 135                 140
Asn Val Gly Ser Val Ser Gly Ile Thr His Val Arg Ser Gly Ala Pro
145                 150                 155                 160
Tyr Gly Met Thr Lys Ala Ala Leu Gln Gln Met Thr Arg Asn Leu Ala
                165                 170                 175
Val Glu Trp Ala Glu Asp Gly Ile Arg Val Asn Ala Val Ala Pro Trp
            180                 185                 190
Tyr Ile Arg Thr Arg Arg Thr Ser Gly Pro Leu Ser Asp Pro Asp Tyr
        195                 200                 205
Tyr Glu Gln Val Ile Glu Arg Thr Pro Met Arg Arg Ile Gly Glu Pro
    210                 215                 220
Glu Glu Val Ala Ala Ala Val Gly Phe Leu Cys Leu Pro Ala Ala Ser
225                 230                 235                 240
Tyr Ile Thr Gly Glu Cys Ile Ala Val Asp Gly Gly Phe Leu Arg His
                245                 250                 255
Gly Phe
```

<210> SEQ ID NO 53
<211> LENGTH: 777
<212> TYPE: DNA
<213> ORGANISM: Xylella fastidiosa

<400> SEQUENCE: 53

```
atgacccaat cccgttggcg tttggatggc cgtacggctt tgatcacggg ggctagtaca      60
ggtatcggtc tggctgttgc tcgtgagttg ttgggcctgg gtgccgatgt gctgttggta     120
gcgcgtaatg ctgatttgct ggggcgagta cgcgatgaac tggcagagga attccctgag     180
cgtgagttac atggattggc tgctgatgtt gctgacgatg tggaccgccg tgcgattctg     240
gattgggtcg aagattgcag taatggtttg catgtgttga tcaacaatgc tggtggtaat     300
gtgacgcgtg cagcgcttga atatacagaa gacgagtggc gtgagatttt cgagatcaat     360
```

```
ctgttctctg cgttcgagtt gtgtcgttac acgcagccgt tgctggcgtg tcatgcaagt    420
acggcgattg tcaatattgg cagtgtatct ggcttgacgc atgtgcgcag tggagtgccg    480
tatgggatga gcaaggcggc gttgcaccaa atgacccgca atttggctgt ggaatgggct    540
gaggatggga tccgtgtcaa tgcggtagcg ccttggtata tccgtacgcg tcgtacgtcg    600
gagccgctct ctgatgtgta ctattacgag caagtcattg aacgtacgcc gatgcgccgc    660
attggagagc cggaggaagt agctgcggca gtggcatttc tttgtttgcc agcgtccagt    720
tatgtgaccg cgaatgtat tgcggtggat ggcggtttta tgcgctatgg tttctga       777
```

```
<210> SEQ ID NO 54
<211> LENGTH: 258
<212> TYPE: PRT
<213> ORGANISM: Xylella fastidiosa

<400> SEQUENCE: 54

Met Thr Gln Ser Arg Trp Arg Leu Asp Gly Arg Thr Ala Leu Ile Thr
1               5                   10                  15

Gly Ala Ser Thr Gly Ile Gly Leu Ala Val Ala Arg Glu Leu Leu Gly
                20                  25                  30

Leu Gly Ala Asp Val Leu Leu Val Ala Arg Asn Ala Asp Leu Leu Gly
            35                  40                  45

Arg Val Arg Asp Glu Leu Ala Glu Glu Phe Pro Glu Arg Glu Leu His
        50                  55                  60

Gly Leu Ala Ala Asp Val Ala Asp Val Asp Arg Arg Ala Ile Leu
65                  70                  75                  80

Asp Trp Val Glu Asp Cys Ser Asn Gly Leu His Val Leu Ile Asn Asn
                85                  90                  95

Ala Gly Gly Asn Val Thr Arg Ala Ala Leu Glu Tyr Thr Glu Asp Glu
                100                 105                 110

Trp Arg Glu Ile Phe Glu Ile Asn Leu Phe Ser Ala Phe Glu Leu Cys
            115                 120                 125

Arg Tyr Thr Gln Pro Leu Leu Ala Cys His Ala Ser Thr Ala Ile Val
        130                 135                 140

Asn Ile Gly Ser Val Ser Gly Leu Thr His Val Arg Ser Gly Val Pro
145                 150                 155                 160

Tyr Gly Met Ser Lys Ala Ala Leu His Gln Met Thr Arg Asn Leu Ala
                165                 170                 175

Val Glu Trp Ala Glu Asp Gly Ile Arg Val Asn Ala Val Ala Pro Trp
            180                 185                 190

Tyr Ile Arg Thr Arg Arg Thr Ser Glu Pro Leu Ser Asp Val Tyr Tyr
        195                 200                 205

Tyr Glu Gln Val Ile Glu Arg Thr Pro Met Arg Arg Ile Gly Glu Pro
    210                 215                 220

Glu Glu Val Ala Ala Ala Val Ala Phe Leu Cys Leu Pro Ala Ser Ser
225                 230                 235                 240

Tyr Val Thr Gly Glu Cys Ile Ala Val Asp Gly Gly Phe Met Arg Tyr
                245                 250                 255

Gly Phe

<210> SEQ ID NO 55
<211> LENGTH: 25
<212> TYPE: DNA
<213> ORGANISM: Arabidopsis thaliana

<400> SEQUENCE: 55
```

| | |
|---|---|
| atatttaaca agccatggca aagga | 25 |

<210> SEQ ID NO 56
<211> LENGTH: 27
<212> TYPE: DNA
<213> ORGANISM: Arabidopsis thaliana

<400> SEQUENCE: 56

| | |
|---|---|
| atatgtgttt gaattcatag tcttgaa | 27 |

<210> SEQ ID NO 57
<211> LENGTH: 27
<212> TYPE: DNA
<213> ORGANISM: Arabidopsis thaliana

<400> SEQUENCE: 57

| | |
|---|---|
| gtaagatatc atatggcaaa ggaaggg | 27 |

<210> SEQ ID NO 58
<211> LENGTH: 36
<212> TYPE: DNA
<213> ORGANISM: arabidopsis thaliana

<400> SEQUENCE: 58

| | |
|---|---|
| gcgcgaattc tcgagtcata gtcttgaagg aaaaac | 36 |

<210> SEQ ID NO 59
<211> LENGTH: 21
<212> TYPE: DNA
<213> ORGANISM: arabidopsis thaliana

<400> SEQUENCE: 59

| | |
|---|---|
| ggctacaaat ctcgagtcag c | 21 |

<210> SEQ ID NO 60
<211> LENGTH: 21
<212> TYPE: DNA
<213> ORGANISM: arabidopsis thaliana

<400> SEQUENCE: 60

| | |
|---|---|
| gctgactcga gatttgtagc c | 21 |

<210> SEQ ID NO 61
<211> LENGTH: 31
<212> TYPE: DNA
<213> ORGANISM: Nostoc sp. PCC 7120

<400> SEQUENCE: 61

| | |
|---|---|
| gtaagatatc atatgagtga tgcctacggt g | 31 |

<210> SEQ ID NO 62
<211> LENGTH: 34
<212> TYPE: DNA
<213> ORGANISM: Nostoc sp. PCC 7120

<400> SEQUENCE: 62

| | |
|---|---|
| gtaagatctg ccaccatggg tgatgcctac ggtg | 34 |

<210> SEQ ID NO 63
<211> LENGTH: 31
<212> TYPE: DNA
<213> ORGANISM: Nostoc sp. PCC 7120

<400> SEQUENCE: 63

```
gagaagcttc tcgagttaaa aaccgaaagc c                                    31
```

<210> SEQ ID NO 64
<211> LENGTH: 19
<212> TYPE: DNA
<213> ORGANISM: Nostoc sp. PCC 7120

<400> SEQUENCE: 64

```
cctctactgc aaaataggg                                                  19
```

<210> SEQ ID NO 65
<211> LENGTH: 19
<212> TYPE: DNA
<213> ORGANISM: Nostoc sp. PCC 7120

<400> SEQUENCE: 65

```
ccctattttg cagtagagg                                                  19
```

<210> SEQ ID NO 66
<211> LENGTH: 901
<212> TYPE: DNA
<213> ORGANISM: Nostoc sp.

<400> SEQUENCE: 66

```
cattgggcac ttacaagata aactcttaaa ttgataccct gaaaataaaa aatccgcaaa     60
attacaaatg agtgatgcct acggtgggct aagtctacgc tggacactga gaggaaagaa    120
agcactgatt acaggtgcta ccaaaggcat tggactagct gttgccaatg agttcttatc    180
tctaggtgca gaagtcataa ttgtggcacg gaattctcaa gatgttgacc aacaactaat    240
tatctggcga gaattaggat tacctgctta tggaattacg gcagatgttg caactgctga    300
ggggcgacaa gccatttttg agcaggttgg caaaacctgg gataaattag acatcctggt    360
taataatgtg ggaaccaata tcagcaaaaa agtactagac tacacggctg ctgaatatca    420
gttcatcatc cagacgaacc agatatcaat ttttgagatg tgccgtctgt tttaccctct    480
actgcaaaat agggaaaata gcagcattgt gaatataagt tctgtggcgg gtttagtctc    540
aaaccgtaca ggcgctcctt atggtatgac taaagcggct ataaatcaat tgacgcgatc    600
gctatcagtt gaatgggctt gcgatcaaat tagggtaaat accgtagcac ttgggctat    660
tcgcactcct ctaaccgagt ctgtactcga taaccaagat tttctcaaat tagttctgtc    720
ccaaacacct atgggaagag ttggtcaacc agaagaagta gcgggtttag tagcatttct    780
ttgtatgcct gcggcatctt tcatcactgg acaatgtatc actgtcgatg gtggttttt    840
ggctttcggt ttttaagtct caaagccaga tccatccacg aggtagaaga aactacttac    900
a                                                                    901
```

<210> SEQ ID NO 67
<211> LENGTH: 262
<212> TYPE: PRT
<213> ORGANISM: Nostoc sp.

<400> SEQUENCE: 67

```
Met Ser Asp Ala Tyr Gly Gly Leu Ser Leu Arg Trp Thr Leu Arg Gly
1               5                   10                  15

Lys Lys Ala Leu Ile Thr Gly Ala Thr Lys Gly Ile Gly Leu Ala Val
            20                  25                  30

Ala Asn Glu Phe Leu Ser Leu Gly Ala Glu Val Ile Ile Val Ala Arg
        35                  40                  45
```

```
Asn Ser Gln Asp Val Asp Gln Gln Leu Ile Ile Trp Arg Glu Leu Gly
 50                  55                  60
Leu Pro Ala Tyr Gly Ile Thr Ala Asp Val Ala Thr Ala Glu Gly Arg
 65                  70                  75                  80
Gln Ala Ile Phe Glu Gln Val Gly Lys Thr Trp Asp Lys Leu Asp Ile
                 85                  90                  95
Leu Val Asn Asn Val Gly Thr Asn Ile Ser Lys Lys Val Leu Asp Tyr
                100                 105                 110
Thr Ala Ala Glu Tyr Gln Phe Ile Ile Gln Thr Asn Gln Ile Ser Ile
                115                 120                 125
Phe Glu Met Cys Arg Leu Phe Tyr Pro Leu Leu Gln Asn Arg Glu Asn
130                 135                 140
Ser Ser Ile Val Asn Ile Ser Ser Val Ala Gly Leu Val Ser Asn Arg
145                 150                 155                 160
Thr Gly Ala Pro Tyr Gly Met Thr Lys Ala Ala Ile Asn Gln Leu Thr
                165                 170                 175
Arg Ser Leu Ser Val Glu Trp Ala Cys Asp Gln Ile Arg Val Asn Thr
                180                 185                 190
Val Ala Pro Trp Ala Ile Arg Thr Pro Leu Thr Glu Ser Val Leu Asp
                195                 200                 205
Asn Gln Asp Phe Leu Lys Leu Val Leu Ser Gln Thr Pro Met Gly Arg
210                 215                 220
Val Gly Gln Pro Glu Glu Val Ala Gly Leu Val Ala Phe Leu Cys Met
225                 230                 235                 240
Pro Ala Ala Ser Phe Ile Thr Gly Gln Cys Ile Thr Val Asp Gly Gly
                245                 250                 255
Phe Leu Ala Phe Gly Phe
            260

<210> SEQ ID NO 68
<211> LENGTH: 810
<212> TYPE: DNA
<213> ORGANISM: Nostoc sp.

<400> SEQUENCE: 68
tcatacatgg ccactgccag ctctataaac aagaggttta gcctcgccgg tgccacggcg      60
cttgtcaccg gtggcagcaa aggcatcggc cgcgccatcg tggaagagct ggcgagcttc     120
ggcgcgacgg tgcacacctg cgctcggaac caggcggagc tgagcagatg ccaggaggag     180
tggacggcca agggcctcgc cgtcaccgtc tccgtctgcg acgtggcggt gcgcgccgac     240
agggaggcgc tcgccggcag ggtgtccgcc atgttcgacg gcaagctcag catcctggtg     300
aacaacgctg gacggcgta cctgaagccg cggcggacc tgacgccgga ggagacgtcg      360
aggttgatga cgaccaactt cgagtcgtgc ttccacctga gccagctgtt ctaccctctc     420
ctcaaggact ccggaagagg cagtatcgtt aatatctcgt ccgtcgcttc tgtcctcgcg     480
ttccattctc ttcctatcta ctcggctgcc aaaggagcaa tgaaccaagt cacaaggaac     540
ctggcttgtg agtgggcgag cgatgggatc agagtcaatt ccgttgcacc gggctacatc     600
cagactccac tcctaactgc cttcgtggcc ggcaacgatt tcgcacaggt tgagttcaac     660
cgtcttcctt tgggccgtct cggtaaacct gaggacatct cgtcgttggt ggcgttcctg     720
tgcatgcctg cggcctccta catcactggc cagattatat gcgtcgatgg gggccgtatg     780
ctttcttaat aaactctaca tatacaaaat                                       810

<210> SEQ ID NO 69
```

```
<211> LENGTH: 260
<212> TYPE: PRT
<213> ORGANISM: Nostoc sp.

<400> SEQUENCE: 69

Met Ala Thr Ala Ser Ser Ile Asn Lys Arg Phe Ser Leu Ala Gly Ala
1               5                   10                  15

Thr Ala Leu Val Thr Gly Gly Ser Lys Gly Ile Gly Arg Ala Ile Val
            20                  25                  30

Glu Glu Leu Ala Ser Phe Gly Ala Thr Val His Thr Cys Ala Arg Asn
        35                  40                  45

Gln Ala Glu Leu Ser Arg Cys Gln Glu Glu Trp Thr Ala Lys Gly Leu
    50                  55                  60

Ala Val Thr Val Ser Val Cys Asp Val Ala Val Arg Ala Asp Arg Glu
65                  70                  75                  80

Ala Leu Ala Gly Arg Val Ser Ala Met Phe Asp Gly Lys Leu Ser Ile
                85                  90                  95

Leu Val Asn Asn Ala Gly Thr Ala Tyr Leu Lys Pro Ala Ala Asp Leu
            100                 105                 110

Thr Pro Glu Glu Thr Ser Arg Leu Met Thr Thr Asn Phe Glu Ser Cys
        115                 120                 125

Phe His Leu Ser Gln Leu Phe Tyr Pro Leu Leu Lys Asp Ser Gly Arg
    130                 135                 140

Gly Ser Ile Val Asn Ile Ser Ser Val Ala Ser Val Leu Ala Phe His
145                 150                 155                 160

Ser Leu Pro Ile Tyr Ser Ala Ala Lys Gly Ala Met Asn Gln Val Thr
                165                 170                 175

Arg Asn Leu Ala Cys Glu Trp Ala Ser Asp Gly Ile Arg Val Asn Ser
            180                 185                 190

Val Ala Pro Gly Tyr Ile Gln Thr Pro Leu Leu Thr Ala Phe Val Ala
        195                 200                 205

Gly Asn Asp Phe Ala Gln Val Glu Phe Asn Arg Leu Pro Leu Gly Arg
    210                 215                 220

Leu Gly Lys Pro Glu Asp Ile Ser Ser Leu Val Ala Phe Leu Cys Met
225                 230                 235                 240

Pro Ala Ala Ser Tyr Ile Thr Gly Gln Ile Ile Cys Val Asp Gly Gly
                245                 250                 255

Arg Met Leu Ser
            260

<210> SEQ ID NO 70
<211> LENGTH: 1253
<212> TYPE: DNA
<213> ORGANISM: Glycine max

<400> SEQUENCE: 70
gaggaagtat ccgatatttg acaggttcat catcataacc ttcaatgaaa agaaatggct      60
gaggcaagca ttggcagcaa aagcagcaga tggtctttac agggaatgac agctctcgtc     120
accggtggat ccaaaggaat cggatatgct atcgtggagg agttggcaca gcttggagcc     180
actgtgcaca cttgcgctcg gaacgaagct gaactcaatg aatccttaaa tgaatggaac     240
acaaaaggat acagagtaac tggttccgtc tgtgacgtgg cgtctcgtgc agaaagacaa     300
gacctcatag ctagagtctc caatgagttt aatggcaaac tcaatatcct tgtaaacaac     360
gtgggaacaa acgtaccgaa acatacccct tgatgttacgg aggaagactt ctcatttctg     420
ataaatacaa atcttgaatc tgcttaccac ctaagccagc ttgcacatcc tctcctgaaa     480
```

```
gcttcagagg ctgcaaacat cattttata tcctccattg ctggtgtgct atcaataggt      540
ataggatcca cttatggtgc aacaaaagga gcaatgaacc aactgactaa aaatttggca      600
tgtgagtggg ccaaagacaa tataaggact aattgcgttg caccagggcc aatcaaaacc      660
cctctcggtg acaagcattt taaaaatgaa aaacttctta atgctttcat ttcgcaaacc      720 cccttggac ggattggaga agcagaggaa gtgtcttcat tggtggcatt cctctgctta      780
cctgcagcct cttacataac aggacagacc atttgtgttg atggtggatt aacagtgaat      840
ggtctctata taaattagag aagtactacc aacacactct ctaacacact tctcttgaca      900
catattctac cataagttac aaataataaa aaattacaaa atcatgaaaa taagatctag      960
gacccatata ttttgtgat atctaaaaaa tttcaagcaa taaaaaaaat gtattgaaaa     1020
gagtgtataa gataatgtgt tgttagcatt tttatataaa ctatgttaag agcaaggtct     1080
gatgcatacg ttgctagttt ttatattagt attgagaata aatagctgaa agtcccttgg     1140
ttcaatctat atcatttggg aggggggaatt tgttgggaat aaatttgtat gtccacgatc     1200
caatcatcat gtaatcaatt ttaattttaa taataaagta ttattttatt ttc            1253

<210> SEQ ID NO 71
<211> LENGTH: 267
<212> TYPE: PRT
<213> ORGANISM: Glycine max

<400> SEQUENCE: 71

Met Ala Glu Ala Ser Ile Gly Ser Lys Ser Arg Trp Ser Leu Gln
1               5                   10                  15

Gly Met Thr Ala Leu Val Thr Gly Gly Ser Lys Gly Ile Gly Tyr Ala
                20                  25                  30

Ile Val Glu Glu Leu Ala Gln Leu Gly Ala Thr Val His Thr Cys Ala
            35                  40                  45

Arg Asn Glu Ala Glu Leu Asn Glu Ser Leu Asn Glu Trp Asn Thr Lys
        50                  55                  60

Gly Tyr Arg Val Thr Gly Ser Val Cys Asp Val Ala Ser Arg Ala Glu
65                  70                  75                  80

Arg Gln Asp Leu Ile Ala Arg Val Ser Asn Glu Phe Asn Gly Lys Leu
                85                  90                  95

Asn Ile Leu Val Asn Asn Val Gly Thr Asn Val Pro Lys His Thr Leu
            100                 105                 110

Asp Val Thr Glu Glu Asp Phe Ser Phe Leu Ile Asn Thr Asn Leu Glu
        115                 120                 125

Ser Ala Tyr His Leu Ser Gln Leu Ala His Pro Leu Leu Lys Ala Ser
    130                 135                 140

Glu Ala Ala Asn Ile Ile Phe Ile Ser Ser Ile Ala Gly Val Leu Ser
145                 150                 155                 160

Ile Gly Ile Gly Ser Thr Tyr Gly Ala Thr Lys Gly Ala Met Asn Gln
                165                 170                 175

Leu Thr Lys Asn Leu Ala Cys Glu Trp Ala Lys Asp Asn Ile Arg Thr
            180                 185                 190

Asn Cys Val Ala Pro Gly Pro Ile Lys Thr Pro Leu Gly Asp Lys His
        195                 200                 205

Phe Lys Asn Glu Lys Leu Leu Asn Ala Phe Ile Ser Gln Thr Pro Leu
    210                 215                 220

Gly Arg Ile Gly Glu Ala Glu Glu Val Ser Ser Leu Val Ala Phe Leu
225                 230                 235                 240
```

-continued

```
Cys Leu Pro Ala Ala Ser Tyr Ile Thr Gly Gln Thr Ile Cys Val Asp
            245                 250                 255

Gly Gly Leu Thr Val Asn Gly Leu Tyr Ile Asn
            260                 265
```

METHOD OF INCREASING PLANT ORGAN AND SEED SIZE IN A PLANT

CROSS REFERENCE TO RELATED APPLICATIONS

This application is a divisional application of application Ser. No. 10/513,167, filed Nov. 1, 2004, issued U.S. Pat. No. 7,335,812 on Feb. 26, 2008, which is a §371 application of PCT/US2003/14989 filed on May 14, 2003 and claims the benefit of priority to U.S. Provisional Application No. 60/381,100, filed May 15, 2002.

FIELD OF THE INVENTION

This invention relates to plant molecular biology. In particularly, this invention relates to transgenic plants having increased or enhanced seed and organ sizes.

BACKGROUND OF THE INVENTION

Recent advances in genetic engineering have provided the prerequisite tools to transform plants to contain foreign (often referred to as "heterogeneous or heterologous") or improved endogenous genes. The introduction of such a gene in a plant can desirably lead to an improvement of an already existing pathway in plant tissues or introduction of a novel pathway to modify desired product levels, increase metabolic efficiency, and/or save on energy cost to the cell. Plants with unique physiological and biochemical traits and characteristics, such as herbicide resistance and insect resistance, have already been produced. The ability to create traits that play an essential role in plant growth and development, crop yield potential and stability, and crop quality and composition are particularly desirable targets for the crop plant improvement.

Normally a plant goes through a development cycle, which includes seed germination, maturation of plant, reproduction, and finally senescence that leads to death of a plant. Several biological processes are common to different stages of plant development. Desired effects such as growth of tissue organ are achieved in nature by fine-tuning of the metabolism of the organism. The final phase of growth is senescence which is a highly regulated, genetically controlled and active process (Thomas H., and Stoddart J. L., Ann. Rev. Plant Physiol (31) 83-111, 1980). Senescence is mostly studied in plant leaves and is regarded as a series of events concerned with cellular disassembly and the mobilization of released material to other plant parts such as seeds, storage organs or developing leaves and flowers (Nooden L. D. In Senescence and Aging in Plants, Academic press, 391-439, 1988). Leaf senescence can be initiated by seed development in certain species of plants. This was demonstrated in soybean by surgically removing flowers or physically restricting pod growth to observe the delay in leaf senescence (Nooden L. D. In Senescence and Aging in Plants, Academic press, 330-368, 1988; Miceli F, Crafts-Brandner S. J., Egli D. B. Crop Sci. (35), 1080-1085, 1995). During senescence, partitioning of resources between vegetative and reproductive development involves a complex interplay of generative and degenerative processes, requiring differential expression of genes.

Differentially expressed genes during senescence are usually referred as "Senescence Associated Genes" or SAGs (Hensel L. L, Grbic V., Baumgarten D. A., Bleecker A. B., The Plant Cell (5) 553-564 1993). All SAG genes may not be functionally related, but they all are involved in similar physiological processes. In the past, senescence studies were directed towards understanding processes to generally enhance knowledge and applying this information relating to senescence in agriculture to enhancing yield and reducing post harvest losses (Hensel L. L, Grbic V., Baumgarten D. A., Bleecker A. B., The Plant Cell (5) 553-564 1993; Gan S., Amasino R. M., Science, (270) 1986-1988, 1995; Gan S., Amasino R. M., Plant Physiol., (113) 313-319, 1997; Guarente L., Ruvkun G., Amasino R. M., Proc. Natl. Acad. Sci. USA (95) 1034-1036, 1998; U.S. Pat. No. 5,689,042; PCT/US00/03494; and PCT/US00/18364, July 2000).

The SAG 13 gene was first described by Lohman et al. in 1994 (Lohman K. M., Gan S., John M. C., Amasino R. M., Physiologia Plantarum (92) 322-328, 1994) and then by Weaver et al. in 1998 (Weaver L. M. Gan S., Quirino B, Amasino R. M., Plant Mol. Biol. 455-469, 1998) as one of the genes associated with senescence. SAG genes by definition are up regulated during age-mediated senescence. SAG 13 was observed to be induced strongly shortly before visible senescence marked by yellowing of green leaves.

SUMMARY OF THE INVENTION

The present invention relates to transgenic plants with increased organ size when compared to a non transformed plant of the same species. In one preferred embodiment, the present invention provides a transgenic plant with increased seed size when compared to a non transformed plant of the same species.

One embodiment of the invention provides a method of increasing seed and organ size of a plant by transforming the plant with a DNA construct comprising a promoter that functions in plants, operably linked to a DNA molecule that encodes a protein, where in said DNA molecule is selected from the from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, and SEQ ID NO: 70 and wherein said promoter is heterologous to said DNA molecule. The method also includes the DNA construct operably linked to a 3' termination region and selecting a desired plant from a population of transformed plants containing said DNA construct; wherein said desired plant exhibits increased seed and organ size compared to a plant of a same plant species not transformed to contain said DNA construct. The method may also encompass various promoters is including a caulimovirus promoter, or a heterologous plant constitutive promoter, or a tissue specific or an organ enhanced promoter.

In another embodiment, the present invention provides a method for increasing seed and other plant organ sizes by transforming a plant with a DNA construct comprising a promoter that functions in plants, operably linked to a DNA molecule that encodes a protein, wherein said protein comprises at least an N-terminal 50% portion of a polypeptide selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, and SEQ ID NO: 71 wherein said DNA construct is operably linked to a 3'termination region; and selecting a plant from a population of transformed plants containing said DNA construct; wherein said plant exhibits increased seed and organ size compared to a plant of a same species not transformed to contain said DNA construct. In a further embodiment, the present invention provides an isolated DNA construct comprising a promoter capable of functioning in a plant cell, operably linked to a structural nucleic acid sequence encoding SEQ ID NO: 2 or SEQ ID NO: 4, and a 3' non translated nucleic acid sequence capable of causing transcriptional termination and the addition of polyadenylated nucleotides to the 3' end of the transcribed mRNA sequence. This nucleic acid sequence may optionally include an intron, a 5' untranslated leader sequence or another nucleic acid sequence designed to enhance transcription and/or translation.

Another aspect of the present invention provides a method for improving the seed and organ size in a plant comprising the steps of:

(a) inserting into the genome of a plant a DNA construct comprising in the 5' to 3' direction:

(i) a promoter that functions in the cell of a selected plant tissue operably linked to;

(ii) a structural nucleic acid sequence that encodes a protein product selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, and SEQ ID NO: 71 operably linked to (iii) a 3' non translated nucleic acid sequences that functions in a plant cell to cause transcriptional termination and addition of polyadenylated nucleotides to the 3' end of an RNA sequence;

(b) obtaining transformed plant cells containing the nucleic acid of step (a); and (c) regenerating from transformed plant cells a transformed plant that over-expresses the gene product in the plant cell.

One aspect of invention provides a transgenic plant with increased seed and organ size when compared to a non transformed plant of a same plant species, said transgenic plant comprising a DNA construct, wherein said DNA construct comprises a promoter that functions in plants, operably linked to a DNA molecule that encodes a protein, wherein said DNA molecule is selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, and SEQ ID NO: 70 operably linked to a 3'termination region, wherein said promoter is heterologus to said DNA molecules.

Another aspect of invention provides a transgenic plant with increased seed and organ size when compared to a non transformed plant of a same plant species, the transgenic plant comprising a DNA construct, wherein said DNA construct encodes a protein that comprises at least an N-terminal 50% portion selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, and SEQ ID NO: 71.

Yet another aspect of the present invention provides a DNA construct comprising a promoter operably linked to an isolated nucleic acid molecule comprising a nucleotide sequence or complement thereof, wherein the nucleotide sequence encodes a polypeptide having an amino acid sequence that has at least 50% sequence identity, preferably at least 60%, more preferably at least 70% sequence identity, even more preferably at least 80% or 90% sequence identity, and most preferably at least 95% to 98% sequence identity to a polypeptide selected from group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, SEQ ID NO: 71 where in said promoter is heterologus to the said nucleic acid molecules.

BRIEF DESCRIPTION OF THE FIGURES

FIG. 10 shows primers used for amplification of gene and for sequencing of amplicons.

DETAILED DESCRIPTION OF THE INVENTION

Figure 1:
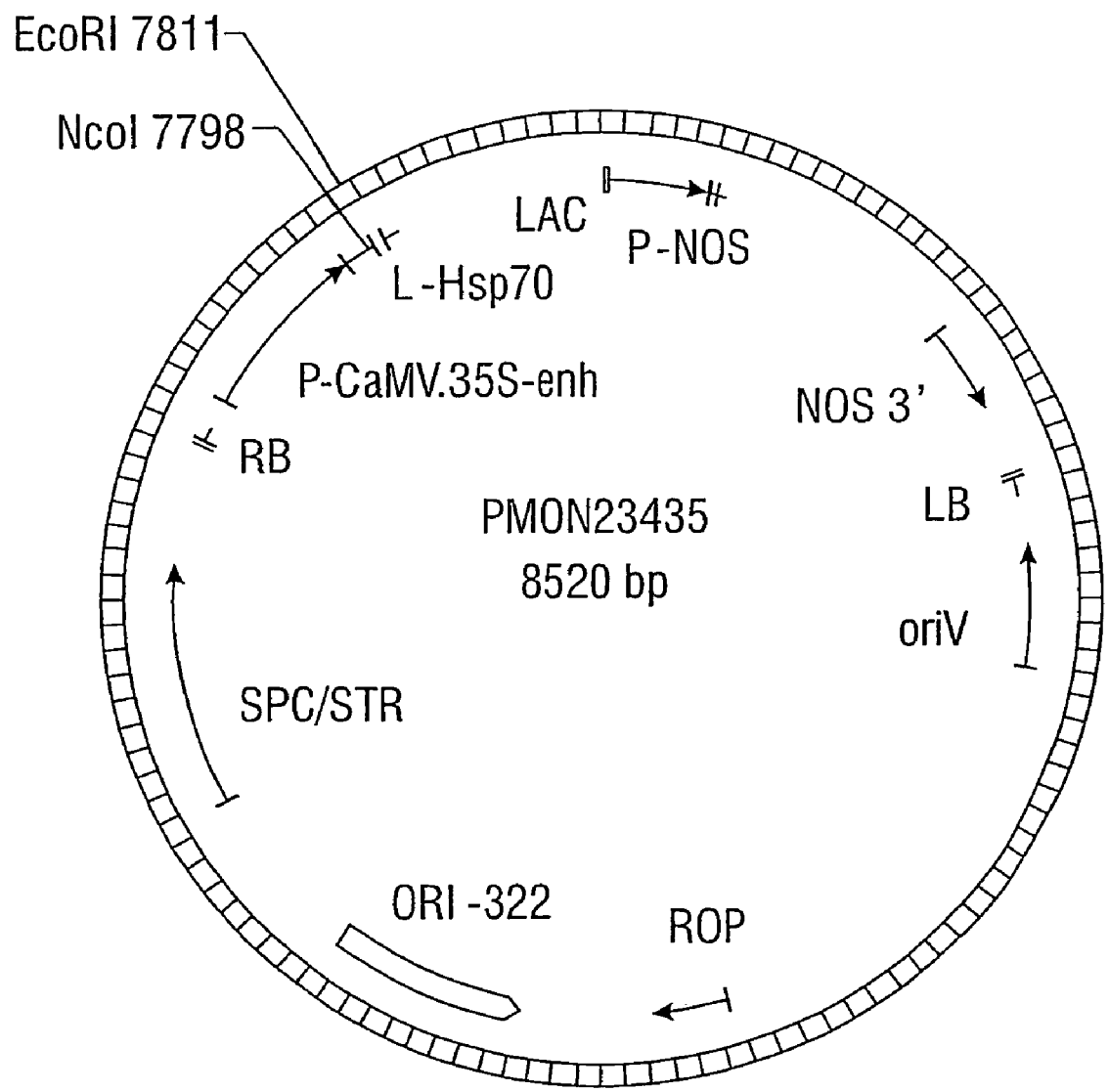
FIG. 1 shows a plasmid map for plant transformation vector pMON 23435 with its elements.

Isolated Nucleic Acid Molecules of the Present Invention

The present invention provides a method of increasing seed and organ size of a plant by transforming the plant with a DNA construct comprising a promoter that functions in plants, operably linked to a DNA molecule that encodes a protein, where in said DNA molecule is selected from the from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, SEQ ID NO: 70 and wherein said promoter is heterologous to said DNA molecule.

In another embodiment, the present invention provides a method for increasing seed and other plant organ sizes by transforming a plant with a DNA construct comprising a promoter that functions in plants, operably linked to a DNA molecule that encodes a protein, wherein said protein comprises at least an N-terminal 50% portion of a polypeptide selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, or SEQ ID NO: 71 operably linked to a 3'termination region.

The term "nucleic acid molecule" as used herein means a deoxyribonucleic acid (DNA) molecule or ribonucleic acid (RNA) molecule. Both DNA and RNA molecules are constructed from nucleotides linked end to end, wherein each of the nucleotides contains a phosphate group; a sugar moiety, and either a purine or a pyrimidine base. Nucleic acid molecules can be a single or double-stranded polymer of nucleotides read from the 5' to the 3' end. Nucleic acid molecules may also optionally contain synthetic, non-natural or altered nucleotide bases that permit correct read through by a polymerase and do not alter expression of a polypeptide encoded by that nucleic acid molecule.

The term "an isolated nucleic acid molecule" as used herein means a nucleic acid molecule that is no longer accompanied by some of materials with which it is associated in its natural state or to a nucleic acid molecule the structure of which is not identical to that of any of naturally occurring nucleic acid molecule. Examples of an isolated nucleic acid molecule include: (1) DNAs which have the sequence of part of a naturally occurring genomic DNA molecule but are not flanked by two coding sequences that flank that part of the molecule in the genome of the organism in which it naturally occurs; (2) a nucleic acid molecule incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. An isolated nucleic acid molecule may also be comprised of one or more segments of cDNA, genomic DNA or synthetic DNA.

It is also contemplated by the inventors that the isolated nucleic acid molecules of the present invention also include known types of modifications, for example, labels which are known in the art, methylation, "caps", substitution of one or more of the naturally occurring nucleotides with an analog. Other known modifications include internucleotide modifications, for example, those with uncharged linkages (methyl phosphonates, phosphotriesters, phosphoamidates, carbamates, etc.) and with charged linkages (phosphorothioates, phosphorodithioates, etc.), those containing pendant moieties, such as, proteins (including nucleases, toxins, antibodies, signal peptides, poly-L-lysine, etc.), those with intercalators (acridine, psoralen, etc.), those containing chelators (metals, radioactive metals, boron, oxidative metals, etc.), those containing alkylators, and those with modified linkages.

The term "nucleotide sequence" as used herein means the order contiguous of nucleic acid molecule of both the sense and antisense strands or as a duplex strand. It includes, but is not limited to, self-replicating plasmids, synthetic polynucleotides, chromosomal sequences, and infectious polymers of DNA or RNA.

A nucleotide sequence is said to be the "complement" of another nucleotide sequence if they exhibit complete complementarity. As used herein, molecules are said to exhibit "complete complementarity" when every nucleotide of one of the sequences is complementary to a nucleotide of the other.

As used herein both terms "a coding sequence" and "a structural nucleotide sequence" mean a nucleotide sequence, which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, and recombinant nucleotide sequences.

The polypeptides of the invention, like other polypeptides, have different domains which perform different functions. Thus, the coding sequences need not be full length, so long as the desired functional domain of the polypeptide is expressed. The distinguishing features of polypeptides of the present invention are discussed in detail in Examples.

The term "recombinant DNAs" as used herein means DNAs that contains a genetically engineered modification through manipulation via mutagenesis, restriction enzymes, and the like.

The term "synthetic DNAs" as used herein means DNAs assembled from oligonucleotide building blocks that are chemically synthesized using procedures known to those skilled in the art. These building blocks are ligated and annealed to form DNA segments, which are then enzymatically assembled to construct the entire DNA. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines.

Both terms "polypeptide" and "protein", as used herein, mean a polymer composed of amino acids connected by peptide bonds. An amino acid unit in a polypeptide (or protein) is called a residue. The terms "polypeptide" and "protein" also applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a polypeptide, that polypeptide is specifically reactive to antibodies elicited to the same polypeptide but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties,* 2nd ed., T. E. Creighton, W. H. Freeman and Company, New York (1993), herein incorporated by reference in its entirety. Many detailed reviews are available on this subject, such as, for example, those provided by Wold, F., Post-translational Protein Modifications. Perspectives and Prospects, pp. 1-12 in *Post-translational Covalent Modification of Proteins*, B. C. Johnson, Ed., Academic Press, New York (1983); Seifter et al., *Meth. Enzymol.* 182:626-M (1990) and Rattan et al., *Protein Synthesis: Post-translational Modifications and Aging, Ann. N.Y. Acad. Sci.* 663:48-62 (1992), herein incorporated by reference in their entirety. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine containing and the methionine-less amino terminal variants of the polypeptide of the invention. Thus, as used herein, the terms "protein" and "polypeptide" include any protein or polypeptide that is modified by any biological or non-biological process.

The terms "amino acid" and "amino acids" refer to all naturally occurring amino acids and, unless otherwise limited, known analogs of natural amino acids that can function in a similar manner as naturally occurring amino acids. This definition is meant to include norleucine, ornithine, homocysteine, and homoserine.

The term "amino acid sequence" means the sequence of amino acids in a polypeptide (or protein) that is written starting with the amino-terminal (N-terminal) residue and ending with the carboxyl-terminal (C-terminal) residue.

The term "an amino acid subsequence" means a portion of the amino acid sequence of a polypeptide. An amino acid subsequence generally has a length of 3 to 50 amino acid residues.

Both terms "substantially purified polypeptide" and "substantially purified protein", as used herein, means a polypeptide or protein that is separated substantially from all other molecules normally associated with it in its native state and is the predominant species present in a preparation. A substantially purified molecule may be greater than 60% free, preferably 75% free, more preferably 90% free, and most preferably 95% free from the other molecules (exclusive of solvent) present in the natural mixture.

Percentage of sequence identity is determined by comparing two optimally aligned sequences over a comparison window, wherein the portion of the polynucleotide or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identity" refers to amino acid or nucleic acid sequences that when compared using the local homology algorithm of Smith and Waterman (T. F. Smith and M. S. Waterman, J. Mol. Biol. (147) 195-197 (1981). in the SSEARCH3 3.0t75 (W. R. Pearson, Genomics (11)635-650 (1991) or BLAST 2.2.1 (Altschul, Stephen F., Thomas L. Madden, Alejandro A. Schaffer, Jinghui Zhang, Zheng Zhang, Webb Miller, and David J. Lipman, Nucleic Acids Res. (25)3389-3402 (1997) programs which are exactly alike.

The term "similarity" refers to two amino acids, which are similar as defined by a similarity matrix BLOSSUM62 (S. Henikoff and J. G. Henikoff, Proc. Natl. Acad. Sci. U.S.A. (89) 10915-10919 (1992) which is used in BLAST 2.2.1 (Altschul, Stephen F., Thomas L. Madden, Alejandro A. Schaffer, Jinghui Zhang, Zheng Zhang, Webb Miller, and David J. Lipman, Nucleic Acids Res. (25)3389-3402 (1997). The BLAST uses alias "positive" for similarity. These two terms, similarity and positive-ness, are interchangeable.

The term "percent identity" for a pair of protein sequences refers to the number of identical amino acid residues in a two-sequence alignment reported by BLAST, divided by the total number of amino acid residues in the same alignment, expressed in percentage.

The term "percent similarity" for a pair of protein sequences refers to the number of similar ("Positive" in BLAST output) amino acid residues in a two-sequence alignment reported by BLAST, divided by the total number of amino acid residues in the same alignment, expressed in percentage.

Both terms "substantially identical" and "substantial identity", as reference to two amino acid sequences or two nucleotide sequences, means that one amino acid sequence or one nucleotide sequence has at least 50% sequence identity compared to the other amino acid sequence or nucleotide sequence as a reference sequence using the Gap program in the WISCONSIN PACKAGE version 10.0-UNIX from Genetics Computer Group, Inc. based on the method of Needleman and Wunsch (J. Mol. Biol. 48:443-453 (1970), herein incorporated by reference in its entirety) using the set of default parameters for pair-wise comparison (for amino acid sequence comparison: Gap Creation Penalty=8, Gap Extension Penalty=2; for nucleotide sequence comparison: Gap Creation Penalty=50; Gap Extension Penalty=3).

Polypeptides, which are "substantially similar" share sequences as noted above except that residue positions which are not identical may differ by conservative amino acid changes. Conservative amino acid substitutions refer to the interchangeability of residues having similar side chains. "Conservative amino acid substitutions" mean substitutions of one or more amino acids in a native amino acid sequence with another amino acid(s) having similar side chains, resulting in a silent change. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine, valine-isoleucine, phenylalanine-tyrosine, lysine-arginine, alanine-valine, aspartic acid-glutamic acid, and asparagine-glutamine.

One skilled in the art will recognize that the values of the above substantial identity of nucleotide sequences can be appropriately adjusted to determine corresponding sequence identity of two nucleotide sequences encoding the polypeptides of the present invention by taking into account codon degeneracy, conservative amino acid substitutions, reading frame positioning and the like. Substantial identity of nucleotide sequences for these purposes normally means sequence identity of at least 35%.

The term "codon degeneracy" means divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for ectopic expression in a host cell, it is desirable to design the gene such that its frequency of codon usage approaches the frequency of preferred codon usage of the host cell.

In another aspect, the present invention provides an isolated nucleic acid molecule in a DNA construct comprising a promoter operably linked to nucleotide sequence or complement thereof, wherein the nucleotide sequence hybridizes under stringent conditions to the complement of a second nucleotide sequence encoding a polypeptide having an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, and SEQ ID NO: 71.

The present invention also provides a method for obtaining an isolated nucleic acid molecule of the present invention, the method comprising the steps of: (a) probing a cDNA or genomic library with a hybridization probe comprising a nucleotide sequence encoding all or a portion of the amino acid sequence of a polypeptide, wherein the amino acid sequence of the polypeptide is selected from the group consisting of SEQ ID NO: 2, SEQ ID NO: 4, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 52, SEQ ID NO: 54, SEQ ID NO: 67, SEQ ID NO: 69, and SEQ ID NO: 71 (b) identifying a DNA clone that hybridizes under stringent conditions to hybridization probe; (c) isolating the DNA clone identified in step (b); and (d) sequencing the cDNA insert or genomic fragment contained in the DNA clone isolated in step (c) wherein the sequenced nucleic acid molecule encodes all or a substantial portion of the amino acid sequence of the present invention.

Hybridization conditions are sequence dependent and will be different in different circumstances. As used herein "stringent conditions" are selected to be about 5° C. lower than the thermal melting point (Tm) for the specific sequence at a defined ionic strength and pH. The "thermal melting point" is the temperature (under defined ionic strength and pH) at which 50% of a target molecule hybridizes to a completely complementary molecule. Appropriate stringent conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6, incorporated herein by reference in its entirety. For example, the salt concentration in the wash step can be selected from a low stringent condition of about 2.0×SSC at 50° C. to a high stringency of about 0.2×SSC at 50° C. In addition, the temperature in the wash step can be increased from low stringent conditions at room temperature, about 22° C., to high stringent conditions at about 65° C. Both temperature and salt concentration may be varied, or either the temperature or the salt concentration may be held constant while the other variable is changed. For the purposes of this disclosure, stringent conditions include at least one wash in 2.0× SSC at a temperature of at least about 50° C. for 20 minutes, or equivalent conditions.

The nucleic acid molecules of the present invention may be combined with other non-native, or "heterologous" sequences in a variety of ways. By "heterologous" sequences it is meant any sequence that is not naturally found joined to the nucleotide sequence encoding polypeptide of the present invention, including, for example, combinations of nucleotide sequences from the same plant which are not naturally found joined together, or the two sequences originate from two different species.

The term "homologous" refers to two or more genes that are derived from a single gene in a common ancestor. The term "homology is attributed to decent from a common ancestor. (J. J. Doyle and B. S. Gaut, Plant Molecular Biology (42)1-23, 2000.

The term "orthologous" refers to different homologous sequences in different species that arose from a common ancestral gene during speculation; may or may not be responsible for a similar function.

The term paralogous refers to homologous sequences within a single species that arose by gene duplication.

The term "domain" refers to a discrete portion of a protein assumed to fold independently of the rest of the protein and possessing its own function. Domain is also used to refer a discrete portion of nucleotide when translated provides a portion of protein which is assumed to fold independently of the rest of the translated nucleotide sequence and possessing its own function.

The term "Motif" refers to a short conserved region in a protein or nucleotide sequence. Motifs are frequently highly conserved parts of domains.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized.

The term "operably linked", as used in reference to a regulatory sequence and a structural nucleotide sequence, means that the regulatory sequence causes regulated expression of the operably linked structural nucleotide sequence. "Expression" means the transcription and stable accumulation of sense or antisense RNA derived from the nucleic acid molecule of the present invention. Expression may also refer to translation of mRNA into a polypeptide. "Sense" RNA means RNA transcript that includes the mRNA and so can be translated into polypeptide or protein by the cell. "Antisense RNA" means a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-translated sequence, introns, or the coding sequence. "RNA transcript" means the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

The term "overexpression" means the expression of a polypeptide encoded by an exogenous nucleic acid molecule introduced into a host cell, wherein said polypeptide is either not normally present in the host cell, or wherein said polypeptide is present in said host cell at a higher level than that normally expressed from the endogenous gene encoding said polypeptide.

By "ectopic expression" it is meant that expression of a nucleic acid molecule encoding a polypeptide in a cell type other than a cell type in which the nucleic acid molecule is normally expressed, at a time other than a time at which the nucleic acid molecule is normally expressed or at a expression level other than the level at which the nucleic acid molecule normally is expressed.

"Antisense inhibition" means the production of antisense RNA transcripts capable of suppressing the expression of the target polypeptide. "Co-suppression" means the production of sense RNA transcripts capable of suppressing the expression of identical or substantially similar foreign or endogenous genes (U.S. Pat. No. 5,231,020, incorporated herein by reference).

The term "a gene" means the segment of DNA that is involved in producing a polypeptide. Such segment of DNA includes regulatory sequences preceding (5' non-coding sequences) and following (3' non-coding sequences) the coding region as well as intervening sequences (introns) between individual coding segments (exons). A "Native gene" means a gene as found in nature with its own regulatory sequences. "Chimeric gene" means any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" or "endogenous DNA molecule" means a native gene in its natural location in the genome of an organism. A "foreign gene" means a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Regulatory sequences" mean nucleotide sequences located upstream (5' non-coding sequences), within, or downstream (3' non-translated sequences) of a structural nucleotide sequence, and which influence the transcription, RNA processing or stability, or translation of the associated structural nucleotide sequence. Regulatory sequences may include promoters, translation leader sequences, introns, and polyadenylation recognition sequences.

The term "promoter sequence" means a nucleotide sequence that is capable of, when located in cis to a structural nucleotide sequence encoding a polypeptide, functioning in a way that directs expression of one or more mRNA molecules that encodes the polypeptide. Such promoter regions are typically found upstream of the trinucleotide ATG sequence at the start site of a polypeptide-coding region. Promoter sequences can also include sequences from which transcription of transfer RNA (tRNA) or ribosomal RNA (rRNA) sequences are initiated. Transcription involves the synthesis of a RNA chain representing one strand of a DNA duplex. By "representing" it is meant that the RNA is identical in sequence with one strand of the DNA; it is complementary to the other DNA strand, which provides the template for its synthesis. Transcription takes place by the usual process of complementary base pairing, catalyzed and scrutinized by the enzyme RNA polymerase. The reaction can be divided into three stages described as initiation, elongation and termination. Initiation begins with the binding of RNA polymerase to the double stranded (DS or ds) DNA. The sequence of DNA required for the initiation reaction defines the promoter. The site at which the first nucleotide is incorporated is called the start-site or start-point of transcription. Elongation describes the phase during which the enzyme moves along the DNA and extends the growing RNA chain. Elongation involves the disruption of the DNA double stranded structure in which a transiently unwound region exists as a hybrid RNA-DNA duplex and a displaced single strand of DNA. Termination involves recognition of the point at which no further bases should be added to the chain. To terminate transcription, the formation of phosphodiester bonds must cease and the transcription complex must come apart. When the last base is added to the RNA chain, the RNA-DNA hybrid is disrupted, the DNA reforms into a duplex state, and the RNA polymerase enzyme and RNA molecule are both released from the DNA. The sequence of DNA required for the termination reaction is called the terminator.

The promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions.

Promoters, which are known or are found to cause transcription of DNA in plant cells, can be used in the present invention. Such promoters may be obtained from a variety of sources such as plants and plant viruses. A number of promoters, including constitutive promoters, inducible promoters and tissue-specific promoters, that are active in plant cells have been described in the literature. In addition to promoters that are known to cause transcription of DNA in plant cells, other promoters may be identified for use in the current invention by screening a plant cDNA library for genes that are selectively or preferably expressed in the target tissues and then determine the promoter regions.

The term "constitutive promoter" means a regulatory sequence which causes expression of a structural nucleotide sequence in most cells or tissues at most times. Constitutive promoters are active under most environmental conditions and states of development or cell differentiation. A variety of constitutive promoters are well known in the art. Examples of constitutive promoters that are active in plant cells include but are not limited to the nopaline synthase (NOS) promoters; DNA plant virus promoters including, but not limited to the caulimovirus promoters for example, cauliflower mosaic virus (CaMV) 19S and 35S, and figwort mosaic virus promoters; the bacilliform virus promoter for example sugar cane bacilliform virus, rice tungro bacilliform virus, among others; plant actin promoters, such as the *Arabidopsis* and rice actin gene promoter (see, e.g., Huang et al, *Plant Mol Biol.* 33:125-139 (1997), U.S. Pat. No. 5,641,876), herein incorporated by reference in its entirety). These promoters when used in a DNA construct are heterologous to the linked gene sequence when they are derived from a different organism, plant species, or a different gene.

The term "inducible promoter" means a regulatory sequence which causes conditional expression of a structural nucleotide sequence under the influence of changing environmental conditions or developmental conditions. Examples of inducible promoters include but are not limited to the senescence-induced promoter for the senescence-associated gene, SAG12, (Gan and Amasino, Science 270: 1986-1988 (1995), herein incorporated by reference in its entirety); the light-inducible promoter from the small subunit of ribulose-1,5-bis-phosphate carboxylase (ssRUBISCO); the drought-inducible promoter of maize (Busk et al., *Plant J.* 11:1285-1295 (1997), herein incorporated by reference in its entirety); the cold, drought, and high salt inducible promoter from potato (Kirch, *Plant Mol. Biol.* 33:897-909 (1997), herein incorporated by reference in its entirety); a nitrate-inducible promoter derived from the spinach nitrite reductase gene (Back et al., *Plant Mol. Biol.* 17:9 (1991), herein incorporated by its entirety); salicylic acid inducible promoter (Uknes et al., *Plant Cell* 5:159-169 (1993); Bi et al., *Plant J.* 8:235-245 (1995) herein incorporated by reference in their entireties); the auxin-response elements E1 promoter fragment (AuxREs) in the soybean (*Glycine max* L.) (Liu et al., *Plant Physiol* 115:397-407 (1997), herein incorporated by reference in its entirety); the auxin-responsive *Arabidopsis* GST6 promoter (also responsive to salicylic acid and hydrogen peroxide) (Chen et al., *Plant J.* 10: 955-966 (1996), herein incorporated by reference in its entirety); the auxin-inducible parc promoter from tobacco (Sakai et al., *Plant Cell Physiol.* 37:906-913 (1996), herein incorporated by reference in its entirety); a plant biotin response element (Streit et al., *Mol Plant Microbe Interact.* 10:933-937 (1997), herein incorporated by reference in its entirety); the promoter responsive to the stress hormone abscisic acid (Sheen et al., *Science* 274: 1900-1902 (1996), herein incorporated by reference in its entirety); the maize In2-2 promoter activated by benzenesulfonamide herbicide safeners (De Veylder et al, *Plant Cell Physiol.* 38:568-577 (1997), herein incorporated by reference in its entirety); a tetracycline-inducible promoter, such as the promoter for the *Avena sativa* L. (oat) arginine decarboxylase gene (Masgrau et al., *Plant J.* 11:465-473 (1997), herein incorporated by reference in its entirety); and a salicylic acid-responsive element (Stange et al., *Plant J.* 11:1315-1324 (1997), herein incorporated by reference in its entirety).

The term "tissue-specific promoter" or "organ enhanced promoter" means a regulatory sequence that causes transcriptions or enhanced transcriptions of DNA in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistols, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

A variety of promoters specifically active in, vegetative tissues, such as leaves, stems, roots and tubers, can be used to express the nucleic acid molecules of the present invention. Examples of tuber-specific promoters include but are not limited to the class I and II patatin promoters (Bevan et al., *EMBO J.* 8: 1899-1906 (1986); Koster-Topfer et al., *Mol Gen Genet.* 219: 390-396 (1989); Mignery et al., *Gene.* 62: 2744 (1988); Jefferson et al., *Plant Mol. Biol.* 14: 995-1006 (1990), herein incorporated by reference in their entireties), the promoter for the potato tuber ADPGPP genes, both the large and small subunits; the sucrose synthase promoter (Salanoubat and Belliard, *Gene.* 60: 47-56 (1987), Salanoubat and Belliard, *Gene.* 84: 181-185 (1989), herein incorporated by reference in their entirety); and the promoter for the major tuber proteins including the 22 kd protein complexes and proteinase inhibitors (Hannapel, *Plant Physiol.* 101: 703-704 (1993), herein incorporated by reference in its entirety). Examples of leaf-specific promoters include but are not limited to the ribulose biphosphate carboxylase (RBCS or RuBISCO) promoters (see, e.g., Matsuoka et al., *Plant J.* 6:311-319 (1994), herein incorporated by reference in its entirety); the light harvesting chlorophyll a/b binding protein gene promoter (see, e.g., Shiina et al., *Plant Physiol.* 115:477-483 (1997); Casal et al., *Plant Physiol.* 116:1533-1538 (1998), herein incorporated by reference in their entireties); and the *Arabidopsis thaliana* myb-related gene promoter (Atmyb5) (Li et al., *FEBS Lett.* 379:117-121 (1996), herein incorporated by reference in its entirety). Examples of root-specific promoter include but are not limited to the promoter for the acid chitinase gene (Samac et al., *Plant Mol. Biol.* 25: 587-596 (1994), herein incorporated by reference in its entirety); the root specific subdomains of the CaMV35S promoter that have been identified (Lam et al., *Proc. Natl. Acad. Sci.* (U.S.A)

86:7890-7894 (1989), herein incorporated by reference in its entirety); the ORF13 promoter from *Agrobacterium rhizogenes* which exhibits high activity in roots (Hansen et al., *Mol. Gen. Genet.* 254:337-343 (1997), herein incorporated by reference in its entirety); the promoter for the tobacco root-specific gene TobRB7 (Yamamoto et al., *Plant Cell* 3:371-382 (1991), herein incorporated by reference in its entirety); and the root cell specific promoters reported by Conkling et al. (Conkling et al., *Plant Physiol.* 93:1203-1211 (1990), herein incorporated by reference in its entirety). Another class of useful vegetative tissue-specific promoters is meristematic (root tip and shoot apex) promoters. For example, the "SHOOTMERISTEMLESS" and "SCARECROW" promoters, which are active in the developing shoot or root apical meristems (Di Laurenzio et al., *Cell* 86:423-433 (1996); Long, *Nature* 379:66-69 (1996); herein incorporated by reference in their entireties), can be used. Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto et al., *Plant Cell.* 7:517-527 (1995), herein incorporated by reference in its entirety). Also another example of a useful promoter is that which controls the expression of knl-related genes from maize and other species which show meristem-specific expression (see, e.g., Granger et al., *Plant Mol. Biol.* 31:373-378 (1996); Kerstetter et al., *Plant Cell* 6:1877-1887 (1994); Hake et al., *Philos. Trans. R. Soc. Lond. B. Biol. Sci* 350:45-51 (1995), herein incorporated by reference in their entireties). Another example of a meristematic promoter is the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln et al., *Plant Cell* 6:1859-1876 (1994), herein incorporated by reference in its entirety).

Suitable seed-specific promoters can be derived from the following genes: MAC1 from maize (Sheridan et al., *Genetics* 142:1009-1020 (1996), herein incorporated by reference in its entirety); Cat3 from maize (GenBank No. L05934, Abler et al., *Plant Mol. Biol.* 22:10131-1038 (1993), herein incorporated by reference in its entirety); vivparous-1 from *Arabidopsis* (Genbank No. U93215); Atimyc1 from *Arabidopsis* (Urao et al., *Plant Mol. Biol.* 32:571-57 (1996); Conceicao et al., *Plant* 5:493-505 (1994), herein incorporated by reference in their entireties); napA from *Brassica napus* (GenBank No. J02798); the napin gene family from *Brassica napus* (Sjodahl et al., *Planta* 197:264-271 (1995), herein incorporated by reference in its entirety).

The ovule-specific promoter for BEL1 gene (Reiser et al. *Cell* 83:735-742 (1995), GenBank No. U39944; Ray et al, *Proc. Natl. Acad. Sci. USA* 91:5761-5765 (1994), all of which are herein incorporated by reference in their entireties) can also be used. The egg and central cell specific MEA (FIS1) and FIS2 promoters are also useful reproductive tissue-specific promoters (Luo et al., *Proc. Natl. Acad. Sci. USA*, 97:10637-10642 (2000); Vielle-Calzada, et al., *Genes Dev.* 13:2971-2982 (1999); herein incorporated by reference in their entireties).

A maize pollen-specific promoter has been identified in maize (Guerrero et al., Mol. Gen. Genet. 224:161-168 (1990), herein incorporated by reference in its entirety). Other genes specifically expressed in pollen have been described (see, e.g., Wakeley et al., Plant Mol. Biol. 37:187-192 (1998); Ficker et al., Mol. Gen. Genet. 257:132-142 (1998); Kulikauskas et al., Plant Mol. Biol. 34:809-814 (1997); Treacy et al., Plant Mol. Biol. 34:603-611 (1997); all of which are herein incorporated by reference in their entireties).

Promoters derived from genes encoding embryonic storage proteins, which includes the gene encoding the 2S storage protein from *Brassica napus* (Dasgupta et al, Gene 133:301-302 (1993), herein incorporated by reference in its entirety); the 2S seed storage protein gene family from *Arabidopsis*; the gene encoding oleosin 20 kD from *Brassica napus* (GenBank No. M63985); the genes encoding oleosin A (GenBank No. U09118) and oleosin B (GenBank No. U09119) from soybean; the gene encoding oleosin from *Arabidopsis* (GenBank No. Z17657); the gene encoding oleosin 18 kD from maize (GenBank No. J05212, Lee, Plant Mol. Biol. 26:1981-1987 (1994), herein incorporated by reference in its entirety); and the gene encoding low molecular weight sulphur rich protein from soybean (Choi et al., Mol. Gen. Genet. 246:266-268 (1995), herein incorporated by reference in its entirety), can also be used.

Promoters derived from zein encoding genes (including the 15 kD, 16 kD, 19 kD, 22 kD, 27 kD, and gamma genes) (Pedersen et al., *Cell* 29: 1015-1026 (1982), herein incorporated by reference in its entirety) can be also used. The zeins are a group of storage proteins found in maize endosperm.

Other promoters known to function, for example, in maize, include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., *Mol. Cell. Biol.* 13: 5829-5842 (1993), herein incorporated by reference in its entirety). Examples of promoters suitable for expression in wheat include those promoters for the ADPglucose pyrophosphorylase (ADPGPP) subunits, the granule bound and other starch synthases, the branching and debranching enzymes, the embryogenesis-abundant proteins, the gliadins, and the glutenins. Examples of such promoters in rice include those promoters for the ADPGPP subunits, the granule bound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleurone specific proteins.

A tomato promoter active during fruit ripening, senescence and abscission of leaves and, to a lesser extent, of flowers can be used (Blume et al., *Plant J.* 12:731-746 (1997), herein incorporated by reference in its entirety). Other exemplary promoters include the pistol specific promoter in the potato (*Solarium tuberosum* L.) SK2 gene, encoding a pistil-specific basic endochitinase (Ficker et al., *Plant Mol. Biol.* 35:425-431 (1997), herein incorporated by reference in its entirety); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots. The tissue specific E8 promoter from tomato is also useful for directing gene expression in fruits.

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., *The Plant Cell* 1:977-984 (1989), herein incorporated by reference in its entirety). It is further recognized that since in most cases the exact boundaries of regulatory sequences have not been completely defined, DNA fragments of different lengths may have identical promoter activity.

The "translation leader sequence" means a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (U.S. Pat. No. 5,659,122 and Turner and Foster, *Molecular Biotechnology* 3:225 (1995) herein incorporated by reference in its entirety).

The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (NOS 3'; Fraley et al., *Proc. Natl. Acad. Sci. USA* 80: 4803-4807 (1983), herein incorporated by reference in its entirety). The use of different 3' non-translated sequences is exemplified by Ingelbrecht et al., *Plant Cell* 1:671-680 (1989), herein incorporated by reference in its entirety.

The isolated nucleic acid molecules of the present invention may also include introns. Generally, optimal expression in monocotyledonous and some dicotyledonous plants is obtained when an intron sequence is inserted between the promoter sequence and the structural gene sequence or, optionally, may be inserted in the structural coding sequence to provide an interrupted coding sequence. An example of such an intron sequence is the HSP 70 intron described in WO 93/19189, herein incorporated by reference in its entirety.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989).

Isolation and identification of nucleic acid molecules encoding polypeptides of the present invention from soybean, corn, rice and other species are described in detail in Examples. All or a substantial portion of the nucleic acid molecules of the present invention may be used to isolate cDNAs and nucleic acid molecules encoding homologous polypeptides from the same or other plant species.

A "substantial portion" of a nucleotide sequence comprises enough of the sequence to afford specific identification and/or isolation of a nucleic acid molecule comprising the sequence. Nucleotide sequences can be evaluated either manually by one skilled in the art, or by using computer-based sequence comparison and identification tools that employ algorithms such as BLAST (Basic Local Alignment Search Tool; Altschul et al. *J Mol. Biol.* 215:403-410 (1993). In general, a sequence of thirty or more contiguous nucleotides is necessary in order to putatively identify a nucleotide sequence as homologous to a gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid molecule comprising the primers. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Isolation of nucleic acid molecules encoding homologous polypeptides using sequence-dependent protocols is well known in the art. Examples of sequence-dependent protocols include, but are not limited to, methods of nucleic acid molecule hybridization, and methods of DNA and RNA amplification as exemplified by various uses of nucleic acid molecule amplification technologies (e.g., polymerase chain reaction, ligase chain reaction).

For example, structural nucleic acid molecules encoding other polypeptide of the present invention, either as cDNAs or genomic DNAs, could be isolated directly by using all or a substantial portion of the nucleic acid molecules of the present invention as DNA hybridization probes to screen cDNA or genomic libraries from any desired plant employing methodology well known to those skilled in the art. Methods for forming such libraries are well known in the art. Specific oligonucleotide probes based upon the nucleic acid molecules of the present invention can be designed and synthesized by methods known in the art. Moreover, the entire sequences of the nucleic acid molecules can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after is amplification reactions, and used as probes to isolate full-length cDNA or genomic DNAs under conditions of appropriate stringency.

Alternatively, the nucleic acid molecules of interest can be amplified from nucleic acid samples using amplification techniques. For instance, the disclosed nucleic acid molecules may be used to define a pair of primers that can be used with the polymerase chain reaction (Mullis, et al., *Cold Spring Harbor Symp. Quant. Biol.* 51:263-273 (1986); Erlich et al., EP 50,424; EP 84,796, EP 258,017, EP 237,362; Mullis, EP 201,184; Mullis et al., U.S. Pat. No. 4,683,202; Erlich, U.S. Pat. No. 4,582,788; and Saiki, R. et al., U.S. Pat. No. 4,683,194, all of which are herein incorporated by reference in their entireties) to amplify and obtain any desired nucleic acid molecule directly from mRNA, from cDNA, from genomic libraries or cDNA libraries. PCR and other in vitro amplification methods may also be useful, for example, to clone nucleotide sequences that encode for polypeptides to be expressed, to make nucleic acid molecules to use as probes for detecting the presence of the desired mRNA in samples, for nucleic acid sequencing, or for other purposes. In addition, two short segments of the nucleic acid molecules of the present invention may be used in polymerase chain reaction protocols to amplify longer nucleic acid molecules encoding homologues of a polypeptide of the present invention from DNA or RNA. For example, the skilled artisan can follow the RACE protocol (Frohman et al., Proc. Natl. Acad. Sci. USA 85:8998 (1988), herein incorporated by reference in its entirety) to generate cDNAs by using PCR to amplify copies of the region between a single point in the transcript and the 3' or 5' end. Primers oriented in the 3' and 5' directions can be designed from the nucleic acid molecules of the present invention. Using commercially available 3'RACE or 5'RACE systems (Gibco BRL, Life Technologies, Gaithersburg, Md. U.S.A.), specific 3' or 5' cDNA fragments can be isolated (Ohara et al., Proc. Natl. Acad. Sci. USA 86:5673 (1989); Loh et al., Science 243:217 (1989), both of which are herein incorporated by reference in their entireties). Products generated by the 3' and 5' RACE procedures can be combined to generate full-length cDNAs (Frohman and Martin, Techniques.1: 165 (1989), herein incorporated by reference in its entirety).

Nucleic acid molecules of interest may also be synthesized, either completely or in part, especially where it is desirable to provide plant-preferred sequences, by well-known techniques as described in the technical literature. See, e.g., Carruthers et al., Cold Spring Harbor Symp. Quant. Biol. 47:411-418 (1982), and Adams et al., J. Am. Chem. Soc. 105:661 (1983), both of which are herein incorporated by reference in their entireties. Thus, all or a portion of the nucleic is acid molecules of the present invention may be synthesized using codons preferred by a selected plant host. Plant-preferred codons may be determined, for example, from the codons used most frequently in the proteins expressed in a particular plant host species. Other modifications of the gene sequences may result in mutants having slightly altered activity Availability of the nucleotide sequences encoding polypeptide of the present invention facilitates immunological screening of cDNA expression libraries. Synthetic polypeptides representing portions of the amino acid sequences of polypeptides of the present invention may be synthesized. These polypeptides can be used to immunize animals to produce polyclonal or monoclonal antibodies with specificity for polypeptides comprising the amino acid sequences. These antibodies can be then be used to screen cDNA expression libraries to isolate full-length cDNA clones of interest (Lerner, Adv. Immunol. 36: 1 (1984); Sambrook et al., Molecular Cloning: A Laboratory Manual; Cold Spring Harbor Laboratory Press: Cold Spring Harbor, (1989)). It is understood that people skilled in the art are familiar with the standard resource materials which describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y. (1988)).

Another aspect of the present invention relates to methods of making a DNA construct by obtaining a nucleic acid molecule comprising a nucleotide sequence encoding a polypeptide of the present invention, the amino acid sequence of which has at least 50% sequence identity to a polypeptide selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO:54, SEQ ID NO: 67, SEQ ID NO: 69, and SEQ ID NO: 71.

One aspect of the present invention provides an isolated nucleic acid molecule comprising a nucleotide sequence or complement thereof, wherein the nucleotide sequence encodes a polypeptide having an amino acid sequence that has at least 50% sequence identity, preferably at least 60%, more preferably at least 70% sequence identity, even more preferably at least 80% or 90% sequence identity, and most preferably at least 95% to 98% sequence identity to a polypeptide selected from group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, and SEQ ID NO: 71.

One method of the present invention is for obtaining a nucleic acid molecule encoding all or a substantial portion of the amino acid sequence of a polypeptide of the present invention comprising: (a) probing a cDNA or genomic library with a hybridization probe comprising a nucleotide sequence encoding all or a substantial portion of a polypeptide having an amino acid sequence set forth in any of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, SEQ ID NO: 71 or an amino acid sequence set forth in any of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, SEQ ID NO: 71 with conservative amino acid substitutions; (b) identifying a DNA clone that hybridizes under stringent conditions to the hybridization probe; (c) isolating the DNA clone identified in step (b); and (d) sequencing the cDNA or genomic fragment that comprises the clone isolated in step (c) wherein the sequenced nucleic acid molecule encodes all or a substantial portion of the amino acid sequence of polypeptide of the present invention.

Another method of the present invention for obtaining a nucleic acid molecule encoding all or a substantial portion of the amino acid sequence of a polypeptide of the present invention comprising: (a) synthesizing a first and a second oligonucleotide primers, wherein the sequences of the first and second oligonucleotide primers encode two different portions of a polypeptide having an amino acid sequence selected from the group consisting of SEQ ID NO: 2, SEQ ID NO: 4, SEQ ED NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, SEQ ID NO: 71; and (b) amplifying and obtaining the nucleic acid molecule directly from mRNA samples, from genomic libraries or from cDNA libraries using the first and second oligonucleotide primers of step (a) wherein the nucleic acid molecule encodes all or a substantial portion of the amino acid sequence polypeptide of the present invention.

All or a substantial portion of the nucleic acid molecules of the present invention may also be used as probes for genetically and physically mapping the genes that they are a part of, and as markers for traits linked to those genes. Such information may be useful in plant breeding in order to develop lines with desired phenotypes. For example, the nucleic acid molecules of the present invention may be used as restriction fragment length polymorphism (RFLP) markers. Southern blots (Maniatis et al., *Molecular Cloning: A Laboratory Manual*, Second Edition (1989) Cold Spring Harbor Laboratory, Cold Spring Harbor, N.Y., herein incorporated by reference in its entirety) of restriction-digested plant genomic DNA may be probed with the nucleic acid fragments of the present invention. The resulting banding patterns may then be subjected to genetic analyses using computer programs such as MapMaker (Lander et al., *Genomics* 1: 174-181 (1987), herein incorporated by reference in its entirety) in order to construct a genetic map. In addition, the nucleic acid fragments of the present invention may be used to probe Southern blots containing restriction endonuclease-treated genomic DNAs of a set of individuals representing parent and progeny of a defined genetic cross. Segregation of the DNA polymorphisms is noted and used to calculate the position of the nucleotide sequence of the present invention in the genetic map previously obtained using this population (Botstein et al., *Am. J. Hum. Genet.* 32:314-331 (1980), herein incorporated by reference in its entirety).

The production and use of plant gene-derived probes for use in genetic mapping is described in Bernatzky and Tanksley, *Plant Mol. Biol. Reporter* 4:37-41 (1986), herein incorporated by reference in its entirety. Numerous publications describe genetic mapping of specific cDNA clones using the methodology outlined above or variations thereof. For example, F2 intercross populations, backcross populations, randomly mated populations, near isogenic lines, exotic germplasms, and other sets of individuals may be used for mapping. Such methodologies are well known to those skilled in the art.

Nucleic acid probes derived from the nucleic acid molecules of the present invention may also be used for physical mapping (i.e., placement of sequences on physical maps; see Hoheisel et al., In: Nonmammalian Genomic Analysis: A Practical Guide, Academic press 1996, pp. 319-346, and references cited therein).

In another embodiment, nucleic acid probes derived from the nucleic acid molecules of the present invention may be used in direct fluorescence in siti hybridization (FISH) mapping (Trask, *Trends Genet.* 7:149-154 (1991), herein incorporated by reference in its entirety). Although current methods of FISH mapping favor use of large clones (several to several hundred KB; see Laan et al., *Genome Res.* 5:13-20 (1995), herein incorporated by reference in its entirety), improvements in sensitivity may allow performance of FISH mapping using shorter probes.

A variety of nucleic acid amplification-based methods of genetic and physical mapping may be carried out using the nucleotide molecules of the present invention. Examples include allele-specific amplification (Kazazian et al., *J. Lab. Clin. Med.* 11:95-96 (1989), herein incorporated by reference in its entirety), polymorphism of PCR-amplified fragments (CAPS; Sheffield et al., *Genomics* 16:325-332 (1993), herein incorporated by reference in its entirety), allele-specific ligation (Landegren et al., *Science* 241:1077-1080 (1988) herein incorporated by reference in its entirety), nucleotide extension reactions (Sokolov et al., *Nucleic Acid Res.* 18:3671 (1990) herein incorporated by reference in its entirety), Radiation Hybrid Mapping (Walter et al., *Nat. Genet.* 7:22-28 (1997) herein incorporated by reference in its entirety) and Happy Mapping (Dear and Cook, *Nucleic Acid Res.* 17:6795-6807 (1989) herein incorporated by reference in its entirety). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the nucleotide sequence. This, however, is generally not necessary for mapping methods.

Isolated nucleic acid molecules of the present invention may find use in the identification is of loss of function mutant phenotypes of a plant, due to a mutation in one or more endogenous genes encoding polypeptides of the present invention. This can be accomplished either by using targeted gene disruption protocols or by identifying specific mutants for these genes contained in a population of plants carrying mutations in all possible genes (Ballinger and Benzer, *Proc. Natl. Acad Sci USA* 86:9402-9406 (1989); Koes et al, *Proc. Natl. Acad. Sci. USA* 92:8149-8153 (1995); Bensen et al., *Plant Cell* 7:75-84 (1995) all of which are incorporated herein by reference in their entirety). The latter approach may be accomplished in two ways. First, short segments of the nucleic acid molecules of the present invention may be used in polymerase chain reaction protocols in conjunction with a mutation tag sequence primer on DNAs prepared from a population of plants in which mutator transposons or some other mutation-causing DNA element has been introduced. The amplification of a specific DNA fragment with these primers indicates the insertion of the mutation tag element in or near the plant gene encoding polypeptide(s) of the present invention. Alternatively, the nucleic acid molecules of the present invention may be used as a hybridization probe against PCR amplification products generated from the mutation population using the mutation tag sequence primer in conjunction with an arbitrary genomic site primer, such as that for a restriction enzyme site-anchored synthetic adapter. Isolated nucleic acid molecules of the present invention can be mutated by a variety of methods well known in the art (Shortle D. et al., Annu. Rev. Genet. 15: 265, 1981; Itakura K. et al., Ann Rev. Biochem 53: 323, 1984; Botstein D. & Shortle D., Science 229: 1193, 1985; Smith M., Ann. Rev. Genet. 19: 423 1985; and Sambrook, et al., In: *Molecular Cloning, A Laboratory Manual,* 2nd Edition, Cold Spring Harbor Press, Cold Spring Harbor, N.Y. 1989, herein incorporated by reference in its entirety). These mutations can also be introduced by causing point mutation or site directed mutagenesis by using commercially available kits such as QuickChange™ from Stratagene (11011 North Torrey Pines Road, La Jolla, Calif. 92037). For example site directed mutations can include but are not limited to, truncations, substitutions, additions, terminations, fusions of polypeptides or nucleic acid. With either method, a plant containing a mutation in the endogenous gene encoding polypeptides of the present invention can be identified and obtained. Such plant can also be obtained by in situ site directed mutagenesis. This mutant plant can then be used to determine or confirm the natural function of the polypeptides of the present invention disclosed herein.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

"C-terminal region" refers to the region of a peptide, polypeptide, or protein chain from the middle thereof to the end that carries the amino acid having a free carboxyl group.

"N-terminal region" refers to the region of a peptide, polypeptide, or protein chain from the amino acid having a free amino group to the middle of the chain.

Antisense Oligonucleotides or Polynucleotides of the Present Invention

The present invention, in another aspect, provides an antisense oligonucleotide or polynucleotide encoding an RNA molecule which hybridizes to at least a portion of an RNA transcript of an endogenous gene encoding a polypeptide of the present invention, wherein the RNA molecule hybridizes with the RNA transcript such that expression of the endogenous gene is altered.

The present invention, in another aspect, provides DNA construct wherein a promoter that functions in plant is operably linked to an antisense oligonucleotide or polynucleotide encoding an RNA molecule which hybridizes under stringent hybridization conditions to at least a portion of an RNA transcript of an endogenous gene encoding a polypeptide the amino acid sequence of which has at least 50% sequence identity to a member selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 67, SEQ ID NO: 69, and SEQ ID NO: 71. The antisense oligonucleotide or polynucleotide can be full length or preferably has about six to about 100 nucleotides. In one embodiment of this invention, the antisense oligonucleotide or polynucleotide hybridizes under stringent conditions to either at least a corresponding portion of one strand of a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, SEQ ID NO: 70, or the RNA transcript transcribed from the a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53 SEQ ID NO: 66, SEQ ID NO: 68, and SEQ ID NO: 70. In another embodiment, the antisense oligonucleotide or polynucleotide hybridizes under stringent conditions to a corresponding portion of the 5' non-coding region or 3' non-translated region of the RNA transcript. In another embodiment, the antisense oligonucleotide or polynucleotide further comprises a sequence encoding a catalytic RNA or riboenzyme.

The antisense oligonucleotides or polynucleotides of the present invention may find particular use in antisense technology to suppress endogenous gene expression to control sizes of organs in transgenic plants. To accomplish this, a nucleic acid molecule derived from a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ED NO: 13, SEQ ID NO: 15, SEQ ID NO: 17, SEQ ID NO: 19, SEQ ID NO: 21, SEQ ED NO: 23, SEQ ID NO: 25, SEQ ID NO: 27, SEQ ID NO: 29, SEQ ED NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, and SEQ ID NO: 70 is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA that encodes the enzyme of interest (see, e.g., Sheehy et al., *Proc. Nat. Acad. Sci. USA* 85:8805-8809 (1988), and U.S. Pat. No. 4,801,340; both of which are herein incorporated by reference in their entireties).

The antisense oligonucleotide or polynucleotide to be introduced generally will be substantially identical to at least a portion of the endogenous gene or genes of the present invention to be repressed. The sequence, however, needs not to be perfectly identical to inhibit or suppress expression of the endogenous gene or genes of the present invention.

For antisense suppression, the introduced sequence also needs not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 6 nucleotides and about full length nucleotides should be used, though a sequence of at least about 500 to about 1700 nucleotides is preferred, a sequence of at least about 200 nucleotides is more preferred, and a sequence of about 6 to about 100 nucleotides is especially preferred.

In another embodiment of this invention, the antisense oligonucleotide or polynucleotide is substantially complementary to at least a corresponding portion of one strand of a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, SEQ ID NO: 70, or the RNA transcript transcribed from the a nucleotide sequence selected from the group consisting of SEQ ID NO: 1, SEQ ID NO: 3, SEQ ID NO:5, SEQ ID NO: 7, SEQ ID NO:9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, SEQ ID NO: 70. In another embodiment, the antisense oligonucleotide or polynucleotide is substantially complementary to a corresponding portion of the 5' non-coding portion or 3' non-coding portion of one strand of a DNA molecule which has substantial sequence identity to a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 66, SEQ ID NO: 68, or SEQ ID NO: 70.

The antisense oligonucleotides or polynucleotides of the present invention may further comprise a nucleotide sequence encoding a catalytic RNA molecule or a ribozyme. It is known to a skilled person in the art that catalytic RNA molecules or ribozymes can also be used to inhibit expression of genes of the present invention. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the recombinant DNA constructs.

A number of classes of ribozymes have been identified. One class of ribozymes is derived from a number of small circular RNAs, which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff et al. *Nature* 334:585-591 (1988), herein incorporated by reference in its entirety.

The present invention also provides antibodies that specifically bind to the polypeptides of the present invention and recombinant DNA constructs that comprise nucleic acid molecules of the present invention.

Plant Recombinant DNA Constructs and Transformed Plants

The term "transgenic plant" means a plant that contains an exogenous nucleic acid, which can be derived from the same plant species or from a different species. By "exogenous" it is meant that a nucleic acid molecule originates from outside the plant to which the nucleic acid molecule is introduced. An exogenous nucleic acid molecule can have a naturally occurring or non-naturally occurring nucleotide sequence. One skilled in the art understands that an exogenous nucleic acid molecule can be a heterologous nucleic acid molecule derived from a different plant species than the plant into which the nucleic acid molecule is introduced or can be a nucleic acid molecule derived from the same plant species as the plant into which it is introduced.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

Exogenous nucleic acid molecules may be transferred into a plant cell by the use of a recombinant DNA construct (or vector) designed for such a purpose. The present invention also provides a plant recombinant DNA construct (or vector) for producing transgenic plants, wherein the plant recombinant DNA construct (or vector) comprises a sense oligonucleotide or polynucleotide or an antisense oligonucleotide or polynucleotide. Methods that are well known to those skilled in the art may be used to prepare the plant recombinant DNA construct (or vector) of the present invention. These methods include in vitro recombinant DNA techniques, synthetic techniques, and in vivo genetic recombination. Such techniques are described in Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1989).

A plant recombinant DNA construct (or vector) of the present invention contains a sense oligonucleotide or polynucleotide or an antisense oligonucleotide or polynucleotide and operably linked regulatory sequences or control elements. Exemplary regulatory sequences include but are not limited to promoters, translation leader sequences, introns, 3' non-translated sequences. The promoters can be constitutive, inducible, or preferably tissue-specific promoters.

A plant recombinant DNA construct (vector) of the present invention will typically comprise a selectable marker that confers a selectable phenotype on plant cells. Selectable markers may also be used to select for plants or plant cells that contain the exogenous nucleic acid molecules of the present invention. The marker may encode biocide resistance, antibiotic resistance (e.g., kanamycin, G418 bleomycin, hygromycin, etc.), or herbicide resistance (e.g., glyphosate, etc.).

Examples of selectable markers include, but are not limited to, a neo gene (Potrykus et al., *Mol. Gen. Genet.* 199:183-188 (1985)) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988)) which encodes glyphosate resistance; a nitrilase gene which confers resistance to bromoxynil (Stalker et al., *J. Biol. Chem.* 263: 6310-6314 (1988)); a mutant acetolactate synthase gene (ALS) which confers imidazolinone or sulphonylurea resistance (European Patent Application 154,204 (Sep. 11, 1985)); and a methotrexate resistant DHFR gene (Thillet et al., *J. Biol. Chem.* 263:12500-12508 (1988)).

A plant recombinant DNA construct (vector) of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., *Proc. Natl. Acad. Sci.* (U.S.A) 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)) a xylE gene (Zukowsky et al., *Proc. Natl. Acad. Sci.* (U.S.A.) 80:1101-1105 (1983)) which encodes a catechol dioxygenase that can convert chromogenic catechols; an α-amylase gene (Ikatu et al., *Bio/Technol.* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988), which is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (Biochem. Soc. Trans. 15, 17-19 (1987)) to identify transformed cells.

In preparing the recombinant DNA constructs (vectors) of the present invention, the various components of the construct or fragments thereof will normally be inserted into a convenient cloning vector, e.g., a plasmid that is capable of replication in a bacterial host, e.g., *E. coli*. Numerous cloning vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A plant recombinant DNA construct (vector) of the present invention may also include a chloroplast transit peptide, in order to target the polypeptide of the present invention to the plastid. The term "plastid" means the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region. Many plastid-localized polypeptides are expressed from nuclear genes as precursors and are targeted to the plastid by a chloroplast transit peptide (CTP), which is removed during the import steps. Examples of such chloroplast polypeptides include the small subunit of ribulose-1,5-biphosphate carboxylase (ss-RUBISCO, SSU), 5-enolpyruvateshikimate-3-phosphate synthase (EPSPS), ferredoxin, ferredoxin oxidoreductase, the light-harvesting-complex protein I and protein II, and thioredoxin F. It has been demonstrated that non-plastid polypeptides may be targeted to the chloroplast by use of polypeptide fusions with a CTP and that a CTP sequence is sufficient to target a polypeptide to the plastid. Those skilled in the art will also recognize that various other recombinant DNA constructs can be made that utilize the functionality of a particular plastid transit peptide to import the enzyme into the plant cell plastid depending on the promoter tissue specificity.

The present invention also provides a transgenic plant comprising in its genome an exogenous nucleic acid molecule which comprises: (A) a 5' non-coding sequence which functions in the cell to cause the production of an RNA molecule; which is operably linked to (B) an antisense oligonucleotide or polynucleotide or a sense oligonucleotide or polynucleotide of this invention; which is operably linked to (C) a 3' non-translated sequence that functions in said cell to cause termination of transcription.

Transgenic plants of the present invention preferably have incorporated into their genome or transformed into their chloroplast or plastid genomes an exogenous nucleic acid molecule (or "transgene") that comprises a sense oligonucleotide or polynucleotide or an antisense oligonucleotide or polynucleotide. Transgenic plants are also meant to comprise progeny (descendant, offspring, etc.) of an), generation of such a transgenic plant A seed of any generation of all such transgenic plants wherein said seed comprises a sense oligo-nucleotide or polynucleotide or an antisense oligonucleotide or polynucleotide of the present invention is also an important aspect of the invention.

The DNA constructs of the present invention may be introduced into the genome of a desired plant host by a variety of conventional transformation techniques, which are well known to those skilled in the art. Preferred methods of transformation of plant cells or tissues are the *Agrobacterium* mediated transformation method and the biolistics or particle-gun mediated transformation method. Suitable plant transformation vectors for the purpose of *Agrobacterium* mediated transformation include those derived from a Ti plasmid of *Agrobacterium tumefaciens*, as well as those disclosed, e.g., by Herrera-Estrella et al., Nature 303:209 (1983); Bevan, Nucleic Acids Res. 12: 8711-8721 (1984); Klee et al., Bio-Technology 3(7): 637-642 (1985); and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of an antisense oligonucleotide or polynucleotide or a sense oligonucleotide or polynucleotide in monocots using electroporation or particle-gun mediated transformation is composed of the following: a promoter that is inducible or constitutive or tissue-specific; an intron that provides a splice site to facilitate expression of the gene, such as the Hsp70 intron (U.S. Pat. No. 5,859,347); and a 3' polyadenylation sequence such as the nopaline synthase 3' sequence (NOS 3'; Fraley et al., Proc. Natl. Acad. Sci. USA 80: 4803-4807 (1983)). This expression cassette may be assembled on high copy replicons suitable for the production of large quantities of DNA.

An example of a useful Ti plasmid cassette vector for plant transformation is described in U.S. Pat. No. 6,147,278 herein incorporated by reference in its entirety, and contains a gene encoding an EPSPS enzyme conferring glyphosate resistance (denominated aroA; CP4), which is an excellent selection marker gene for many plants. The gene is fused to the *Arabidopsis* EPSPS chloroplast transit peptide (CTP2) and expressed from the FMV promoter as described therein.

When adequate numbers of cells (or protoplasts) containing an antisense oligonucleotide or polynucleotide or a sense oligonucleotide or polynucleotide of the present invention are obtained, the cells (or protoplasts) can be cultured to regenerate into whole plants. Such regeneration techniques rely on manipulation of certain phytohormones in a tissue culture growth medium, typically relying on a biocide and/or herbicide marker which has been introduced together with the desired nucleotide sequences. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canolairapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al., Handbook of Plant Cell Culture—Crop Species. Macmillan Publ. Co. (1984); Shimanioto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674

(1992); Hayashimoto, Plant Physiol. 93:857-863 (1990); and Datta et al., Bio-technology 8:736-740 (1990). Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., Ann. Rev. Plant Phys. 38:467-486 (1987).

A transgenic plant formed using *Agrobacterium* transformation methods typically contains a single exogenous gene on one chromosome. Such transgenic plants can be referred to as being heterozygous for the added exogenous gene. More preferred is a transgenic plant that is homozygous for the added exogenous gene; i.e., a transgenic plant that contains two added exogenous genes, one gene at the same locus on each chromosome of a chromosome pair. A homozygous transgenic plant can be obtained by sexually mating (selfing) an independent segregant transgenic plant that contains a single exogenous gene, germinating some of the seed produced and analyzing the resulting plants produced for the exogenous gene of interest.

The development or regeneration of transgenic plants containing the exogenous nucleic acid molecule that encodes a polypeptide of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants. A transgenic plant of the present invention containing desired polypeptides of the present invention are cultivated using methods well known to one skilled in the art.

Plants that can be made to have larger organ size by practice of the present invention include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, southern pine, soybean, spinach, squash, strawberry, sugarbeet, sugarcane, sunflower, sweet potato, sweetgum, tangerine, tea, tobacco, tomato, turf, a vine, watermelon, wheat, yarns, and zucchini.

The present invention also provides cells of the transgenic plants of the present invention which could be used for regenerating a plant or any organ of plant with present invention.

The present invention also further provides a method for altering a specific organ or organs in a plant to generate smaller plant or plant organ, the method comprising the steps of: a) introducing into the genome of the plant an exogenous nucleic acid molecule comprising in the 5' to 3' direction i) a promoter that functions in the cells of said plant, said promoter operably linked to; ii) an antisense oligonucleotide or polynucleotide or a sense oligonucleotide or polynucleotide of the present invention, said antisense oligonucleotide or polynucleotide operably linked to; iii) a 3' non-translated nucleotide sequence that functions in said cells of said plant to cause transcriptional termination; b) obtaining transformed plant cells containing the exogenous nucleic acid molecule of step (a); and c) regenerating from said transformed plant cells a transformed plant in which the expression of an endogenous gene of the present invention is suppressed or inhibited.

The following examples are provided to better elucidate the practice of the present invention and should not be interpreted in any was to limit the scope of the present invention. Those skilled in the art will recognize that various modifications, truncations, etc., can be made to the methods and genes described herein while not departing from the spirit and scope of the present invention. In the following examples references are made to proprietary databases and proprietary libraries, e.g., of DNA clones, available to the inventors from Monsanto Company.

EXAMPLES

Example 1

Stock Plant Material and Growth Conditions

*Arabidopsis thaliana* var Columbia seeds were obtained from Lehle seeds (LEHLE SEEDS 1102 South Industrial Blvd., Suite D, Round Rock Tex. 78681 USA). For growing seeds into plants, 2.5 inch pots are prepared with soil covered with bridal veil or a mesh screen, making sure that the soil is not packed too tightly and the mesh is in contact with the soil surface (this ensures that the germinating seedlings will be able to get through the mesh. Seeds are sown and covered with a germination dome. Seeds are vernalized for 3-4 days. Plants are grown under conditions of 16 hours light/8 hours dark at 20-22° C., 70% humidity. They are watered twice weekly, and fertilize from below with ½×(half of the strength recommended by the manufacturer) Peters 20-20-20 fertilizer (from Hummert International, Earth City, Mo.). Micronutrients are added (Hummert's Dyna-grain Soluble Trace Elements) (in full strength recommended by the manufacturer) every other week. After about 1-2 weeks, dome is removed and pots are thinned to one or two plants per pot. Clip the primary bolt, when it develops, to encourage more secondary bolt formation. In 5-7 days the plants will be ready for infiltration.

Isolation of Gene and its modification: Senescing leaves were removed from plants grown as indicated in above Example 1. Senescing leaves were flash frozen in liquid nitrogen until ready for isolation of RNA. RNA was prepared from senescent *Arabidopsis* leaves by the Trizol method (Gibco BRL, Life Technologies, Gaithersburg, Md. U.S.A.) essentially as recommended by the manufacturer. SAG13 cDNA was isolated by reverse transcription from the above senescent leaf RNA using Superscript II kit (Gibco BRL, Life Technologies, Gaithersburg, Md. U.S.A.) according to the manufacturer's directions. To isolate DNA molecules of the present invention, two gene specific primers, MF16 5'SAG13 and MF17 3'SAG13, were designed based on the SAG13 sequence information (AF192276) from Genbank and custom synthesized by Gibco BRL, Life Technologies, Gaithersburg, Md. U.S.A. The sequence of MF16 5'SAG13 is ATA TTT AAC AAG CCA TGG CAA AGG A, and M17 3'SAG13 is ATA TGT GTT TGA ATT CAT AGT CTT GAA identified as SEQ ID NO: 55 and SEQ ID NO: 56 respectively in the sequence list, which annealed on SAG13 gene to introduce Nco 1 site at 5' end and Eco R1 site at 3' end of the gene. PCR was then performed to amplify the SAG-13 cDNA using the above prepared cDNA as the template, and MF16 5'SAG13 and MF17 3'SAG13 as the primers. The thermal cycling conditions were as follows: 94° C., 40 second, followed 30 cycles of 94° C., 25 seconds; 55° C., 30 seconds and 68° C., 2 minutes 30 seconds (All reagents and equipment for PCR can be procured from Applied Biosystems, 850 Lincoln Center Drive, Foster City, Calif. 94404, USA). The amplified cDNA was purified by gel-electrophoresis to obtain the gene identified as SEQ ID NO: 1.

All other sequences shown in table from Example 8 are isolated from different plant species by designing appropriate PCR primers based on the sequence information provided in table of Example 8. For isolating these sequences, total RNA is isolated from appropriate crop and other desired plant species by pooling tissues of different developmental stages of all vegetative and reproductive organs. Sequences can be cloned out from total RNA by methodology shown in above paragraph. In order to isolate genes of the invention from microorganisms DNA is isolated from the desired microorganism. Isolation of DNA from microorganism is well known in the art (Sambrook, et al., In: *Molecular Cloning, A Laboratory Manual*, 2nd Edition, Cold Spring Harbor Press, Cold Spring Harbor, N.Y. 1989, herein incorporated by reference in its entirety). This DNA along with oligonucleotide PCR primers can be used in a polymerase chain reaction by any one skilled in the art to isolate genes of the invention.

When the amplified product SEQ ID NO: 1 was sequenced, it was discovered to have an extra "T" between position 622-628, as compared to SEQ ID NO: 3. Addition of an extra "T" in the amplified product caused the generation of termination codon at position 211 of SEQ ID NO: 4 and a change of amino acid at position 210 from aspartic acid (D) to arginine (R). It is known in the art that polymerase chain reaction can cause point mutations (Cline J, Braman J C, Hogrefe H H; *Nucleic Acids Res.*; 24(18):3546-51, 1996) as shown between SEQ ID No: 1 and SEQ ID NO: 3. However such a mutation can be created within an isolated nucleic acid molecule at a desired position by a number of methods know in the art (Shortle D. et al., Annu. Rev. Genet. 15: 265, 1981; Itakura K. et al., Ann Rev. Biochem 53: 323, 1984; Botstein D. & Shortle D., Science 229: 1193, 1985; Smith M., Ann. Rev. Genet. 19: 423 1985; and Sambrook, et al., In: *Molecular Cloning, A Laboratory Manual*, 2nd Edition, Cold Spring Harbor Press, Cold Spring Harbor, N.Y. 1989, herein incorporated by reference in its entirety). These mutations can also be introduced by causing a point mutation or site directed mutagenesis in nucleotide SEQ ID NO: 3 by using commercially available kits such as QuickChange™ Site Directed Mutagenesis Kit from Stratagene (11011 North Torrey Pines Road, La Jolla, Calif. 92037) to result in a peptide with about 90% of the N-terminal of SEQ ID NO: 4 by altering a nucleotide sequence to encode a stop codon at amino acid position 241±3, or to result in a peptide with about 80% of the N-terminal of SEQ ID NO: 4 by altering a nucleotide sequence to encode a stop codon at amino acid position 214±3, or to result in about 70% of the N-terminal of SEQ ID NO: 4 by altering a nucleotide sequence to encode a stop codon at amino acid position 188±3, or to result in about 60% of the N-terminal of SEQ ID NO: 4 by altering a nucleotide sequence to encode a stop codon at amino acid position 161±3, or to result in about 50% of the N-terminal of SEQ ID NO: 4 by altering a nucleotide sequence to encode a stop codon at amino acid position 134±3 of the reading frame. These mutations can also be introduced in site by causing point mutation or site directed mutagenesis in nucleotide SEQ ID NO: 3 by using in situ mutagenesis technology provided by Valigen Inc. (Newtown Pa. USA) (U.S. Pat. No. 6,211,351; U.S. Pat. No. 6,271,360, WO 01/24615 A1, and WO 01/25460 A2, herein incorporated by reference in its entirety) to result in a peptide with about 90% of the N-terminal of SEQ ID NO: 4 by altering a nucleotide sequence to encode a stop codon at amino acid position 241±3, or to result in a peptide with about 80% of the N-terminal of SEQ ID NO: 4 by altering a nucleotide sequence to encode a stop codon at amino acid position 214±3, or to result in about 70% of the N-terminal of SEQ ID NO: 4 by altering a nucleotide sequence to encode a stop codon at amino acid position 188±3, or to result in about 60% of the N-terminal of SEQ ID NO: 4 by altering a nucleotide sequence to encode a stop codon at amino acid position 161±3, or to result in about 50% of the N-terminal of SEQ ID NO: 4 by altering a nucleotide sequence to encode a stop codon at amino acid position 134±3 of the reading frame. Additional mutations can be introduced to provide a translational product that is larger or smaller than SEQ ID NO: 1. It can be determined that these modified polynucleotide sequences will provide a desired phenotype without undue experimentation Example 2

Figure 4:
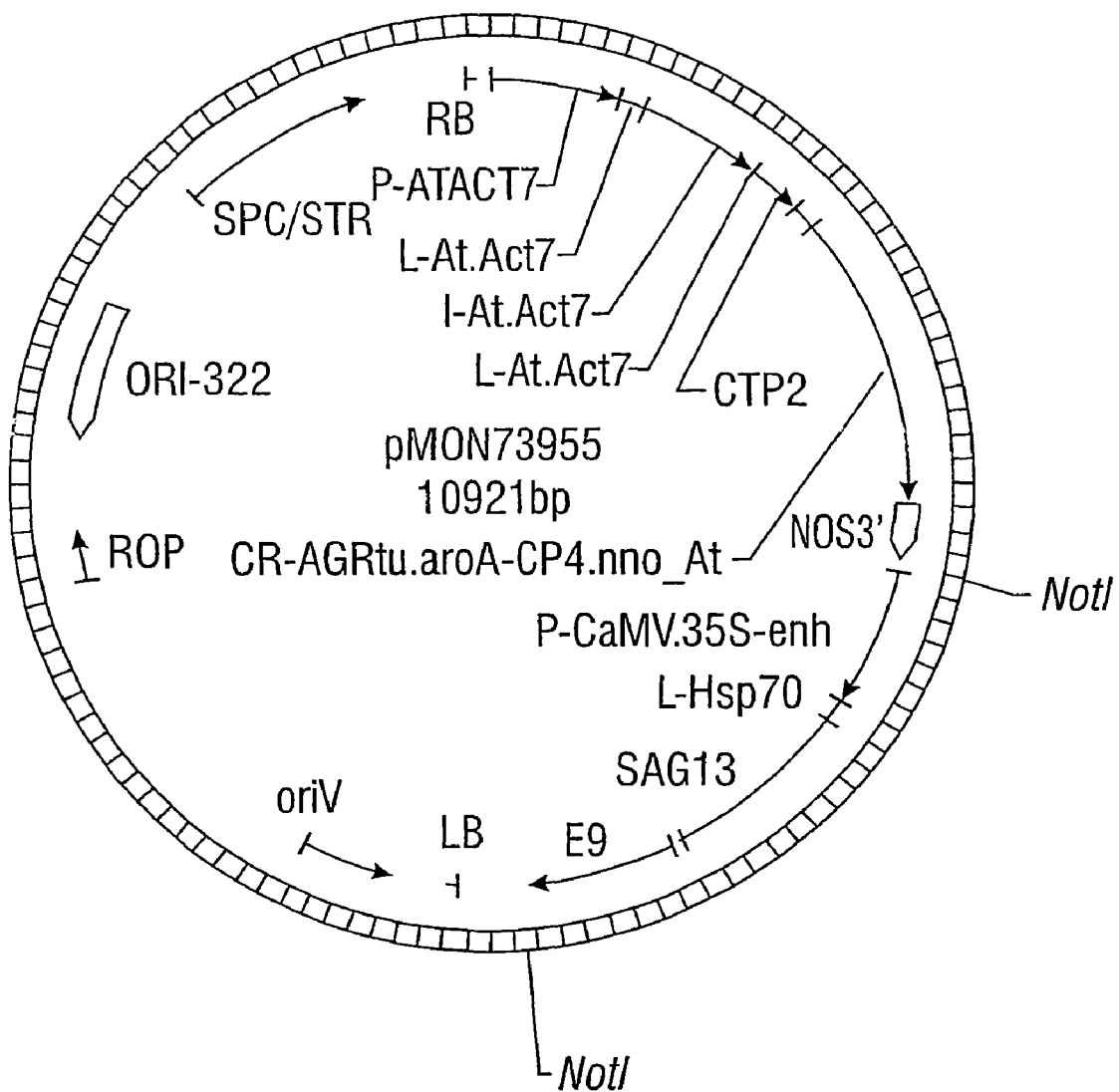
FIG. 4 shows a plasmid map for plant transformation vector pMON 73955 with its elements.

Genetic Elements of Cloning Vector for Expressing Protein in Plants (FIGS. 1 and 4)

The DNA constructs used are double border plant transformation constructs that contain DNA segments that provide replication function and antibiotic selection in bacterial cells, for example, an *E. coli* origin of replication such as ori322, a broad host range origin of replication such as oriV or oriRi, and a coding region for a selectable marker such as Spc/Str that encodes for Tn7 aminoglycoside adenyltransferase (aadA) conferring resistance to spectinomycin or streptomycin, or a gentamicin (Gm, Gent) selectable marker. For plant transformation, the host bacterial strain is *Agrobacterium tumefaciens* ABI or LBA4404.

The genetic elements of the DNA constructs are assembled to have in operable linkage a promoter that functions in plants. Additionally an antibiotic or herbicide marker cassette, an epitope tag (For example Flag® peptide catalog number F-3290, SIGMA, P.O. Box 14508 St. Louis, Mo. 63178 USA) at the 3' termination region of gene of interest is included in the DNA construct. The multiple cloning site in this DNA construct encodes BgIII, NcoI, EcoRI, SalI, and XhoI. The epitope tag region was encoded with SalI and XhoI restriction sites for optional removal of the epitope tag. The NcoI site encodes a Kozak sequence for efficient translation of the protein products. DNA constructs used in the method of the current invention comprise any promoter known to function to cause the transcription in plant cells and any antibiotic tolerance encoding polynucleotide sequence known to confer antibiotic tolerance to plant cells. The antibiotic tolerance polynucleotide sequences include, but are not limited to polynucleotide sequences encoding for proteins involved in antibiotic tolerance to kanamycin, neomycin, hygromycin, and other antibiotics known in the art. Antibiotic tolerance gene in such a vector can be replaced by herbicide tolerance encoding for 5-enolpyruvylshikimate-3-phosphate synthase (EPSPS, described in U.S. Pat. Nos. 5,627,061, and 5,633,435, herein incorporated by reference in its entirety; Padgette et al. (1996) *Herbicide Resistant Crops*, Lewis Publishers, 53-85, and in Penaloza-Vazquez, et al. (1995) *Plant Cell Reports* 14:482-487) and aroA (U.S. Pat. No. 5,094,945) for glyphosate tolerance, bromoxynil nitrilase (Bxn) for Bromoxyril tolerance (U.S. Pat. No. 4,810,648), phytoene desaturase (crtI (Misawa et al, (1993) *Plant Journal* 4:833-840, and (1994) *Plant Jour* 6:481-489) for tolerance to norflurazon, acetohydroxy acid synthase (AHAS, Sathasiivan et al. (1990) *Nucl. Acids Res.* 18:2188-2193) and the bar gene for tolerance to glufosinate (DeBlock, et al. (1987) *EMBO J.* 6:2513-2519. Herbicides for which transgenic plant tolerance has been demonstrated and the method of the present invention can be applied include, but are not limited to: glyphosate, glufosinate, sulfonylureas, imidazolinones, bromoxynil, delapon, cyclohezanedione, protoporphyrionogen oxidase inhibitors, and isoxaslutole herbicides.

Genetic elements of transgene DNA constructs used for plant transformation and expression of transgenes in plants include, but are not limited to: the P-E35S promoter (U.S. Pat. Nos. 5,539,142, 5,196,525, 5,322,938 and 5,164,316 herein incorporated by reference in its entirety). P-E35S promoter can be replaced by P-CaMV.35S promoter (U.S. Pat. No. 5,858,742, herein incorporated by reference in its entirety), or by enhanced P-CaMV.35S from Cauliflower mosaic virus containing a duplication of the −90-300 region as described in U.S. Pat. No. 5,424,200, herein incorporated by reference in its entirety; or the Figwort mosaic virus promoter, P-FMV, as described in U.S. Pat. No. 5,378,619, herein incorporated by reference in its entirety; or the P-AtEF1a (P-AtEF1 or EF1a) a promoter region from the *Arabidopsis thaliana* elongation factor gene 1a; the Gbox10 and Gbox11motif (Fumiharu et al., (1999) *Plant J.* 18:443-448); or the DC3 promoter region from carrot (Seffens et al., Develop. Genet. 11:65-76); or the TP12 promoter (GenBank accession no. U68483); DNA molecules encoding plastid transit peptides, for example, the *Arabidopsis* EPSPS chloroplast transit peptide, At.CTP2 as described in U.S. Pat. No. 5,633,435, herein incorporated by reference in its entirety. The method of the present invention enables one of skill in the art of plant molecular biology to design and assemble plant expression cassettes that contain promoters of known and unknown function. The genetic elements of the DNA construct further comprise 5' leader polynucleotides for example, the Hsp70 non-translated leader sequence from *Petunia hybrida* as described in U.S. Pat. No. 5,362,865, herein incorporated by reference in its entirety. The genetic elements further comprise herbicide tolerance genes that include, but are not limited to, for example, the aroA:CP4 coding region for EPSPS glyphosate resistant enzyme isolated from *Agrobacterium tumefaciens* (AGRTU) strain CP4 as described in U.S. Pat. No. 5,633,435, herein incorporated by reference in its entirety. The genetic elements of the DNA construct further comprise 3' termination regions that include, but are not limited to, the E9 3' termination region of the pea RbcS gene that functions as a polyadenylation signal; the nos is the 3' end of the nopaline synthase gene that functions as a polyadenylation signal. The genetic elements of the DNA construct further comprise the right border (RB) and left borders (LB) of the Ti plasmid of *Agrobacterium tumefaciens* octopine and nopaline strains.

Example 3

Cloning of isolated DNA Molecule: Amplified and purified product SEQ ID NO: 1 from Example 1 was digested by Nco1 and EcoR1 restriction enzymes (BRL/Life Technologies, Inc., Gaithersburg, Md.). The digested product was purified again by gel electrophoresis before ligating to binary vector pMON23435 that had been linearized by Nco 1 and Eco R1 and T4 DNA ligase (BRL/Life Technologies, Inc., Gaithersburg, Md.). The ligation reaction was performed according to the manufacturer's instructions. The resulting plasmid was confirmed by restriction mapping and sequencing. After ligation of the Nco-EcoR1 fragment of SEQ ID NO: 1 into vector pMON23435, the new construct was referred to as construct pMON57521. Construct pMON57521 was transformed in *Arabidopsis* plants by *Agrobacterium* mediated transformation procedure.

Amplified and purified product SEQ ID NO: 1 can also be cloned in antisense orientation in appropriate cloning sites of vector pMON23435 to express the opposite strand of SEQ ID NO:1 by one skilled in the art.

Example 4

Cloning of DNA molecules of the present invention: This example illustrates how all other DNA molecules as shown in table from example 9 are isolated from different plant species by designing appropriate PCR primers based on the DNA sequence information provided in the table of Example 8. For isolating these DNA molecules one skilled in the art will isolate total RNA from a crop or other desired plant species by pooling tissues of different developmental stages of all vegetative and reproductive organs. DNA molecules are cloned out from total RNA by methodology shown in Example 2. In order to isolate genes of the invention from microorganisms one will have to isolate DNA from desired microorganism. Isolation of DNA from microorganism is well known in the art (Sambrook, et al., In: *Molecular Cloning, A Laboratory Manual,* 2nd Edition, Cold Spring Harbor Press, Cold Spring Harbor, N.Y. 1989, herein incorporated by reference in its entirety). This DNA along with oligonucleotide PCR primers can be used in a polymerase chain reaction by any one skilled in the art to isolate genes of the invention.

Design of primers and reaction conditions are determined as described in the art. (PCR Strategies, Edited by Michael A. Innis; David H. Gelfand; John J. Sninsky; Academic Press 1995 and PCR Protocols, A Guide to Method and Applications, Edited by Michael A. Innis; David H. Gelfand; John Sninsky; and Thomas J. White, Academic Press 1990, herein incorporated by reference in its entirety). All reagents for isolating sequences of the invention can be procured from Gibco BRL, Life Technologies, Gaithersburg, Md. U.S.A. Isolated DNA molecule sequences can be cloned at appropriate cloning sites in sense or antisense orientation of a plant expression vector shown in Example 3 or a similar vector capable of ectopically expressing the gene of interest of the present invention in sense or antisense orientation as known in the art.

Example 5

This example illustrates how *Agrobacterium* cells are transformed and how transformed cells are cultured.
Transformation:
1. Electroporate 2 μl of DNA construct into 20 μl of ABI competent cells;
2. Pipette transformed cells directly onto LB plates containing Spectinomycin (75 μg/ml), Kanamycin (50 μg/ml), Chloramphenicol (25 μg/ml). Add 50 μl of SOC media to plate and spread;
3. Incubate plated transformation at 28° C. for 2 days (or can grow over weekend).
ABI Cell Culture:
1. Pick 3 colonies per ABI plate and grow each in 4 ml LB media containing Spectinomycin (75 μg/ml), Kanamycin (50 μg/ml), Chloramphenicol (25 μg/ml);
2. Incubate 4 ml cultures of at 28° C., shaking, for 2 days. (Culture tubes should be at an angle).
Glycerol Stocks, & DNA Preps:
1. Make three 1 ml ABI glycerol stocks per 4 ml culture, using 500 μl of culture and 500 μl of 40% glycerol. Freeze and store at −80° C.
2. Miniprep remaining culture (about 2.5 ml), using a Qiagen miniprep kit and protocol (Qiagen Genomics, Inc., Seattle, Wash.), ensuring add PB buffer wash step and EB buffer (10 mM Tris-Cl, pH 8.5) to 70° C. before eluting DNA from column. The resulting volume per miniprep sample should be 50 µl.

Digest Confirmation:
1. Using the Pollux and construct maps, choose two digests to perform: one to verify insert integrity, one to verify vector integrity (will need to refer to plasmid maps);
2. Digest 17 µl miniprep DNA per digest, resulting in a final digest volume of 20 µl;
3. Run 20 µl of each digest on 1% agarose gel vs. 1 Kb DNA ladder; and
4. For 2 of 3 confirmed clones, streak LB plates containing Spectinomycin (75 µg/ml), Kanamycin (50 µg/ml), Chloramphenicol (25 µg/ml) from ABI glycerol stocks and allow to grow at 28° C. for 2 days (or can grow over weekend).

All other reagents used in example 4 can be procured from Sigma Chemical Company. Saint Louis, Mo., USA

Example 6

This example demonstrates how to transform *Arabidopsis* plants with gene constructs of present invention *Arabidopsis* plants may be transformed by any one of many available methods. For example, *Arabidopsis* plants may be transformed using in planta transformation method by vacuum infiltration (see, Bechtold et al., In planta *Agrobacterium* mediated gene transfer by infiltration of adult *Arabidopsis thaliaia* plants. CR Acad. Sci. Paris Sciences de la vie/life sciences 316: 1194-1199 (1993), herein incorporated by reference in its entirety). Plants can be grown as described in Example 1.

*Agrobacterium* Preparation (Small Scale and Large Scale Cultures):

*Agrobacterium* strain ABI is streaked onto an LB plate containing Spectinomycin 100 mg/L, Streptomycin 100 mg/L, Chloramphenicol 25 mg/L, and Kanamycin 50 mg/L (denoted SSCK). Two days prior to infiltration, a loop of *Agrobacterium* is placed into a tube containing 10 mls LB/SSCK and put on a shaker in the dark at 28° C. to grow overnight. The following day, the *Agrobacterium* is diluted 1:50 in 400 mls of bacterial grown medium such as SSCK and put on a shaker at 28° C. to grow for 16-20 hours.

Infiltration

Harvest the *Agrobacterium* cells by pouring into a 500 ml centrifuge bottle and spinning at 3500 rpm for 20-25 minutes. Pour off the supernatant. Dry the pellet and then resuspend in 25 ml Infiltration Medium (MS Basal Salts 0.5%, Gamborg's B-5 Vitamins 1%, Sucrose 5%, MES 0.5 g/L, pH 5.7) with 0.44 nM benzylaminopurine (BAP) (10 µl of a 1.0 mg/L stock in DMSO per liter) and 0.02% Vac-In-Stuff (Silwet L-77) from Lehle Seeds (Round Rock, TX). The BAP and Silwet L-77 are added fresh the day of infiltration. Add 200 µl of Silwet L-77, and 20 µl of BAP (0.5 mg/L stock). Using Infiltration Medium as your blank, take the $OD_{600}$ of a 1:10 dilution of the *Agrobacterium* suspensions. Calculate the volume needed for 400 ml of *Agrobacterium* suspension/infiltration medium, OD600=0.6, for the vacuum infiltration.

$$\frac{(\text{final volume}) * (\text{final } OD600)}{OD600} = \text{Equation}$$

Volume needed for final $OD600$ of 0.6

Place resuspended culture in a Rubbermaid container inside a vacuum dessicator. Invert pots containing plants to be infiltrated into the solution so that the entire plant is covered, including the rosette, but not too much of the soil is submerged. Soak the plants with water for at least 30 min. prior to infiltration. (This keeps the soil from soaking up the *Agrobacterium* suspension).

Draw a vacuum of ~23-27 in. Hg for 10 min. Quickly release the vacuum. Briefly drain the pots, place them on their sides in a diaper-lined tray, cover the tray with a dome to maintain humidity, and return to growth chamber. The following day, uncover the pots, set them upright, and remove the diaper. Do not water plants for ~5 days. After the 5 days are up, allow the plants to be watered and to continue to grow under the same conditions as before. (The leaves that were infiltrated may degenerate but the plant should survive until it is finished flowering).

Harvesting and Sterilizing Seed

Cone the plants, individually, by using the Lehle Aracons (Lehle Seeds, Round Rock, Tex.) approximately 2 weeks after infiltration. After all of the seed is matured and has set (~4 weeks post-infiltration), remove the plants from water to dry down the seeds. Approximately 2 weeks later harvest the seeds by cutting the branches below the cone. Clean the seed by using a sieve to catch the silique and branch material and allow the seed to go through. Place the seed in an envelope or in 15 ml conical tubes.

Transfer desired amount of seeds to 15 ml conical tubes prior to sterilization. Loosen the lid to the conicals and place them on their side in a vacuum dessicator with a beaker containing 400 ml of bleach Clorox (Clorox Company, Oakland, Calif.) and 4 ml of Hydrochloric Acid. (Add the HCl to the Clorox in a fume hood). Pull a vacuum just to seal the dessicator, and close the suction (i.e. so that the dessicator is still under a vacuum but the vacuum is not still being directly pulled) for ~16 hrs. After sterilization, release the vacuum and place tubes containing seed in a sterile hood (keep caps loose so gas can still be released).

Plate ("sprinkle") the seed on selection plates containing MS Basal Salts 4.3 g/L, Gamborg'a B-5 (500×) 2.0 g/L, Sucrose 10 g/L, MES 0.5 g/L, and 8 g/L Phytagar (Life Technologies, Inc., Rockville, Md.) with Carbenicillin 250 mg/L, Cefotaxime 100 mg/L. Selection levels will either be kanamycin 60 mg/L, Glyphosate 60 µM, or Bialaphos 10 mg/L.

A very small amount of seed can be first plated out to check for contamination. If there is contamination, re-sterilized seeds for ~4 more hours and check for contamination again. The second sterilization is usually not necessary, but sometimes the seed harbors a fungal contaminant and repeat sterilizations are needed. (The sterilization duration generally is shorter than 16 hours because of significantly decreased germination rates starting at 24 hr. sterilization duration). Seal plates with parafilm and place in a cold room to vernalize for ~2-4 days. After seeds are vernalized, place in percival with cool white bulbs.

Transfer to Soil

After 5-10 days at ~26° C. and a 16/8 light-dark cycle, the transformants will be visible as green plants. After another 1-2 weeks, plants will have at least one set of true leaves. Transfer plants to soil, cover with a germination dome, and move to a growth chamber with normal *Arabidopsis* growth conditions. Keep covered until new growth is apparent (usually 5-7 days).

Example 7

Following subsections of Example 7 are used for describing phenotypic changes after transformation and growth of

Figure 2:
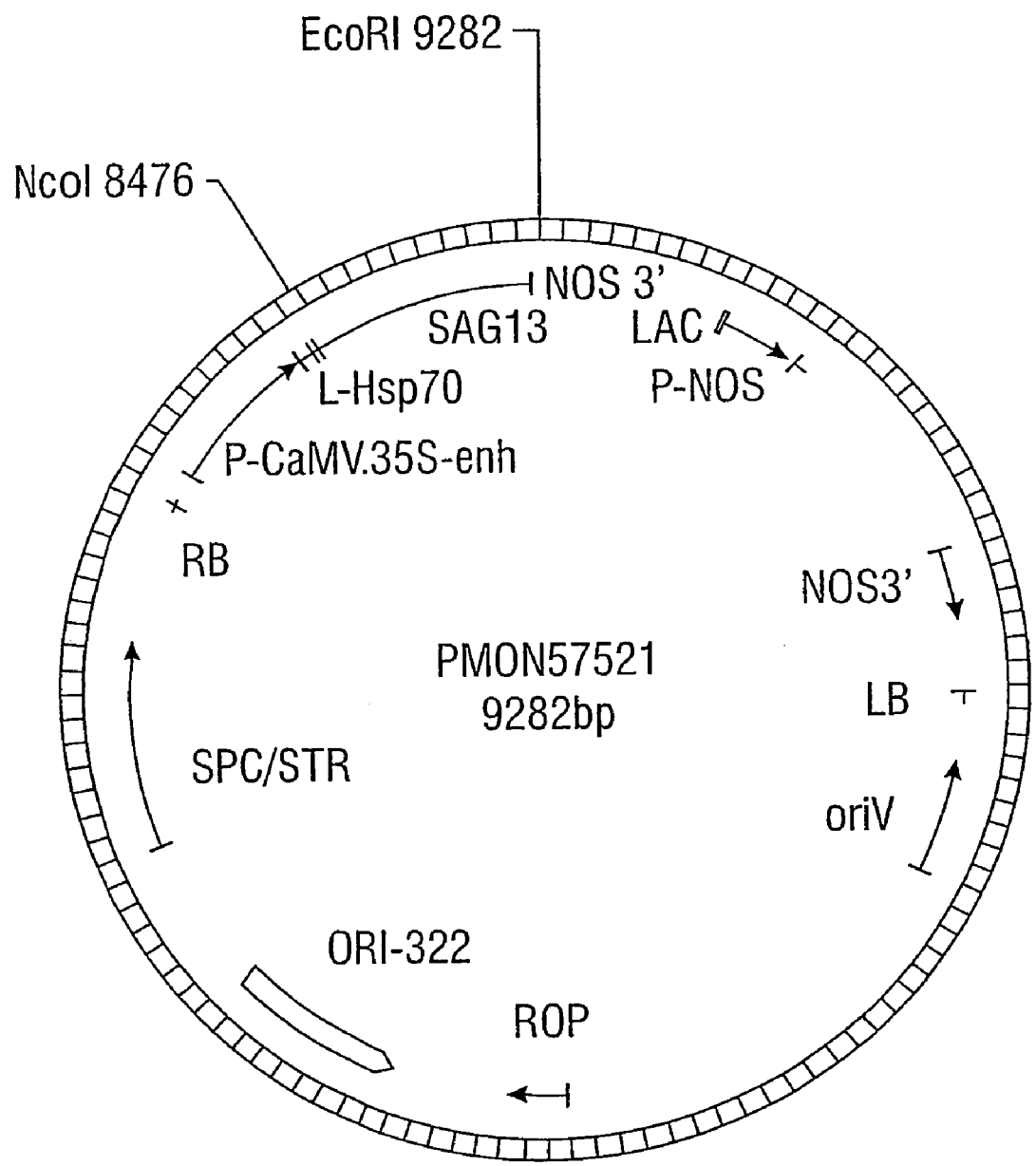
FIG. 2 shows a plasmid map for plant transformation vector pMON 57521 with its elements.

*Arabidopsis* plants as described in Example 6. Three different events obtained from transformation of pMON57521 (FIG. 2) into *Arabidopsis thaliana* ecotype Columbia were selected and grown side by side with wild type plants. Growth conditions were 16 hr light, 8 hr night, 21 degrees Centigrade and 70% relative humidity. Plants were observed at all growth stages and photographed using an Olympus camera C-2500 L (Olympus America Inc., 2 Corporate Center Drive, Melville, N.Y. 11747) as described by the manufacturer. Microscopic images of plant organ were acquired after proper dissection on a stereoscopic microscope Nikon SMZ 1500 (NIKON, 1300 Walt Whitman Road, Melville, N.Y. 11747) equipped with MagnaFire Digital imaging system. Image quantitation was done as per manufacturer's instructions by using MagnaFire Digital imaging system's software s Pro™ or Lucis™ softwares (Optronics, 175 Cremona Drive, Goleta, Calif. 93117). The three events showed high phenotypic consistency in preliminary experiments and hence only two events were chosen for further downstream work.

Plants transformed with Construct pMON57521 were shown to exhibit 2 to 3 times larger flower and floral organs such as stamen and pistils when compared to the wild type, non transformed plants of the same species. Transgenic plants were also observed to have at least 2 times more lateral roots and 2 to 3 times thicker stem size when compared to the lateral roots and stems of wild type, non transformed plants of the same species. Approximately 2 fold increased trichome numbers and distribution were also observed. Over expression of the polypeptide encoded by the sequence in the pMON57521 construct of the present invention in the transformed plants, yielded plants that exhibited a 100% increase in individual seed size and weight. Approximately 20% increase in seed yield/plant was also observed for plants transformed with pMON57521 when compared to seed yield/plant of wild type, non transformed plants of the same species. The lines were followed up to 6 generations after transformation and appeared to be highly consistent in maintaining the observed phenotypic changes.

(A) Seed Size: Seeds from transformed plants exhibit increased seed size that was approximately twice as large as the seeds from wild type plants as shown in following table. Image sizes were determined by the Pro™ or Lucis™ software (Optronics, 175 Cremona Drive, Goleta, Calif. 93117) based on the image pixel value of wild type and transformed plants' seed under the same resolution. Plant lines 8752-1, 8752-2, 8752-6, and 8752-7 in Table 1 correspond to different transgenic plant lines produced by transforming wild *Arabidopsis* plants with pMON57521.

TABLE 1

| | Seed Size | | |
|---|---|---|---|
| | Seed size | Average | Std deviation |
| WT | 1820 | 1873 | 89 |
| | 1847 | | |
| | 1904 | | |
| | 1784 | | |
| | 2013 | | |
| 8752-1 | 3762 | 3627 | 191 |
| | 3441 | | |
| | 3812 | | |
| | 3400 | | |
| | 3720 | | |
| 8752-6 | 3700 | 3685 | 172 |
| | 3802 | | |
| | 3872 | | |
| | 3623 | | |
| | 3428 | | |

TABLE 1-continued

| | Seed Size | | |
|---|---|---|---|
| | Seed size | Average | Std deviation |
| 8748-2 | 3675 | 3664 | 96 |
| | 3784 | | |
| | 3724 | | |
| | 3543 | | |
| | 3597 | | |
| 8748-7 | 3712 | 3754 | 88 |
| | 3625 | | |
| | 3771 | | |
| | 3821 | | |
| | 3845 | | |

(B) Seed Weight: The seed from plants containing pMON57521 lines was also found to be heavier than WT seed. Seed weight was measured from 2 lines produced from event 8752 (8752-1 and 8752-6) and 2 lines from event 8748 (8748-2 and 8748-7) and compared with wild type. Shown below is a representative seed weight analysis. For each line, 3 replications were measured (i.e. 50 seeds were counted three times and measured each time). This analysis was repeated with different seed counts (eg. 100 seed or 150 seed) and was found to be highly reproducible. For example, weight per 100 seed is similarly high ~0.0025 gm. for wild type and 0.0046 gm. for seeds from plants transformed with sequence of the present invention. Data was also highly reproducible within a given line and across lines. The average weight of a single seed from a line transformed with sequence of the present invention was extrapolated to be ~0.048 mg as opposed to 0.026 mg for a WT seed. Plant lines 8752-1, 8752-6, 8748-2, and 8748-7 in Table 2 correspond to different transgenic plant lines produced by transforming wild *Arabidopsis* plants with pMON57521.

TABLE 2

| | Seed Weight | | |
|---|---|---|---|
| | Weight (gm./50 seed) | Average | Std deviation |
| WT | 0.0013 | 0.001333 | 5.7735E−05 |
| | 0.0014 | | |
| | 0.0013 | | |
| 8752-1 | 0.0024 | 0.0024 | 1E−04 |
| | 0.0025 | | |
| | 0.0023 | | |
| 8752-6 | 0.0024 | 0.002433 | 5.7735E−05 |
| | 0.0025 | | |
| | 0.0024 | | |
| 8748-2 | 0.0025 | 0.0024 | 1E−04 |
| | 0.0023 | | |
| | 0.0024 | | |
| 8748-7 | 0.0025 | 0.0024 | 1E−04 |
| | 0.0023 | | |
| | 0.0024 | | |

(C) Seed Number: Lines over expressing sequence of the present invention were found to have fewer seed per silique as compared to wild type plants. The average number of seed/silique of equivalent maturity was 34 for transgenic plants of the present invention as compared to 52 for wild type plants. The analysis was repeated three times with highly reproducible results within and between events.

TABLE 3

Seed Number

|  | Number/silique | Average | Std deviation |
|---|---|---|---|
| WT | 46 | 52 | 7.402702 |
|  | 62 |  |  |
|  | 50 |  |  |
|  | 57 |  |  |
|  | 55 |  |  |
|  | 42 |  |  |
| 8752-1 | 34 | 34 | 4.195235 |
|  | 32 |  |  |
|  | 30 |  |  |
|  | 30 |  |  |
|  | 38 |  |  |
|  | 40 |  |  |

(D) Seed Yield: There was an increase of >20% seed yield in transgenic plants of the present invention. Seed yield when measured in terms of weight of total seeds per plant.

TABLE 4

Seed Yield

|  | Yield (gm./plant) | Average | Std deviation |
|---|---|---|---|
| WT | 0.31 | 0.274 | 0.024129 |
|  | 0.25 |  |  |
|  | 0.28 |  |  |
|  | 0.27 |  |  |
|  | 0.25 |  |  |
|  | 0.30 |  |  |
|  | 0.26 |  |  |
|  | 0.28 |  |  |
|  | 0.3 |  |  |
|  | 0.24 |  |  |
|  | 0.25 |  |  |
|  | 0.29 |  |  |
| 8752-1 | 0.33 | 0.336667 | 0.021034 |
|  | 0.31 |  |  |
|  | 0.37 |  |  |
|  | 0.35 |  |  |
|  | 0.37 |  |  |
|  | 0.33 |  |  |
|  | 0.33 |  |  |
|  | 0.36 |  |  |
|  | 0.33 |  |  |
|  | 0.33 |  |  |
|  | 0.31 |  |  |
|  | 0.32 |  |  |

Example 8

This example describes changes in the branching pattern after transformation and growth of *Arabidopsis* plants as described in Example 6.

*Arabidopsis* plants over-expressing polypeptide molecules corresponding to SEQ ID NO: 2 appear to have more branches than wild type plants. This results in a net increase in silique number. Although each transgenic silique appears to have fewer seed than an equivalent wild type silique, the increase in branching appears to compensate resulting in a net increase in overall seed yield. The branching pattern of *Arabidopsis* over-expressing lines was compared to wild type plants and the transgenic plants were shown to have more branches than WT plants. All measurements were taken at growth stage 6.5 which corresponds to an *Arabidopsis* growth stage where the plant is still actively growing (mid-flowering). By growth stage 6.9 the plants have started senescing and flower production has stopped with <5 open flowers. Thus the growth stage 6.5 gives a fairly accurate estimate of the growth rate of the plant prior to senescence. An is average of the silique number at growth stage 6.5 was estimated for both WT and transgenics and total silique number is shown in the following table. This indicates again that silique number was at least 28% greater in lines over-expressing the polypeptide molecules corresponding SEQ ID NO: 2 (transformed lines) as compared to wild type lines at the same growth stage. As the plant proceeds to senescence, the relative increase appears to stay consistent and together with the increase in seed weight in the transgenic plant, contributes to the overall increase in seed yield per plant. Growth stage estimation was based on "Growth stage-based phenotypic analysis of *Arabidopsis*: A model for high throughput functional genomics in plants. Plant Cell. 13(7):1499, 2001"

TABLE 5

Number of Silique. WT is wild type plant and Transformed line is transgenic plant line expressing polypeptide molecules corresponding to SEQ ID. NO: 2.

| WT siliques | Average WT siliques | Transformed line siliques | Average Transformed line siliques |
|---|---|---|---|
| 88 | 88 | 124 | 113 |
| 87 |  | 123 |  |
| 81 |  | 126 |  |
| 78 |  | 112 |  |
| 84 |  | 104 |  |
| 80 |  | 102 |  |
| 96 |  | 112 |  |
| 98 |  | 113 |  |
| 100 |  | 105 |  |

Example 9

This example describes increase of seeds in transgenic soybean plants expressing polypeptide molecule corresponding to SEQ ID NO: 2.

Figure 7:
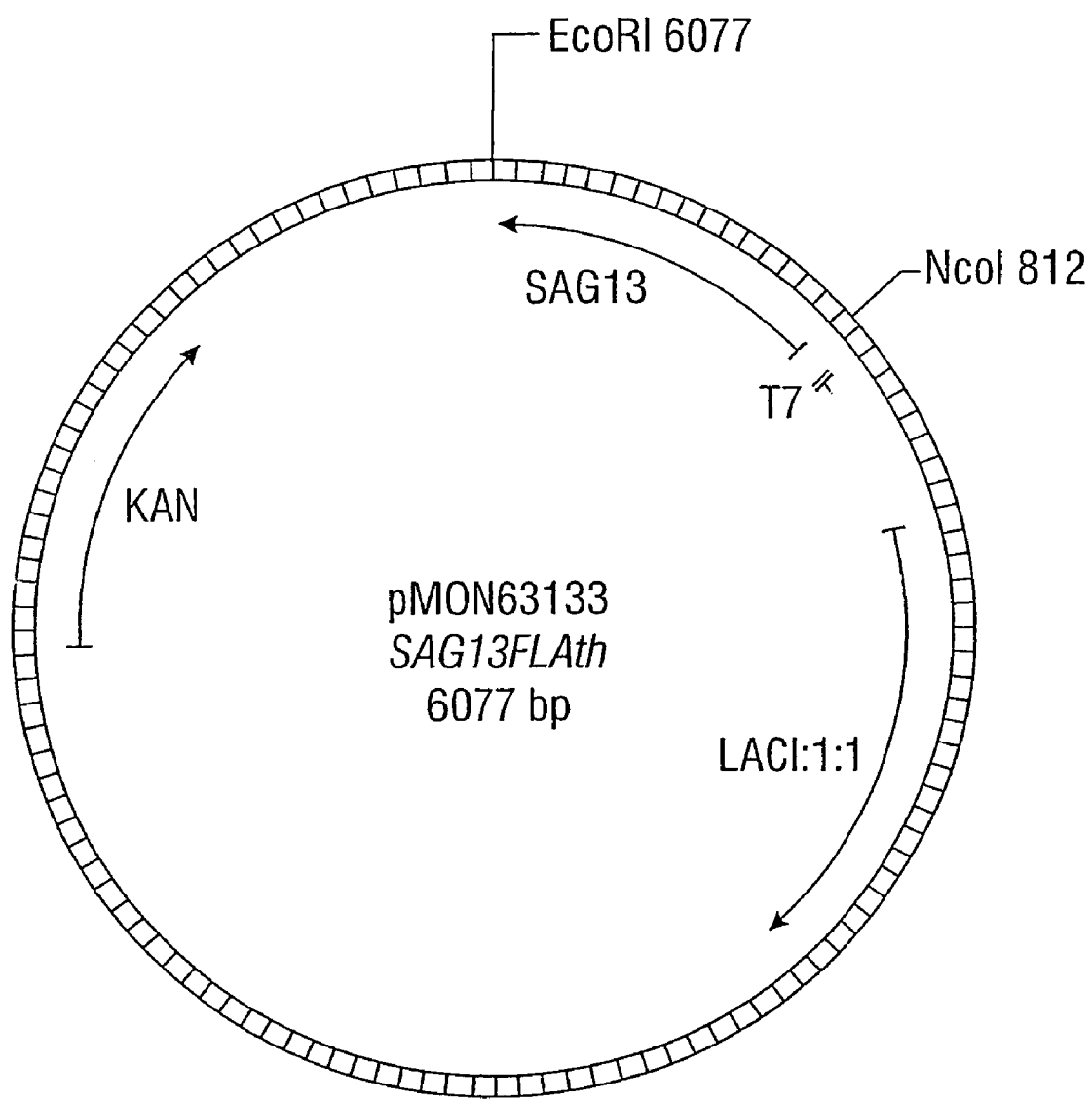
FIG. 7 shows a plasmid map for bacterial transformation vector pMON 63133 with its elements.
Figure 8:
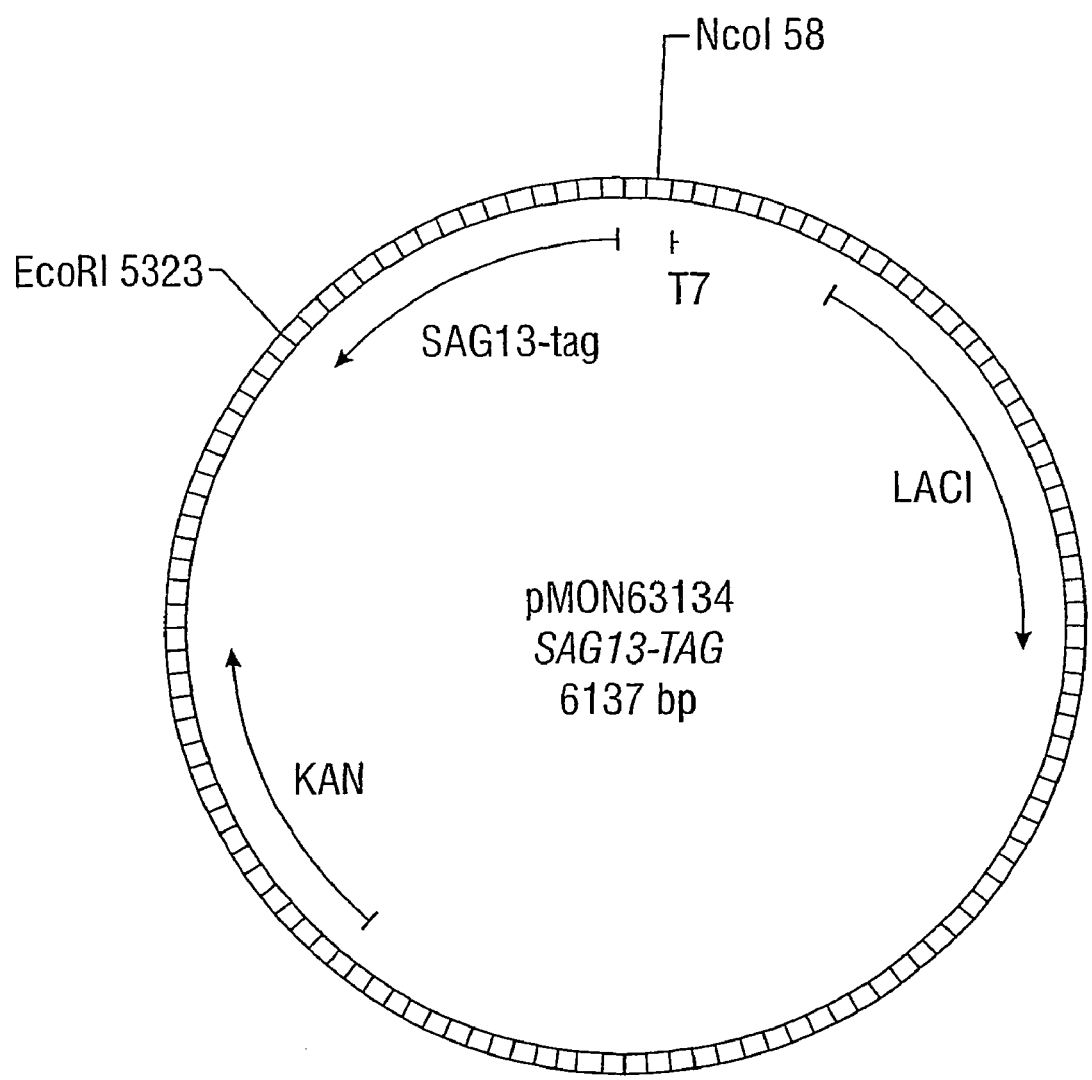
FIG. 8 shows a plasmid map for bacterial transformation vector pMON 6134 with its elements.
Figure 9:
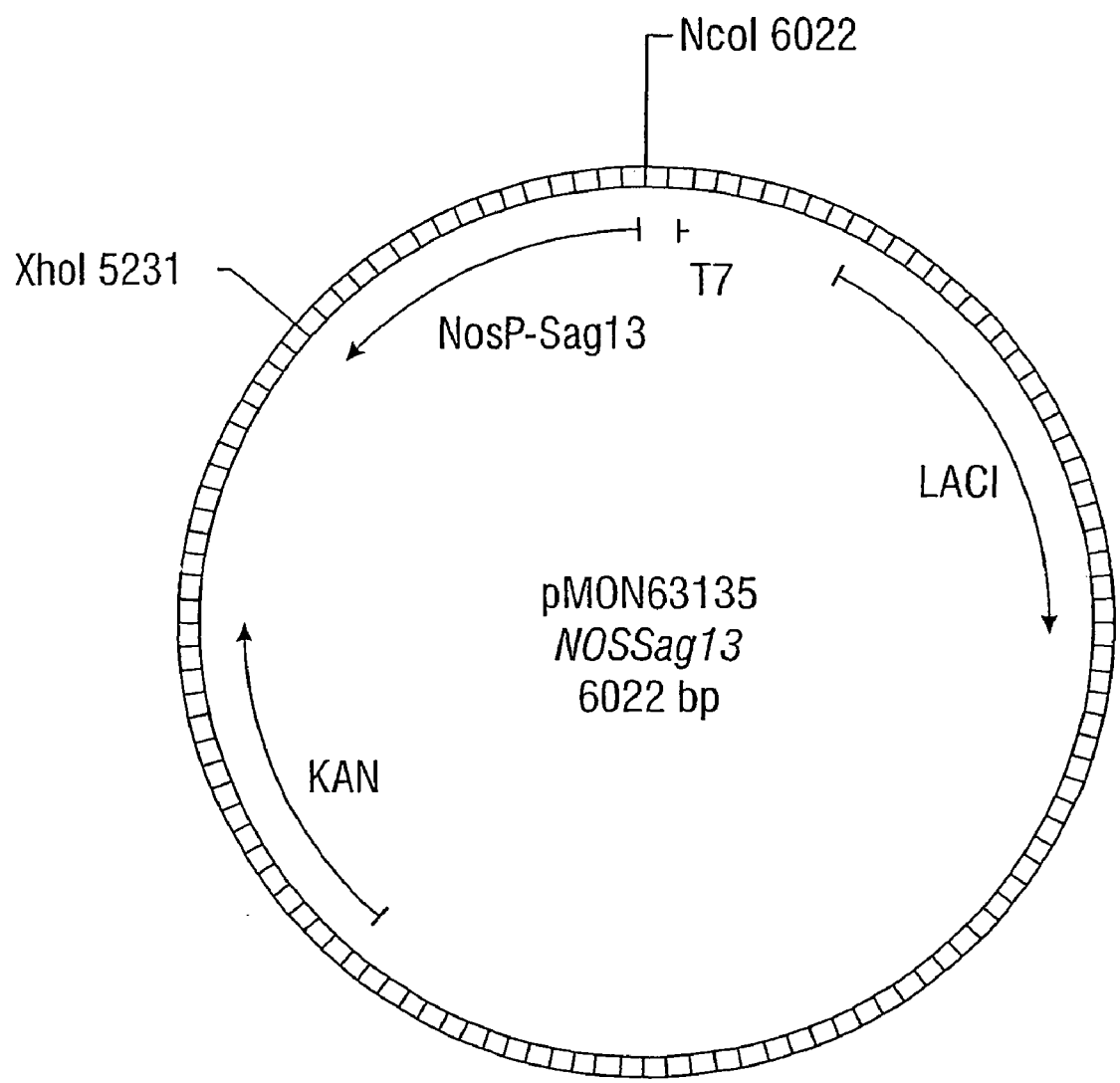
FIG. 9 shows a plasmid map for bacterial transformation vector pMON 6135 with its elements.
Figure 11:
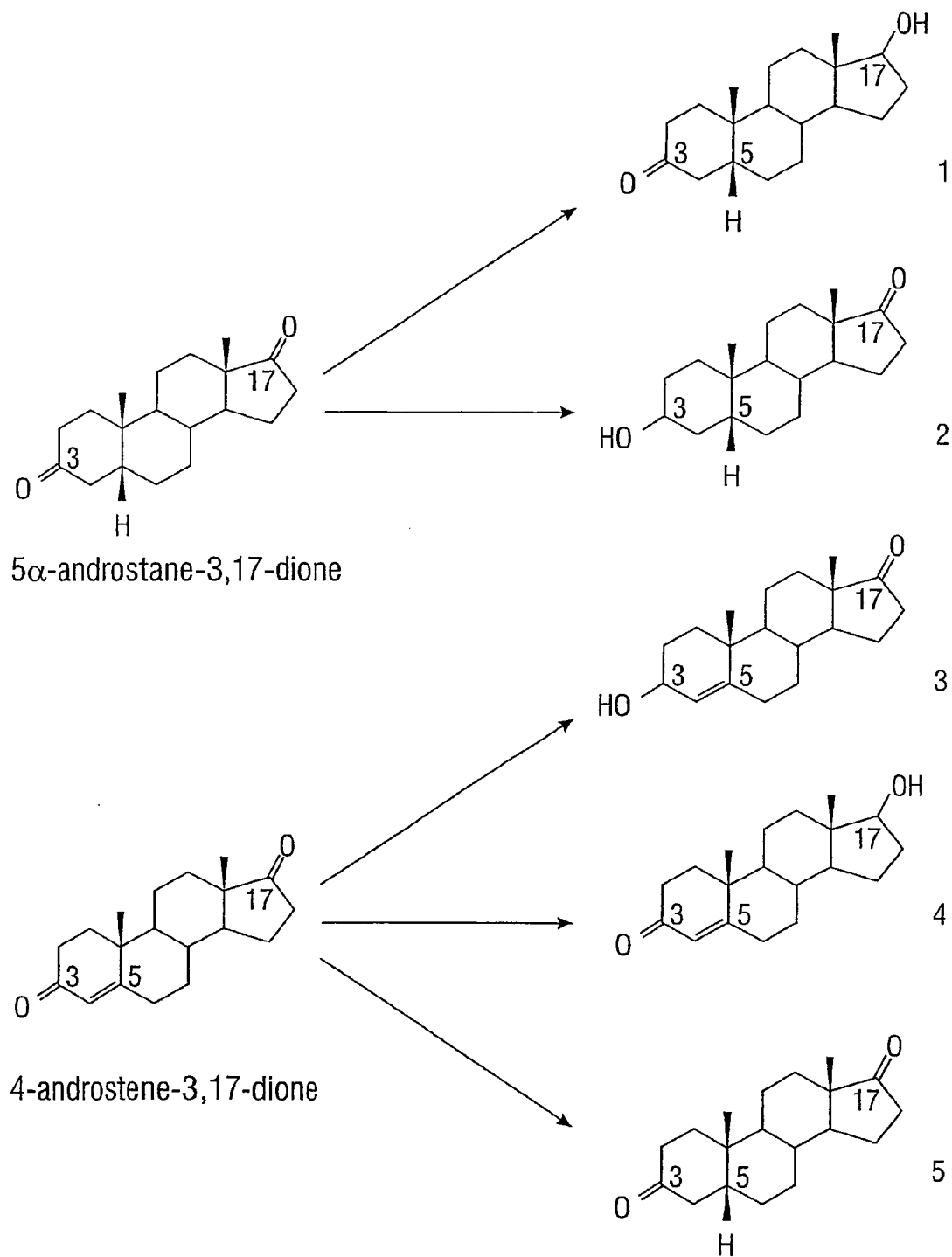
FIG. 11 shows putative products from steroid reductase activity.
Figure 12:
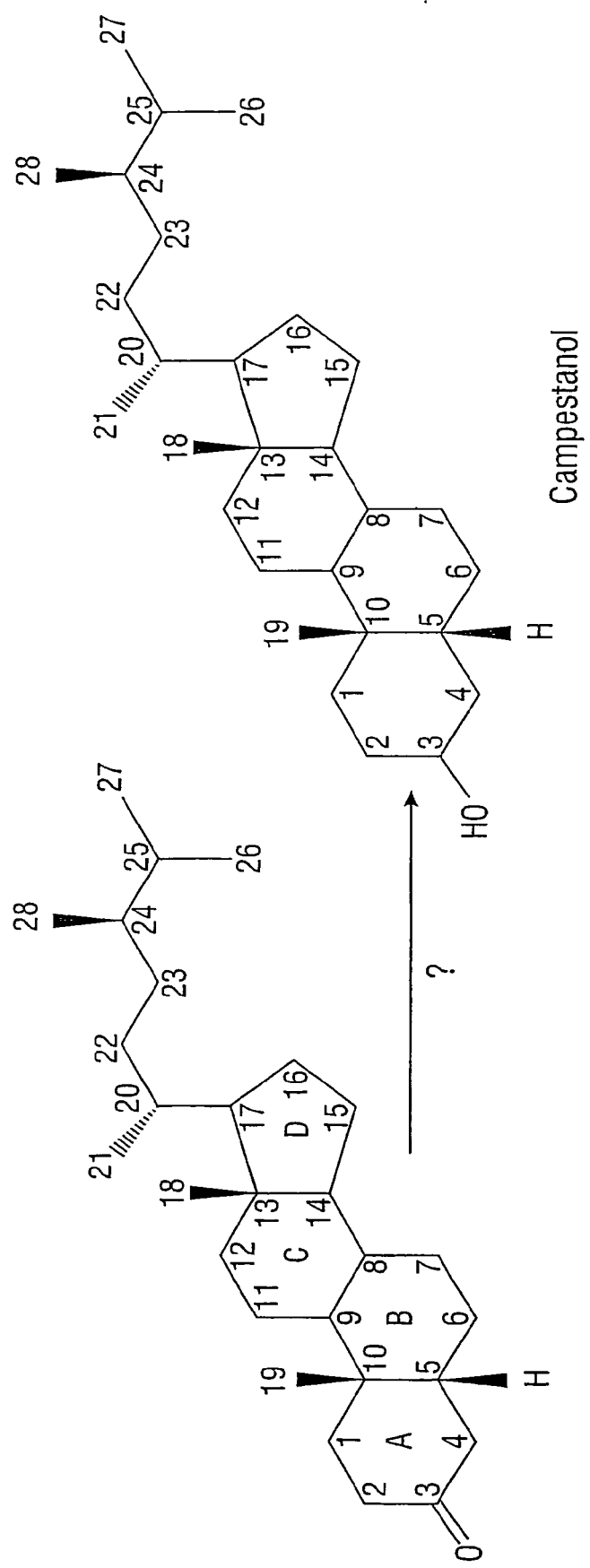
FIG. 12 shows a potential steroid reductase reaction.

Soybean plants were transformed with pMON73955 (FIG. 7) to constitutively express SEQ ID NO: 2. Soybean transformation is performed essentially as described in WO 00/42207, herein incorporated by reference in its entirety. R1 seed from 10 events out of 44 events were advanced in Puerto Rico (PR) based on the gene copy number in plants. Soybean transformation was performed essentially as described in WO 00/42207, herein incorporated by reference in its is entirety. Preliminary data indicates that 1 of the 10 events in PR showed a phenotype similar to that seen for the *Arabidopsis* over-expression of SEQ ID NO: 2 (pMON 57521 FIG. 2) i.e. more pods and more branches as well as short, fat pods with fewer seed. More two-seeded pods were observed and the seed was larger than seed from wild type and negative plants (but seed size was not doubled as seen in *Arabidopsis*). In addition the positives (transgenic line expressing genes of interest) from this event "A" produced more seed than the negatives (transgenic line NOT expressing genes of interest) as shown in Table 7. Table 6 shows the seed weight of individual plants (events) from the R1 generation and seed weight in the R2 generation. R2 seed weight in this table is an average of seed weight of all lines from the original R1 event. All numbers are expressed as a percentage of wild-type (WT). Detailed R2 seed weight and seed number data from single lines (positives versus negatives) of the best performing event "A" is shown in Table 7. In general a good correlation is observed between positives and negatives for seed size and seed yield.

TABLE 6

R1 and R2 seed weights of 10 independent soybean transgenic events expressing SEQ ID NO: 2. Values are expressed as a percentage of wild-type where WT = 100%

| Pedigree | % R1 Seed weight | % R2 Seed weight |
| --- | --- | --- |
| Line A-1 | 154% | 163% |
| Line A-2 | 108% | 80% |
| Line A-3 | 97% | 109% |
| Line A-4 | 105% | 110% |
| Line A-5 | 91% | 83% |
| Line A-6 | 105% | 78% |
| Line A-7 | 102% | 95% |
| Line A-8 | 108% | 183% |
| Line A-9 | 105% | 115% |
| Line A-10 | 105% | 116% |

TABLE 7

R2 seed weights of individual lines from the large-seeded transgenic event "A" expressing SEQ ID NO: 2.

| Line | Total number of seed produced | Corresponding seed weight (gms) | Seed weight of 100 seed (gms) |
| --- | --- | --- | --- |
| A-1 POS | 144 | 28 | 19.44 |
| A-1 POS | 76 | 15 | 19.74 |
| A-1 POS | 126 | 30 | 23.81 |
| A-1 POS | 124 | 21 | 16.94 |
| A-1 POS | 166 | 34 | 20.48 |
| A-1 POS | 118 | 23 | 19.49 |
| A-1 NEG | 98 | 17 | 17.35 |
| A-1 NEG | 50 | 11 | 22 |
| A-1 NEG | 97 | 16 | 16.49 |
| A-1 NEG | 66 | 12 | 18.18 |
| A-1 NEG | 58 | 10 | 17.24 |
| A-1 NEG | 75 | 15 | 20 |
| A-1 NEG | 92 | 16 | 17.39 |
| A-1 NEG | 75 | 14 | 18.67 |

Example 10

This example describes over expression of the protein in bacterial cells for purification of the protein so as to screen for the activity of polypeptide molecules.

Figure 3:
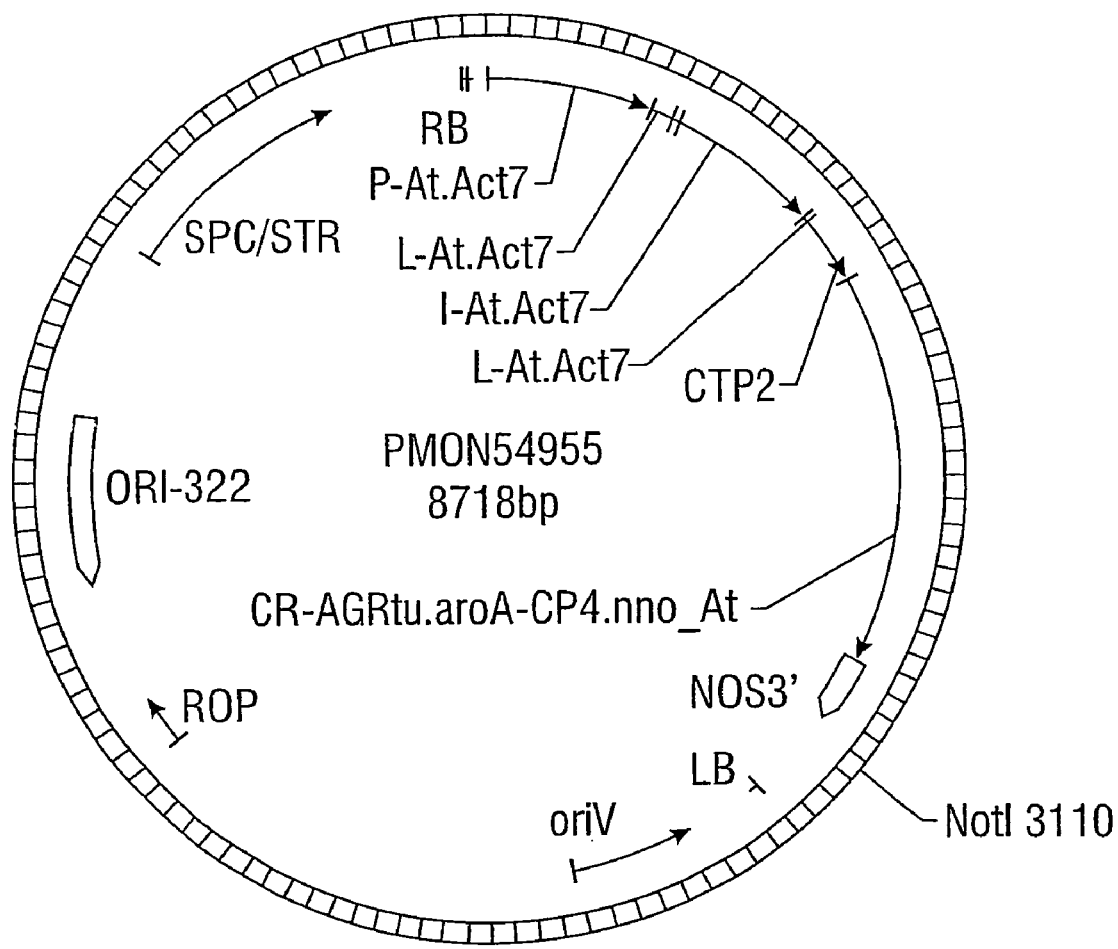
FIG. 3 shows a plasmid map for plant transformation vector pMON 54955 with its elements.
Figure 5:
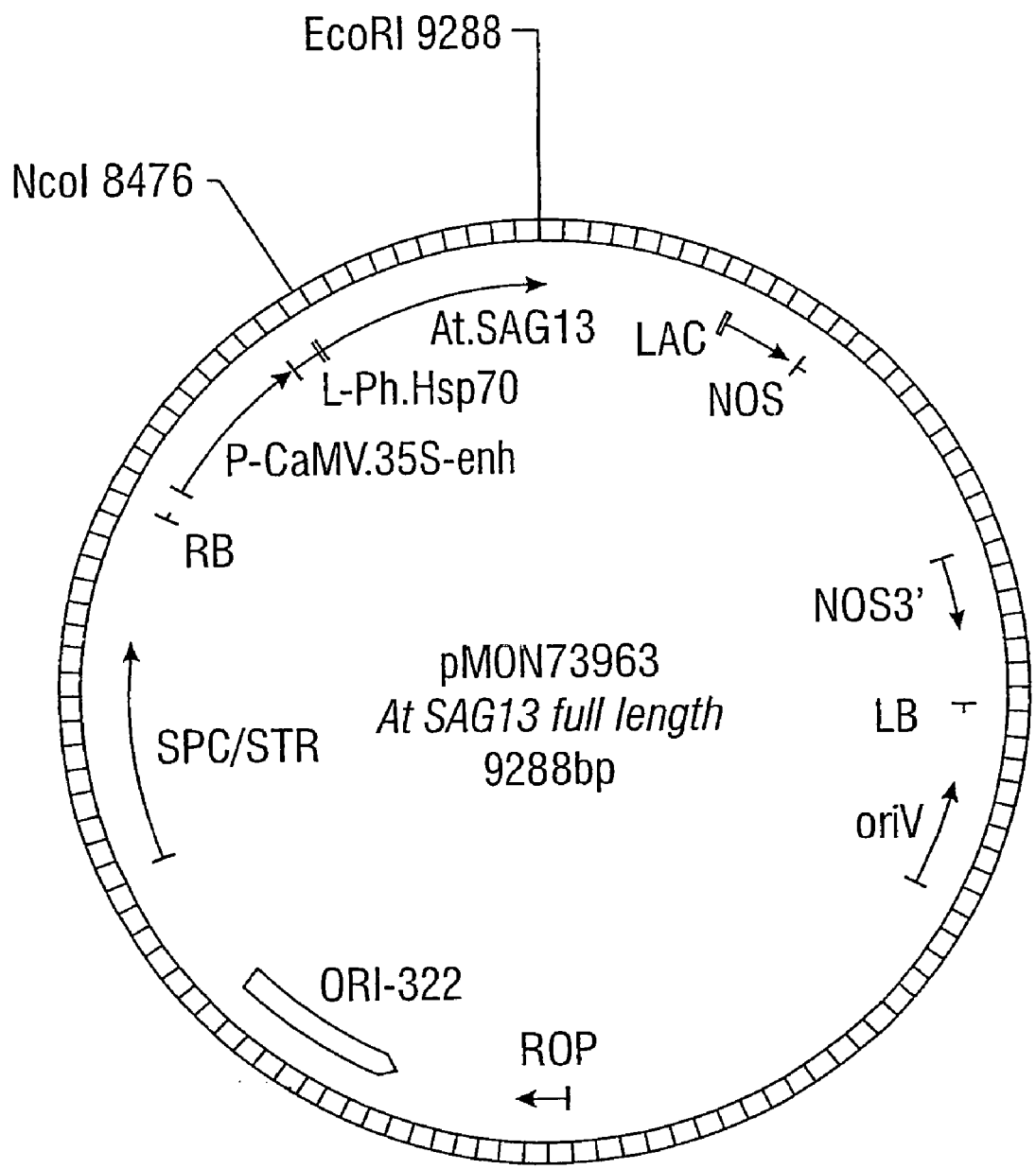
FIG. 5 shows a plasmid map for plant transformation vector pMON 73963 with its elements.
Figure 6:
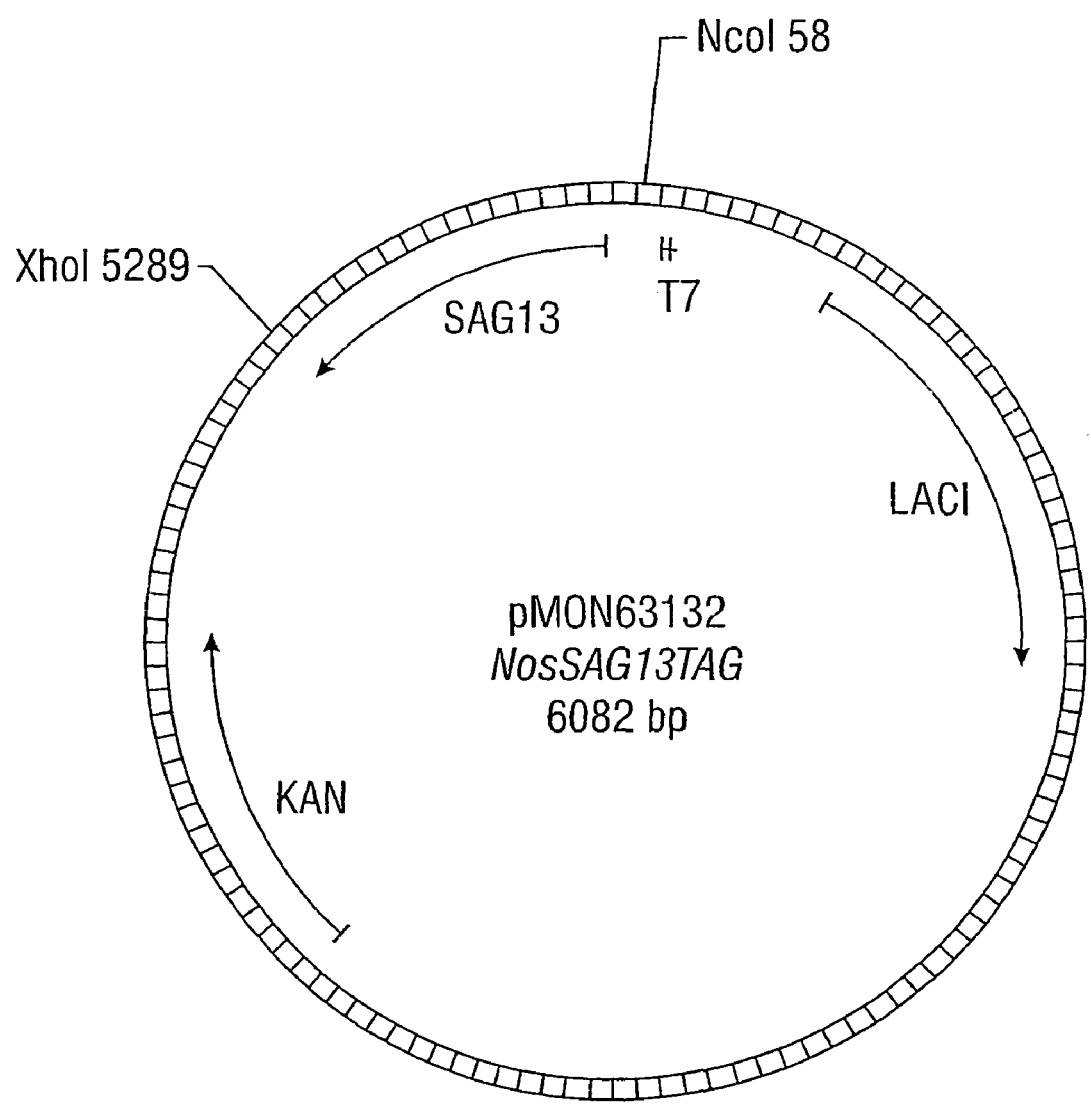
FIG. 6 shows a plasmid map for bacterial transformation vector pMON 63132 with its elements.

(A) Cloning of the Nucleotide Molecules of the Present Invention for Expression of Corresponding Peptides.

pMON57521 (FIG. 2), pMON73963 (FIG. 3), or *Nostoc punctiforme* (Nostoc) genomic DNA is used as a DNA template source for polymerase chain reaction amplification (PCR) of DNA for cloning into bacterial cells so as to express the *Arabidopsis thaliana* protein corresponding to SEQ ID NO: 2, SEQ ID NO: 4, or Nostoc protein corresponding to SEQ ID NO: 50. Design of primers and PCR reaction conditions are determined as described in the article PCR Strategies, Edited by Michael A. Innis; David H. Gelfand; & Johm J. Sninsky; Academic Press 1995 and PCR Protocols, A Guide to Method and Applications, Edited by Michael A. Innis; David H. Gelfand; Johm J. Sninsky; & Thomas J. White Academic Press 1990, herein incorporated by is reference in its entirety. All reagents for performing the PCR reaction can be procured from Gibco BRL, Life Technologies, Gaithersburg, Md. U.S.A. The thermocycler needed for performing PCR reaction was procured from Applied Biosystems (Perkin-Elmer Corp., Applied Biosystems Div., Foster City, Calif.). The polynucleotide sequence of the amplicon produced from *Arabidopsis* is shown in SEQ ID NO: 1 and SEQ ID NO: 3. PCR primer pairs SEQ ID NO: 57 and SEQ ID NO: 58 were used for performing the reaction to obtain the *Arabidopsis* amplicon. *Arabidopsis* amplicons were subcloned into a pET-28b vector (*E coli* expression vector, Novagen, Madison, Wis., USA) and were sequenced by using sequencing primers SEQ ID NO: 59 and SEQ ID NO: 60 to confirm the sequence of the cloned polynucleotide molecule. Similarly Nostoc amplicons were generated by using Nostoc genomic DNA as template with primers pairs SEQ ID NO: 61 and SEQ ID NO: 63 or SEQ ID NO: 62 and SEQ ID NO: 63. Nostoc amplicons were also subcloned in to the pET-28b vector and were sequenced by using sequencing primers SEQ ID NO: 64 and SEQ ID NO: 65 to confirm the polynucleotide sequence of the cloned polynucleotide molecule. Primer Sequence for amplification and sequencing of molecules of invention from *Arabidopsis* and Nostoc are shown in FIG. 10. These constructs contained a candidate from *Arabidopsis* SEQ ID NO: 3 and the closest Nostoc homologue SEQ ID NO: 49, both with and without an N-terminal His-tag. An N-terminal His-tag was chosen based on the crystal structures (Nakajima et al. *PNAS* 95, 4876, 1998) of the related proteins (tropinone reductases) which suggested that the N terminus would not interfere with the dimerization domain. The resultant vectors pMON 63132 (FIG. 4, Nostoc Histag), pMON 63133 (FIG. 5, *A. thaliana*), pMON 63134 (FIG. 6, *A. thaliana* Histag), and pMON 63135 FIG. 7 Nostoc) were used in the following examples for expression of the protein molecules. As described herein any molecules of present invention can be cloned for expression of its corresponding peptide or protein molecule.

(B) Over Expression/Purification of Protein Molecules of the Present Invention:

Appropriate clones (as shown in FIGS. 4-7) expressing all four versions of above-mentioned proteins in *E. coli* were identified by appropriate antibiotic selection as described by the manufacturer (Novagen 441 Charmany Drive Madison, Wis., 53719, USA). Expressed protein bands of the predicted sizes were identified by analytical SDS poly acrylamide gel electrophoresis (Laemmli, U.K., Nature, 227, 680, 1970) to confirm the expression of desired protein. A gel with the His tagged and Non tagged proteins for all four proteins clearly shows the size differences. Protein obtained from the plasmid pMON63134 (FIG. 6) was chosen for assay work described below. Protein extracts were prepared by freeze thawing and sonication as described Cull and McHenry (Cull M and McHenry C. S. Methods in Enzymology 182, 147-153, 1990). Pellets were resuspended in an appropriate volume of either 50 mM Tris-HCl pH 7.4 250 mM NaCl and 500 µM EDTA with 0.05% CHAPS and 1 mM ABESF or 50 mM $KH_2PO_4$ pH-7.2 250 mM NaCl and 250 µM EDTA with 0.05% CHAPS and 1 mM ABESF, buffer. Crude extracts containing His-tagged protein were applied to equilibrated His-Trap (Pharmacia Piscataway, N.J.) columns and purified by standard procedures as described by the manufacturer of the columns. Steps included a 10 mM imidazole elution/wash and elution in 250 mM imidazole. As a result the *Arabidopsis* tagged protein was partially purified (approximately 85-90% by SDS-PAGE stained with Coomasie Blue). Purified samples were gel filtered into 50 mM $KH_2PO_4$ pH-7.2 250 mM NaCl and 250 µM EDTA, 10% glycerol and stored at −80° C. until use. Protein concentrations were 1.5 to 1.7 mg/mL, based on the method of Bradford (Bradford M, Anal Biochem, 72, 248, 1976 and Bio-Rad Laboratories Procedure bulletin 1123) with BSA standard (Bradford reagent and BSA was from Bio-Rad Laboratories Headquarters 1000 Alfred Nobel Drive Hercules, Calif. 94547). The assays described below used 10 or 15 uL of this solution (15 to 22 µg per reaction).

(C) Catalytic or Enymatic Activity Determination of Peptide/Protein Molecules of Present Invention.

Spectrophotometric assays were used for determination of enzyme activities of purified proteins. Assays were based on earlier described methods (Portsteffen et al. *Phyochemistry*, 37, 391, 1994). Consumption or production of NADPH was observed at 340 nm. Assays were performed in a Varian Cary 50 Bio spectrophotometer (Varian Instruments Inc. AA, ICP, UV, to Fluorescence Products 679 Springvale RoadMulgrave, Victoria 3170 Australia). All assays were run at 30° C. for 10 to 30 minutes in 1 mL volumes using 100 mM $KH_2PO_4$ pH 6.5, 250 µM EDTA or 50 mM $KH_2PO_4$ pH-7.2, 250 mM NaCl, and 250 µM EDTA as reaction buffer. If metals were added they were supplemented to reactions in cuvettes from 100 mM stocks of either $ZnCl_2$ and or $MgCl_2$. Substrates included those found in table 8. All assays contained 3 to 30 µg of protein 200 to 400 µM NADPH or NADP and 100 µM to 10 mM substrate (acetone 60 mM). Controls contained no substrate to determine the background rate of consumption and degradation of NADPH. NADPH solutions were freshly made and checked by UV-vis for degradation. Enzyme solutions were supplemented with 1 mM $MgCl_2$ and 1 mM $ZnCl_2$ which were at 1.5 to 1.7 mg/mL concentrations. The assays used 10 or 15 µl of this solution (ca. 15 to 22 µg per reaction). Stock solutions of the substrates (20 to 500 mM) were made up in a reaction buffer or as noted. Steroids solutions were made in 100% EtOH. From these stock solutions additions to the assays were made directly. Precipitation of steroids was observed. Thus, the soluble concentration of steroids in reaction mixture is not accurately known in each case. However, good estimate of substrate (sterol) concentration would be 100 to 200 µM for a saturated solution under these conditions. There was a clear difference in rate observed by changing concentration from 26 µM to 260 µM indicating that saturation may be between the two points both for enzyme activity and substrate solubility. At these concentrations precipitation did not have an effect on the absorbance changes at 340 nm as evidenced by controls containing substrate and NADPH. In addition to cell extract control, a substrate control was also employed because solutions of some substrates tested can have a lower pH at described assay conditions which may affect rates of NADPH degradation and enzyme activity under assay conditions. Results of the substrates tested can be found in Table 10 below.

These results (Table 8 to 10) show that the *A. thaliana* protein molecule SEQ ID NO: 4 has significant steroid reductase activity. Combined with other biological data these results suggest that SEQ ID NO: 4 is likely a steroid reductase with true substrates that are most likely brassinosteroids. These results do not preclude the possibility that another compound class might act as substrate but results suggest that the substrate is a ketone moiety potentially in a steroid ring system.

TABLE 8

Zero Order Result Table using acetone as substrate (60 mM) shows evidence of reductase activity. Turnover (consumption of NADPH) is observed in the reductive direction. Slopes (for acetone, lines 1 and 2) indicate the difference from control is 10 fold. Controls (lines 3 and 4) were identical except for the omission of acetone.

| Sample | Start (min) | Stop (min) | Slope (Abs/min) | A Start | A Stop | S.D. |
|---|---|---|---|---|---|---|
| Acetone | 0.000 | 10.00 | −0.0118 | 0.8869 | 0.7640 | 0.0016 |
| Acetone | 0.000 | 10.00 | −0.0111 | 0.8655 | 0.7502 | 0.0025 |
| Control | 0.000 | 10.00 | −0.0006 | 0.8609 | 0.8547 | 0.0006 |
| Control | 0.000 | 10.00 | −0.0010 | 0.8773 | 0.8683 | 0.0011 |

Start = start time,
Stop = stop time,
Slope is change in absorbance over time,
A start is starting absorbance,
A stop is ending absorbance.

TABLE 9

Zero Order Result Table. This table shows elected data for 5α-androstane-3,17-dione in a reductase assay. This example shows the results for three reactions with acetone, three reactions with 5α-androstane-3,17-dione and two controls. Table 8 shows the initial rates as estimated by linear fit between 0 and 5 minutes. The results for 5α-androstane-3,17-dione shown here are the best of any substrate at the same concentration (approx 200 µM). 4-androstene-3,17-dione is the next best substrate with a rate on the order of 2.5 to 4 times slower than this under the same conditions (not shown). Acetone results at similar concentrations (Table 7 shows results at high acetone concentration) are on the order of 10 to 20 times slower and nearly at background levels. Similar results have been obtained with multiple batches of enzyme and substrate.

| Sample | Start (min) | Stop (min) | Slope (Abs/min) | A Start | A Stop | S.D. |
|---|---|---|---|---|---|---|
| 5-alpha | 0.000 | 5.000 | −0.0632 | 1.4399 | 1.1322 | 0.0018 |
| 5-alpha | 0.000 | 5.000 | −0.0611 | 1.4105 | 1.1092 | 0.0022 |
| 5-alpha | 0.000 | 5.000 | −0.0652 | 1.4710 | 1.1652 | 0.0030 |
| acetone | 0.000 | 5.000 | −0.0049 | 1.5050 | 1.4793 | 0.0018 |
| acetone | 0.000 | 5.000 | −0.0047 | 1.3902 | 1.3961 | 0.0012 |
| acetone | 0.000 | 5.000 | −0.0041 | 1.4584 | 1.4352 | 0.0014 |
| Control | 0.000 | 5.000 | −0.0030 | 1.5256 | 1.5118 | 0.0013 |
| Control | 0.000 | 5.000 | −0.0035 | 1.4898 | 1.4743 | 0.0018 |

Start = start time,
Stop = stop time,
Slope is change in absorbance over time,
A start is starting absorbance,
A stop is ending absorbance.

TABLE 10

Substrates tested.

| Substrate | Name | Activity | Comments/references |
|---|---|---|---|
|  | acetone | Yes 65 mM Much lower at lower concentrations | |

TABLE 10-continued

| | Substrates tested. | | |
|---|---|---|---|
| 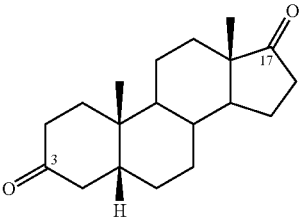 | 5α-androstane-3,17-dione | YES 100 μM | 17β activity Chemico-biological interactions 130-132 (2001)783-803 |
| 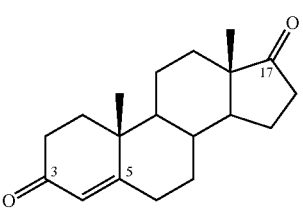 | 4-androstene-3,17-dione | YES 100 μM | 3α activity Chemico-biological interactions 130-132 (2001)783-803 5α activity (PNAS, 94, 3354-3359, 1997) |
| 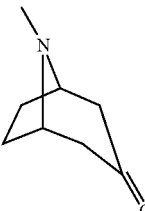 | Tropinone | No retested with new enzyme 1 and 10 mM | (Photochemistry, 37, 391-400, 1994) |
| 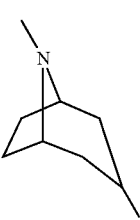 | Tropine | No retested with new enzyme 1 and 10 mM | (Photochemistry, 37, 391-400, 1994). |
| 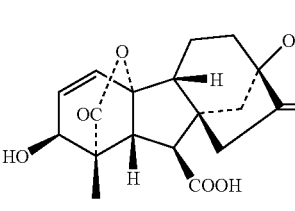 | Gibberellic Acid (GA$_3$) | No 1 and 10 mM | |

| Additional substrates tested | Name | Activity | Chosen based on informatics results 2$^{nd}$ tier possibilities |
|---|---|---|---|
| 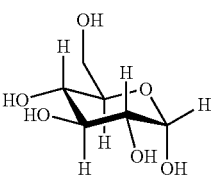 | D-Glucose | No 25 mM | |
| 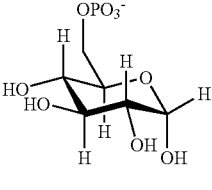 | Glucose 6 phosphate | No 25 mM | |

TABLE 10-continued

Substrates tested.

| Structure | Substrate | Activity / Conc. | Notes |
|---|---|---|---|
| (Glucono 1,5 lactone structure) | Glucono 1,5 lactone | No / 25 mM | Stereoisomer of δ-gluconolactone. Easily hydrolyzed in $H_2O$. |
| (δ-gluconolactone structure) | δ-gluconolactone | No / 25 mM | Stereoisomer of Glucono 1,5 lactone. pH of solution is very low i.e. below 3. |
| (Potassium d-gluconate Fischer structure) | Potassium d-gluconate | No / 25 mM | Potassium salt used |
| (Arabinitol Fischer structure) | Arabinitol | No / 25 mM | |
| (Sucrose structure) | Sucrose | No / 25 mM | |
| (Isopropanol structure) | isopropanol | Yes / 68 mM | At high concentrations it is a substrate for the reverse reaction but at same concentrations is a poorer substrate than acetone indicating potential preference for the reductase activity under these conditions. |

Example 11

In the following example a large number of DNA sequences were searched using BlastA (Altschul, Stephen F., Thomas L. Madden, Alejandro A. Schaffer, Jinghui Zhang, Zheng Zhang, Webb Miller, and David J. Lipman, Nucleic Acids Res. (25)3389-3402 (1997)) to find various homologs, paralogs or orthologs of the gene of the present invention. These sequences are determined from cDNA libraries prepared from a variety plant species and tissues.

For construction of cDNA libraries, tissue is harvested and immediately frozen in liquid nitrogen and stored at −80° C. until total RNA extraction. Total RNA is purified from tissue using Trizol reagent from Life Technologies (Gibco BRL, Life Technologies, Gaithersburg, Md. U.S.A.), as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.) is used, following the conditions suggested by the manufacturer.

The cDNA libraries are plated on LB agar containing the appropriate antibiotics for selection and incubated at 37° for sufficient time to allow the growth of individual colonies. Single selective media colonies are individually placed in each well of a 96-well microtiter plates containing LB liquid including the selective antibiotics. The plates are incubated overnight at approximately 37° C. with gentle shaking to promote growth of the cultures.

The plasmid DNA is isolated from each clone using Qiaprep plasmid isolation kits, using the conditions recommended by the manufacturer (Qiagen Inc., Santa Clara, Calif. U.S.A.).

The template plasmid DNA clones are used for subsequent sequencing. For sequencing the cDNA libraries, a commercially available sequencing kit, such as the ABI PRISM dRhodamine Terminator Cycle Sequencing Ready Reaction Kit with AmpliTaq® DNA Polymerase, FS, is used under the conditions recommended by the manufacturer (PE Applied Biosystems, Foster City, Calif.). The cDNAs of the present invention are generated by sequencing initiated from the 5' end or 3' end of each cDNA clone. Entire inserts or only part of the inserts (ESTs or expressed sequenced tags) are sequenced.

A number of DNA sequencing techniques are known in the art, including fluorescence-based sequencing methodologies. These methods have the detection, automation and instrumentation capability necessary for the analysis of large volumes of sequence data. Currently, the 377 and 3700 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, N.Y., the entirety of which is herein incorporated by reference).

The generated ESTs (including any full-length cDNA inserts or complete coding sequences) are combined with ESTs and full-length cDNA sequences in public databases such as GenBank. Duplicate sequences are removed, and duplicate sequence identification numbers are replaced. The combined dataset is then clustered and assembled using Pangea Systems tool identified as CAT v.3.2. First, the EST sequences are screened and filtered, e.g. high frequency words are masked to prevent spurious clustering; sequence common to known contaminants such as cloning bacteria are masked; high frequency repeated sequences and simple sequences are masked; unmasked sequences of less than 100 bp are eliminated. The screened and filtered ESTs are combined and subjected to a word-based clustering algorithm which calculates sequence pair distances based on word frequencies and uses a single linkage method to group like sequences into clusters of more than one sequence, as appropriate. Clustered sequences are assembled individually using an iterative method based on PHRAP/CRAW/MAP providing one or more self-consistent consensus sequences and inconsistent singleton sequences. The assembled clustered sequence files are checked for completeness and parsed to create data representing each consensus contiguous sequence (contig), the initial EST sequences, and the relative position of each EST in a respective contig. The sequence of the 5' most clone is identified from each contig. The initial sequences that are not included in a contig are separated out.

Above described databases with nucleotide and peptide sequences were queried with sequences of the present invention to get following homologues, orthologs or paralogs as shown in following table. The BLAST 2.2.1 software (Altschul, Stephen F., Thomas L. Madden, Alejandro A. Schaffer, Jinghui Zhang, Zheng Zhang, Webb Miller, and David J. Lipman Nucleic Acids Res. (25)3389-3402 (1997), with BLOSUM62 matrix and "no Filter" options, was used in the queries. As when necessary, frame-shifts in the DNA sequences of the homologues were detected by aligning the DNA sequence of the homologue in question to the protein sequence of present invention, using the "frame+_n2p" program with default parameters in the GenCore software package (Compugen Inc., 1998). Such frame-shifts were conceptually corrected to yield open reading frames. The "translate" program with default parameters in the same package was used to translate open reading frames to corresponding peptide sequences based on standard genetic codes.

SEQ ID NO: 1 exhibits 52.857% percent identity with its closest known functional gene, identified using the BLAST 2.2.1 software with BLOSUM62 matrix and "no Filter" options (Genbank accession number gi|1717752|sp|P50162|TRN1_DATST). SEQ ID NO: 1 exhibits identity of 111 amino acid residues over its entire length of 210 amino acids with tropinone reductase of *Datura stramonium* (Genbank accession number gi|1717752|sp|P50162|TRN1_DATST). Due to this relationship, it is possible that enzymes with similar activities can also function in present invention, also DNA molecules encoding proteins that are closely related to tropinone reductase are an aspect of the present invention.

TABLE 11

| Seq num | Gene Bank Identity | Species |
|---|---|---|
| 1 | none | *Arabidopsis thaliana* |
| 2 | none | *Arabidopsis thaliana* |
| 3 | none | *Arabidopsis thaliana* |
| 4 | none | *Arabidopsis thaliana* |
| 5 | gi|3980405|gb|AAC95208.1|_cds | *Arabidopsis thaliana* |
| 6 | gi|3980405|gb|AAC95208.1| | *Arabidopsis thaliana* |
| 7 | gi|3980415|gb|AAC95218.1|_cds | *Arabidopsis thaliana* |
| 8 | gi|3980415|gb|AAC95218.1| | *Arabidopsis thaliana* |
| 9 | gi|3980416|gb|AAC95219.1|_cds | *Arabidopsis thaliana* |
| 10 | gi|3980416|gb|AAC95219.1| | *Arabidopsis thaliana* |
| 11 | gi|3980398|gb|AAC95201.1|_cds | *Arabidopsis thaliana* |
| 12 | gi|3980398|gb|AAC95201.1| | *Arabidopsis thaliana* |
| 13 | gi|13605590|gb|AF361621.1|AF361621 | *Arabidopsis thaliana* |
| 14 | gi|13605591|gb|AAK32789.1|AF361621_1 | *Arabidopsis thaliana* |
| 15 | gi|8978342|dbj|BAA98195.1|_cds | *Arabidopsis thaliana* |
| 16 | gi|8978342|dbj|BAA98195.1| | *Arabidopsis thaliana* |
| 17 | gi|2880044|gb|AAC02738.1|_cds | *Arabidopsis thaliana* |
| 18 | gi|2880044|gb|AAC02738.1| | *Arabidopsis thaliana* |
| 19 | gi|3980401|gb|AAC95204.1|_cds | *Arabidopsis thaliana* |
| 20 | gi|3980401|gb|AAC95204.1| | *Arabidopsis thaliana* |
| 21 | gi|3980403|gb|AAC95206.1|_cds | *Arabidopsis thaliana* |
| 22 | gi|3980403|gb|AAC95206.1| | *Arabidopsis thaliana* |
| 23 | gi|3980406|gb|AAC95209.1|_cds | *Arabidopsis thaliana* |
| 24 | gi|3980406|gb|AAC95209.1| | *Arabidopsis thaliana* |
| 25 | ARATH-14MAR01-CLUSTER10347_2 | *Arabidopsis thaliana* |
| 26 | ARATH-14MAR01-CLUSTER10347_2_prot | *Arabidopsis thaliana* |
| 27 | ARATH-14MAR01-CLUSTER10347_3 | *Arabidopsis thaliana* |
| 28 | ARATH-14MAR01-CLUSTER10347_3_prot | *Arabidopsis thaliana* |
| 29 | ARATH-14MAR01-CLUSTER10347_5 | *Arabidopsis thaliana* |
| 30 | ARATH-14MAR01-CLUSTER10347_5_prot | *Arabidopsis thaliana* |
| 31 | ARATH-14MAR01-CLUSTER136303_1 | *Arabidopsis thaliana* |
| 32 | ARATH-14MAR01-CLUSTER136303_1_prot | *Arabidopsis thaliana* |
| 33 | None | *Glycine max* |
| 34 | None | *Glycine max* |
| 35 | None | *Glycine max* |
| 36 | None | *Glycine max* |

TABLE 11-continued

| Seq num | Gene Bank Identity | Species |
|---|---|---|
| 37 | None | Glycine max |
| 38 | None | Glycine max |
| 39 | None | Glycine max |
| 40 | None | Glycine max |
| 41 | None | Glycine max |
| 42 | None | Glycine max |
| 43 | None | Zea mays |
| 44 | None | Zea mays |
| 45 | None | Zea mays |
| 46 | None | Zea mays |
| 47 | None | Oryza sativa |

TABLE 11-continued

| Seq num | Gene Bank Identity | Species |
|---|---|---|
| 48 | None | Oryza sativa |
| 49 | gi\|17231948\|ref\|NP_488496.1\|_cds | Nostoc sp. PCC7120 |
| 50 | gi\|17231948\|ref\|NP_488496.1\| | Nostoc sp. PCC7120 |
| 51 | None | Xanthomonas campestris |
| 52 | None | Xanthomonas campestris |
| 53 | XYL200910 | Xylella fastidiosa |
| 54 | XYL200910_prot | Xylella fastidiosa |

The invention claimed is:

1. A method of increasing seed and organ size of a plant comprising the steps of
   a) transforming said plant with a DNA construct comprising a promoter that functions in plants, operably linked to a DNA molecule that encodes a protein, wherein said DNA molecule comprises SEQ ID NO:33, operably linked to a 3' termination region; and
   b) selecting a desired plant from a population of transformed plants containing said DNA construct;
   wherein said desired plant exhibits increased seed and organ size compared to a plant of a same plant species not transformed to contain said DNA construct.

2. The method of claim 1, wherein said promoter is selected from the group consisting of a CaMV promoter and an FMV promoter.

3. The method of claim 1, wherein said promoter comprises a heterologous plant constitutive promoter.

4. The method of claim 1, wherein said promoter is a tissue specific promoter or an organ enhanced promoter.

5. A method of increasing seed and organ size of a plant comprising the steps of:
   a) transforming said plant with a DNA construct comprising a promoter that functions in plants, operably linked to a DNA molecule that encodes a polypeptide comprising SEQ ID NO:34; wherein said DNA construct is operably linked to a 3' termination region; and
   b) selecting a plant from a population of transformed plants containing said DNA construct;
   wherein said plant exhibits increased seed and organ size compared to a plant of a same plant species not transformed to contain said DNA construct.

6. The method of claim 5, wherein said plant species is selected from the group consisting of: *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, loblolly pine, mango, melon, millet, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, southern pine, soybean, spinach, squash, strawberry, sugarbeet, sugarcane, sunflower, sweet potato, sweetgum, tangerine, tea, tobacco, tomato, turf, a vine, watermelon, wheat, yams, and zuchini.

7. A transgenic plant with increased seed and organ size compared to a non transformed plant of a same plant species, said transgenic plant comprising a DNA construct, wherein said DNA construct encodes a polypeptide comprising SEQ ID NO:34.

8. The transgenic plant of claim 7, wherein said plant species is selected from the group consisting of: *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, loblolly pine, mango, melon, millet, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, southern pine, soybean, spinach, squash, strawberry, sugarbeet, sugarcane, sunflower, sweet potato, sweetgum, tangerine, tea, tobacco, tomato, turf, a vine, watermelon, wheat, yams, and zuchini.

9. A progeny plant produced from said transgenic plant of claim 7, wherein said progeny plant comprises a DNA construct and wherein said DNA construct encodes a polypeptide comprising SEQ ID NO:34.

* * * * *